(12) United States Patent
Parsons et al.

(10) Patent No.: US 6,988,984 B2
(45) Date of Patent: Jan. 24, 2006

(54) DEVICE AND METHOD FOR THE MANIPULATION OF ORGANS

(76) Inventors: Matthew L. Parsons, 189 Lamphor St., Fall River, MA (US) 02721; Thomas E. Martin, 20 Waterview Ave., Riverside, RI (US) 02915

( * ) Notice: Subject to any disclaimer, the term of this patent is extended or adjusted under 35 U.S.C. 154(b) by 0 days.

(21) Appl. No.: 10/055,511

(22) Filed: Jan. 23, 2002

(65) Prior Publication Data

US 2003/0139644 A1 Jul. 24, 2003

(51) Int. Cl.
*A61F 13/00* (2006.01)

(52) U.S. Cl. ............................ 600/37; 600/201
(58) Field of Classification Search ............ 600/37, 600/897–98, 201, 208, 215; 606/191, 201, 606/202
See application file for complete search history.

(56) References Cited

U.S. PATENT DOCUMENTS

| 3,720,433 | A |   | 3/1973  | Rosfelder |         |
|-----------|---|---|---------|-----------|---------|
| 5,196,003 | A |   | 3/1993  | Bilweis   |         |
| 5,452,733 | A |   | 9/1995  | Sterman et al. |    |
| 5,636,643 | A | * | 6/1997  | Argenta et al. | 128/897 |
| 5,727,569 | A |   | 3/1998  | Benetti et al. |     |
| 5,799,661 | A |   | 9/1998  | Boyd et al. |       |
| 5,836,311 | A |   | 11/1998 | Borst et al. |      |
| 5,885,271 | A |   | 3/1999  | Hamilton et al. |   |
| 5,927,284 | A |   | 7/1999  | Borst et al. |      |
| 6,015,378 | A |   | 1/2000  | Rorst et al. |      |
| 6,032,672 | A |   | 3/2000  | Taylor    |         |
| 6,328,688 | B1|   | 12/2001 | Borst et al. |      |
| 6,334,843 | B1|   | 1/2002  | Borst et al. |      |
| 6,336,898 | B1|   | 1/2002  | Borst et al. |      |
| 6,478,728 | B1| * | 11/2002 | Wright    | 600/37  |
| 2001/0041827 | A1 |   | 11/2001 | Spence et al. |   |

FOREIGN PATENT DOCUMENTS

| EP | 0919193      | 6/1999   |        |
|----|--------------|----------|--------|
| EP | 0993806      | 4/2000   |        |
| WO | 96/39989     | * 12/1996 | 600/29 |
| WO | WO 97/10753  | 3/1997   |        |
| WO | WO 99/60929  | 12/1999  |        |
| WO | WO 01/17437  | 3/2001   |        |
| WO | WO 01/80745  | 11/2001  |        |

OTHER PUBLICATIONS

European Search Report attached to Reference BA.

* cited by examiner

*Primary Examiner*—John P. Lacyk
(74) *Attorney, Agent, or Firm*—Baker & Hostetler, LLP

(57) ABSTRACT

A manipulation mechanism that can be attached to the heart and other organs of the body so that the organs can be positioned, lifted, turned and held in place during diagnosis, testing, treatment and surgical procedures on the organs.

18 Claims, 44 Drawing Sheets

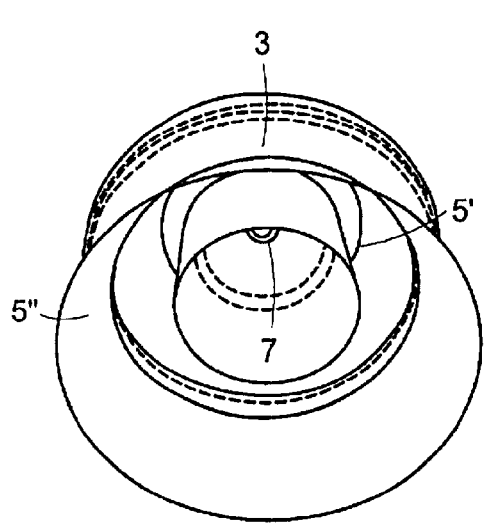 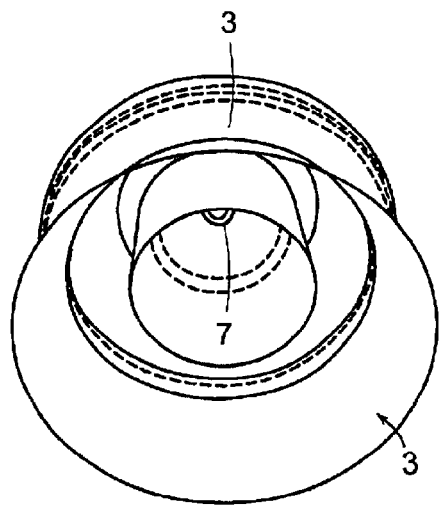
FIG. 21A  FIG. 21B
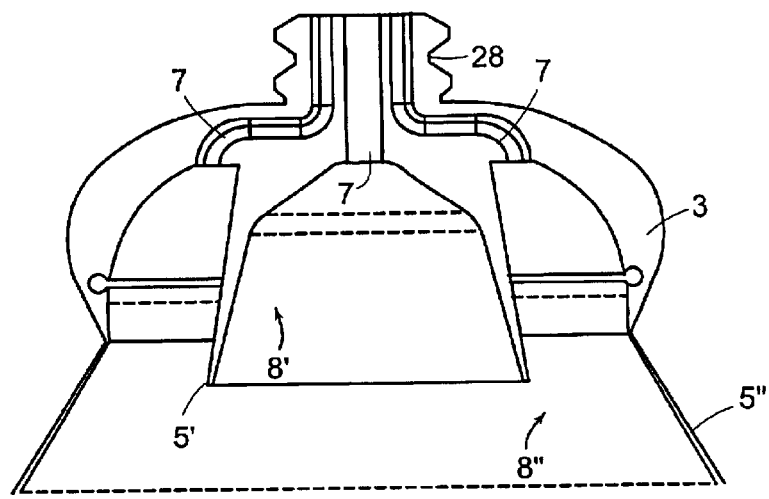
FIG. 22

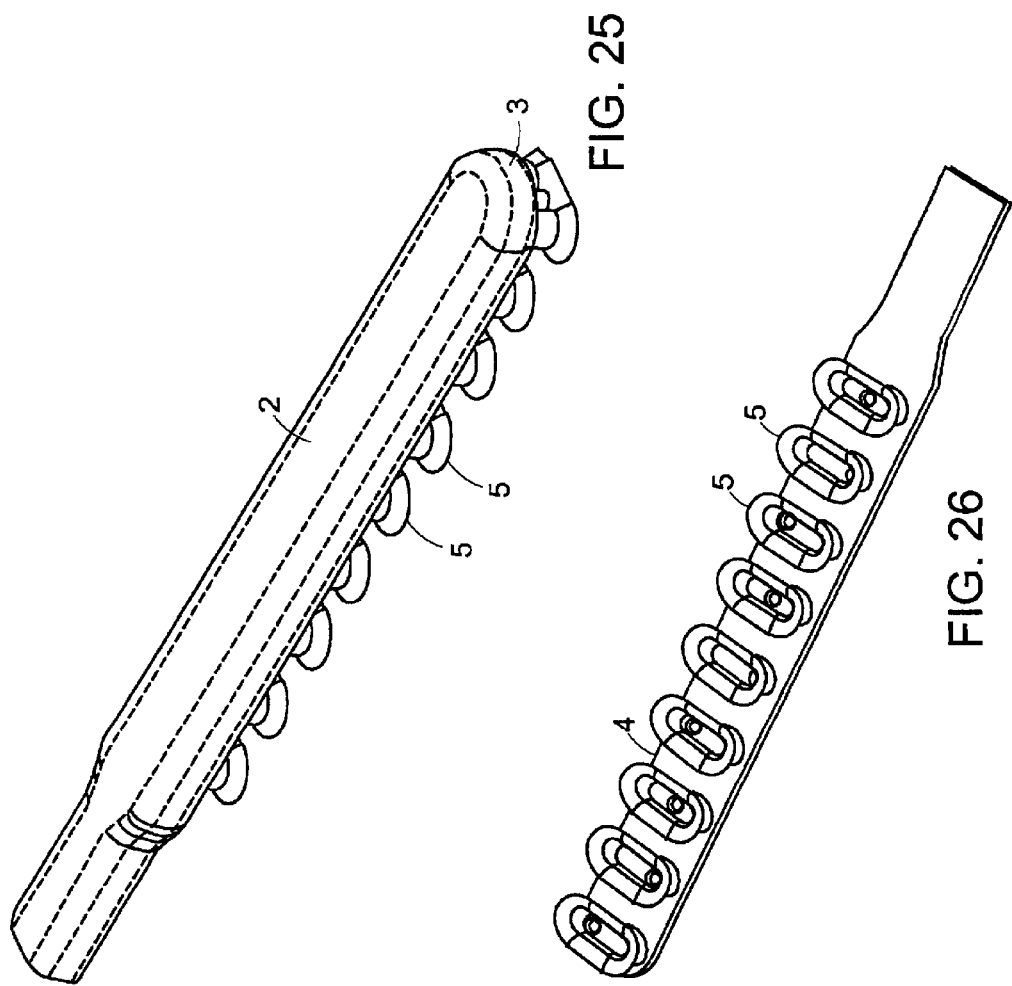

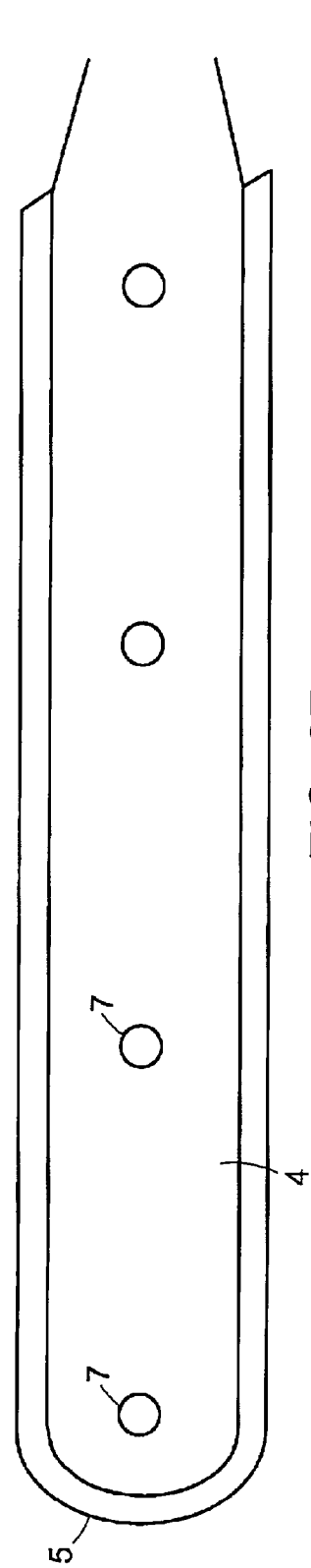
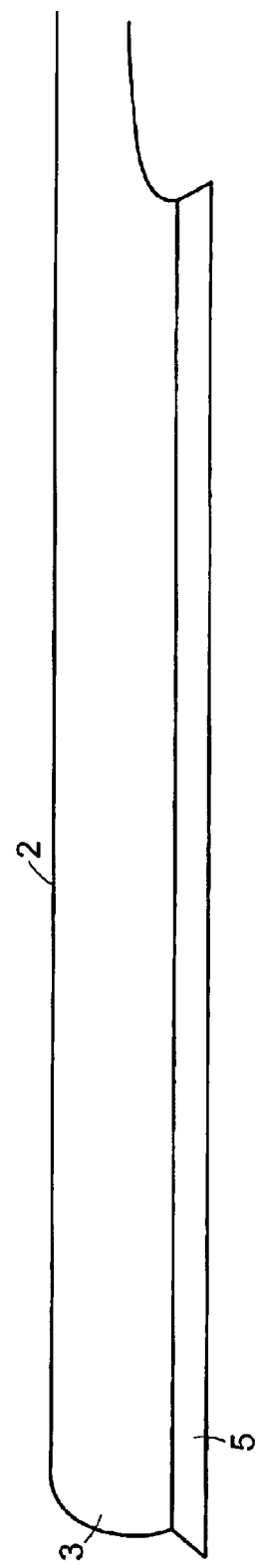
FIG. 27
FIG. 28

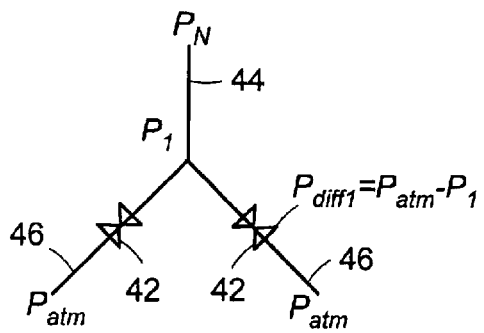
FIG. 35  $P_N < P_1 < P_{atm}$
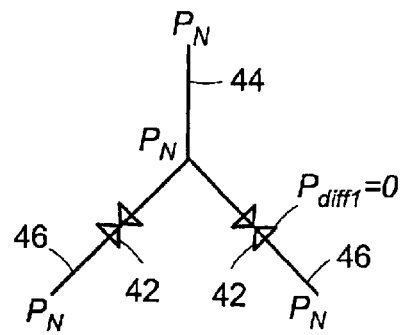
FIG. 36
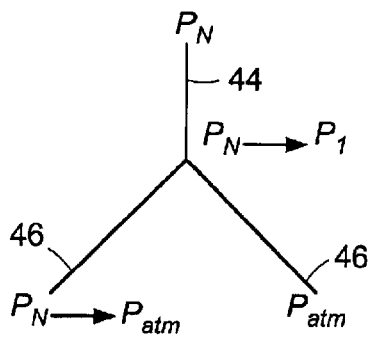
FIG. 37A
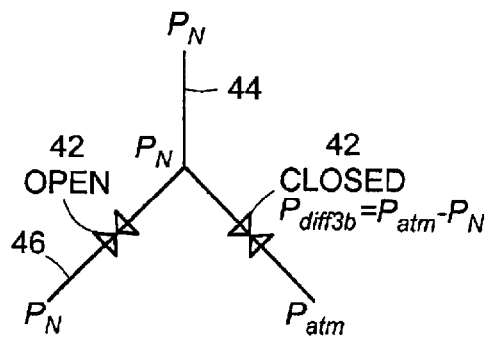
FIG. 37B
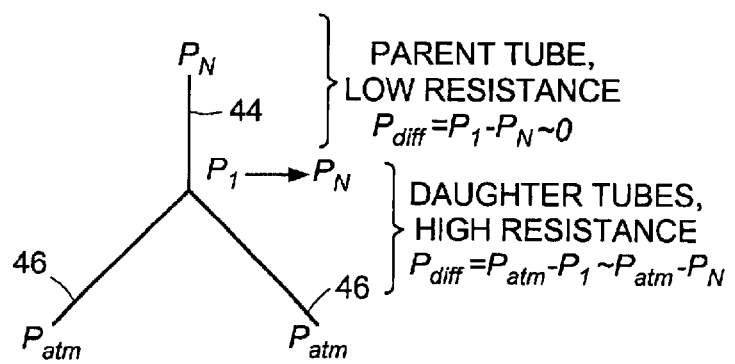
FIG. 38

DEVICE AND METHOD FOR THE MANIPULATION OF ORGANS

FIELD OF THE INVENTION

The present invention relates to a medical device. More particularly, the present invention relates to a manipulation device that can be attached to the heart and other organs of the body so that the organs can be positioned, lifted, turned and held in place during diagnosis, testing, treatment and surgical procedures on the organs.

BACKGROUND OF THE INVENTION

During various surgical procedures, it is often desirable to move, position, lift, turn and hold various organs in place. In many circumstances, this can be done manually. However, organs are generally difficult to securely grasp and manipulate manually due to the slippery nature of the surface of organs. Thus, with such manual manipulation, there is a risk that the organ will be dropped.

What is needed is a device that can be used to securely grasp an organ so that the organ can be moved, positioned, lifted, turned and held in various positions during a surgical procedure. What is further needed is a device that minimizes the risk of dropping the organ during such manipulation. In particular, it would be desirable to provide a device that incorporates a backup mechanism for holding the organ in case the device's primary mechanism holding the organ fails. Further, it would be desirable to provide a single multi-use device that can be used interchangeably on all of the various organs of the body.

SUMMARY OF THE INVENTION

The present invention provides a novel device for use during medical procedures. More particularly, the present invention relates to a manipulation device that adheres to an organ and is used to easily lift, position, turn, move, and hold the organ in place during various procedures on the organ or during various procedures near the organ (e.g. a site obstructed by the organ). The manipulation device may provide beneficial effects for use on various organs of the body including, for example, the heart, kidneys, liver, etc.

The manipulation device is particularly suitable not only for use on various organs, but can also be used to attach to various surfaces of an organ. For example, a single device can be used to adhere to any ventricular surface (when used for cardiac manipulation), including broad anterior surfaces and narrow obtuse marginal surfaces including, for example, the apex or the obtuse margin "OM".

In an exemplary embodiment, the device includes a housing having a top surface and side portions that extend downwards from the top surface. The device may further include one or more flanges extending from the side surfaces or replacing the side portions and extending directly from the top surface. In some embodiments, the one or more flanges contact and adhere to the organ. Alternatively, the side portions may contact and adhere to the organ. The device may further include a source of differential pressure (e.g. a vacuum, syringe, squeeze bulb or wall vacuum) that aids the device in securely adhering to the organ. In preferred embodiments, the differential pressure source generates a pressure that's less than atmospheric. As used herein, "adhere" is defined as temporary attachment that is under user control.

In one embodiment, the top surface of the housing has an overall bowtie shape, with the top surface narrowing and tapering inwards to its center. In this embodiment, side portions extend downwards from the bowtie shaped top surface to form an opening that is bowtie-shaped.

In another embodiment, the top surface has an overall elliptical shape, with the top surface narrowing and tapering inwards towards its ends or remaining the same or substantially the same width from the center towards its ends. In this embodiment, side portions extend downwards from the elliptical shaped top surface to form an opening that is elliptically shaped.

In another embodiment, the top surface has an overall cross-like shape. In this embodiment, side portions extend downwards from the cross shaped top surface to form an opening that is cross-shaped.

In another embodiment, the top surface has an overall modified cross-like or multi-arm shape. In this embodiment, side portions extend downward from the multi-arm shaped top surface to form an opening that is multi-arm shaped.

In another embodiment, the housing has a cup-like shape. The cup shaped housing may have a variety of geometries such as, for example, circular, oval, square, triangular, rectangular, etc.

In another embodiment, the housing has a flat, elongate shape comprising a flat, elongate top surface and side portions extending downwards from the top surface. In one embodiment, the bottom of the elongate housing is open. In another embodiment, the elongate housing further includes a bottom surface. The bottom surface may include one or more flanges which contact and adhere to the organ. In some embodiments, one or more apertures are located in the bottom surface through which a differential pressure may be applied to assist the device in adhering to an organ. One or more flanges may be positioned around each of the apertures for further enhancing the device's grip on the organ.

In each of these embodiments, preferably in embodiments wherein the housing is used in connection with a differential pressure source, the bottom of the top surface may further include protrusions or ribs along its surface. The protrusions or ribs are designed to prevent the organ from becoming pulled into the one or more apertures through which the differential pressure source is introduced, which may lead to organ damage and blockage of the differential pressure source.

In some embodiments, preferably in embodiments wherein the housing is used in connection with a differential pressure source, a screen, an air permeable material (e.g. a foam-like member), or a similar mechanism is located within the housing to allow passage of differential pressure while preventing the organ from becoming pulled into the one or more apertures through which the differential pressure source is introduced, which may lead to organ damage and blockage of the differential pressure source.

During use, the housing is brought into contact with the surface of the organ. In some embodiments, the side portions contact and adhere to the organ. In other embodiments, the one or more flanges contact and adhere to the organ. In yet other embodiments, the bottom surface of the housing contacts and adheres to the organ. When used, a differential pressure source aids the device in securely grasping the organ. As the housing is brought into contact with the surface of the organ, the user may manipulate and shape the housing as desired to properly contact the surface of various organs. In preferred embodiments, the housing is designed to flatten on the surface of the organ, thereby increasing the surface area of the housing on the organ surface and, thus, the grip of the device on the organ surface. Once the organ is securely gripped by the housing, the organ can be lifted, turned, moved and held in various positions so that a medical practitioner can perform various diagnostic procedures, tests, treatments and surgical procedures on the organs. The device can be held and manipulated manually. In a preferred embodiment, the housing is fastened to a holding mechanism in the surgical field, e.g. a retractor or similar device, which assists in manipulating the organ and holding the organ in a desired position.

Other aspects and embodiments of the invention are discussed below.

BRIEF DESCRIPTION OF THE DRAWINGS

For a fuller understanding of the present invention, reference is made to the following detailed description taken in conjunction with the accompanying drawing figures wherein like reference characters denote corresponding parts throughout the several views and wherein:

FIG. 21a shows a lower side perspective view of another embodiment of the cup shaped housing having an inner flange and an outer flange.

FIG. 21b shows a lower side perspective view of another embodiment of the cup shaped housing having an inner side portion and an outer side portion.

FIG. 22 shows a side cross-sectional view of the cup shaped housing of FIG. 21.

FIG. 25 shows an upper side perspective view of one embodiment of the elongate housing.

FIG. 26 shows a bottom perspective view of the elongate housing of FIG. 25.

FIG. 27 shows a bottom view of another embodiment of an elongate housing having an outer flange and one or more apertures in the bottom surface of the housing.

FIG. 28 shows a side view of another embodiment of an elongate housing having an outer flange.

FIG. 35 shows a source of differential pressure schematic wherein one parent tube leads to two daughter tubes. This schematic shows a represents the "open" condition in which neither aperture has established a vacuum seal.

FIG. 36 shows the schematic of FIG. 35 in a "closed" condition.

FIG. 37a shows the schematic of FIG. 35 in a failure condition in which there are no in-line valves and one seal fails and exposes that branch of tubing to atmospheric pressure.

FIG. 37b shows the failure condition of FIG. 37a, with in-line valves in place.

FIG. 38 shows a schematic wherein airway resistance is used to control pressure by use of a parent tube having very low resistance to flow and two daughter tubes having a very high resistance to flow.

DETAILED DESCRIPTION OF THE INVENTION

Figure 1:
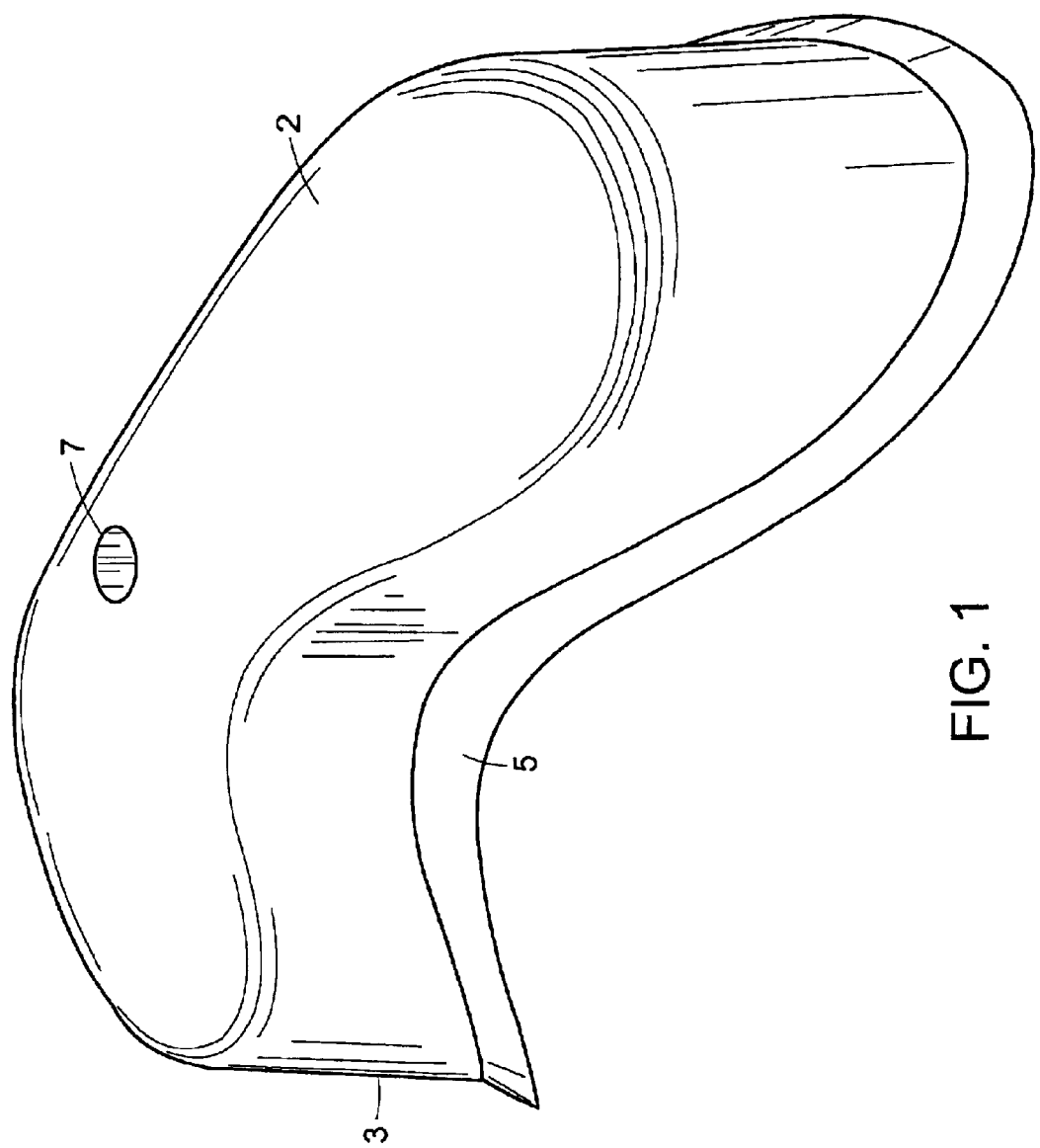
FIG. 1 shows an upper side perspective view of one embodiment of the bowtie shaped housing.

Although the devices of the present invention are primarily illustrated in connection with use on the heart, it will be appreciated by those skilled in the art that such devices may also be used on other organs of the body.

Referring now to the various figures of the drawing, wherein like reference characters refer to like parts, there is shown various views of a device in accordance with the invention.

Figure 5:
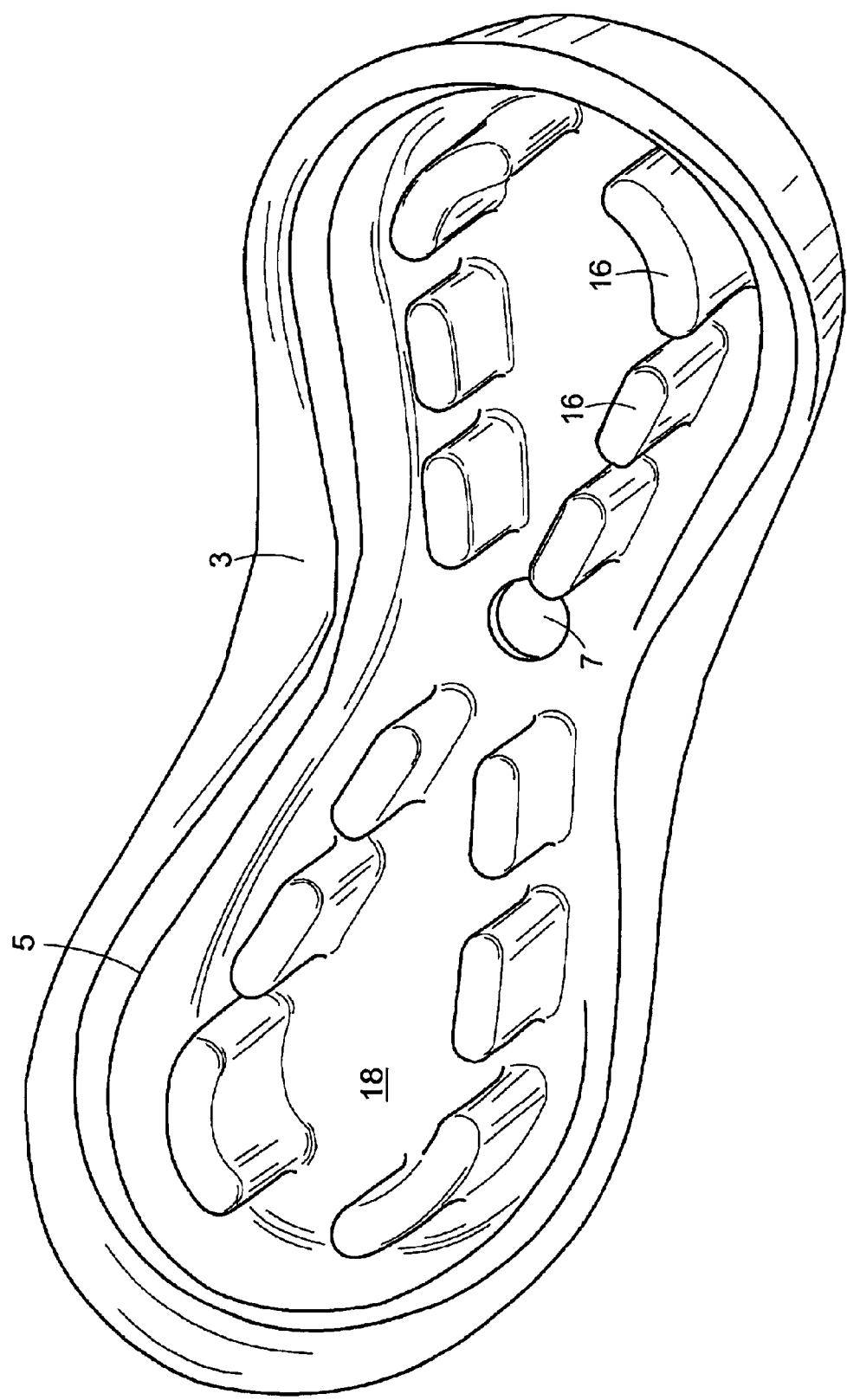
FIG. 5 shows a bottom perspective view of another embodiment of the bowtie shaped housing having ribs or protrusions within the housing.
Figure 6:
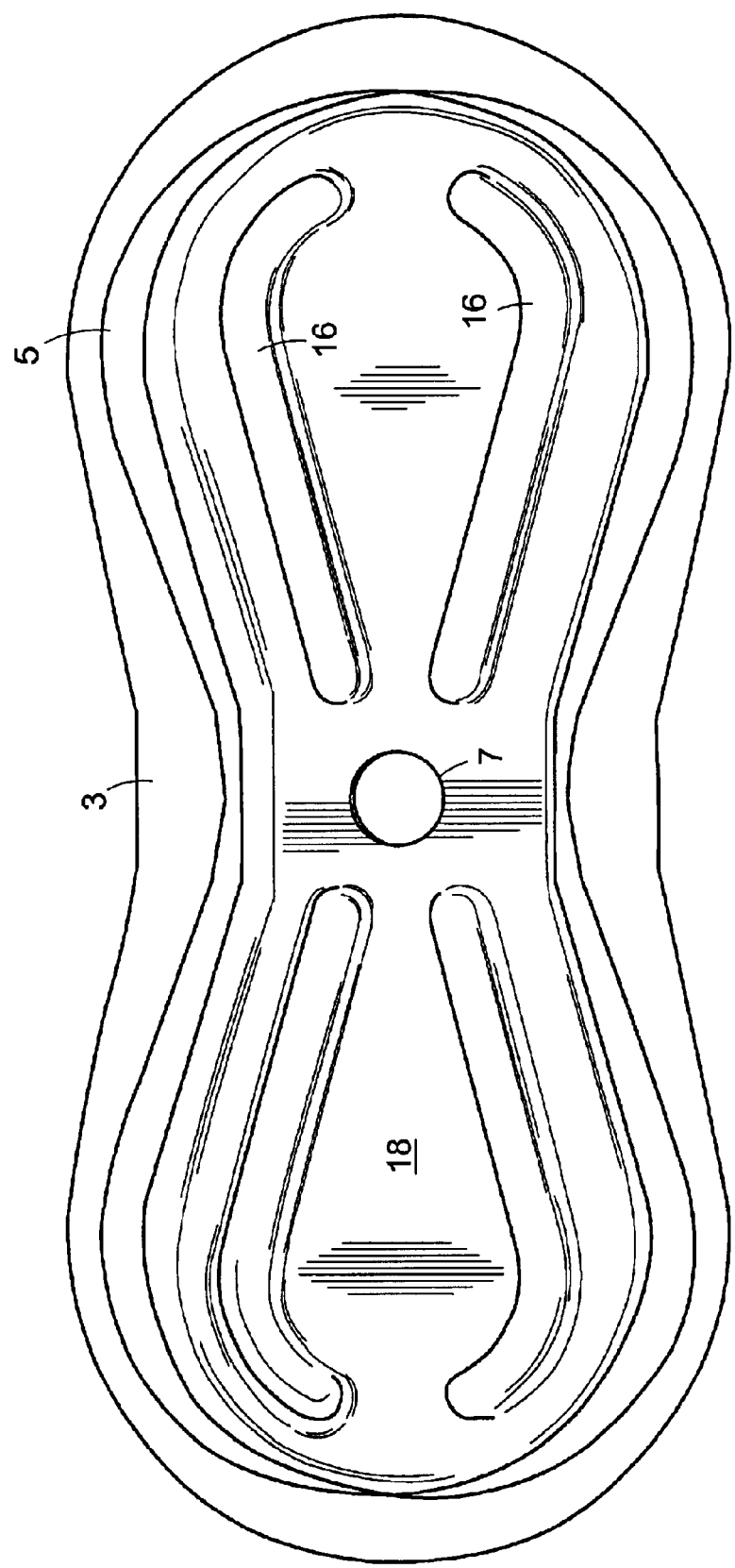
FIG. 6 shows a bottom perspective view of another embodiment of the bowtie shaped housing having ribs or protrusions within the housing.
Figure 29:
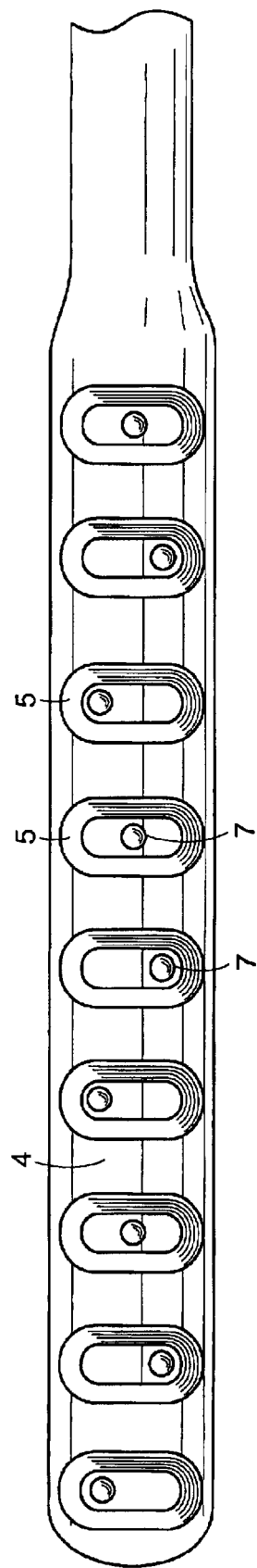
FIG. 29 shows a bottom view of another embodiment of the elongate housing having a plurality of apertures in the bottom surface each surrounded a flange.
Figure 30:
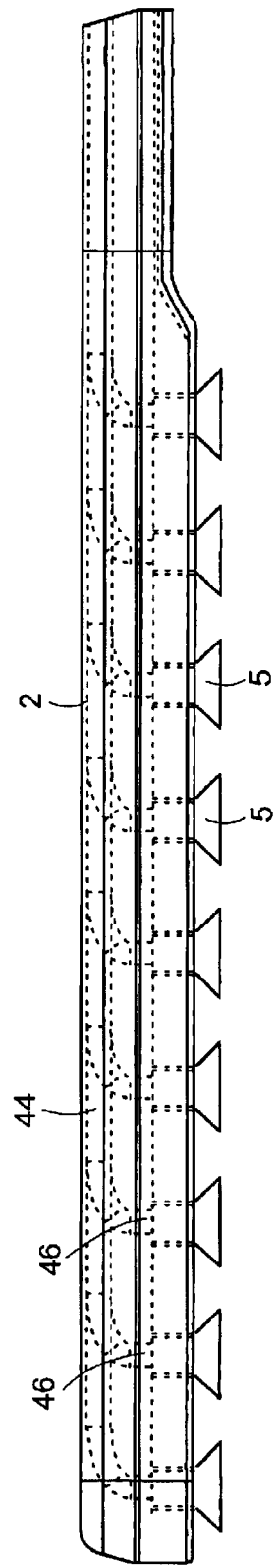
FIG. 30 shows a side view of another embodiment of the elongate housing having a plurality of flanges each connected to a source of differential pressure through daughter and parent tubes.

As shown in the Figures, the device includes a housing 1 having a top surface 2. In some embodiments, the housing further includes side portions 3 extending downwards from the top surface 2. The bottom of the housing can be open, as shown in FIG. 5. In other embodiments, as shown in FIG. 29, a bottom surface 4 covers at least a portion of the bottom of the housing 1.

Figure 7:
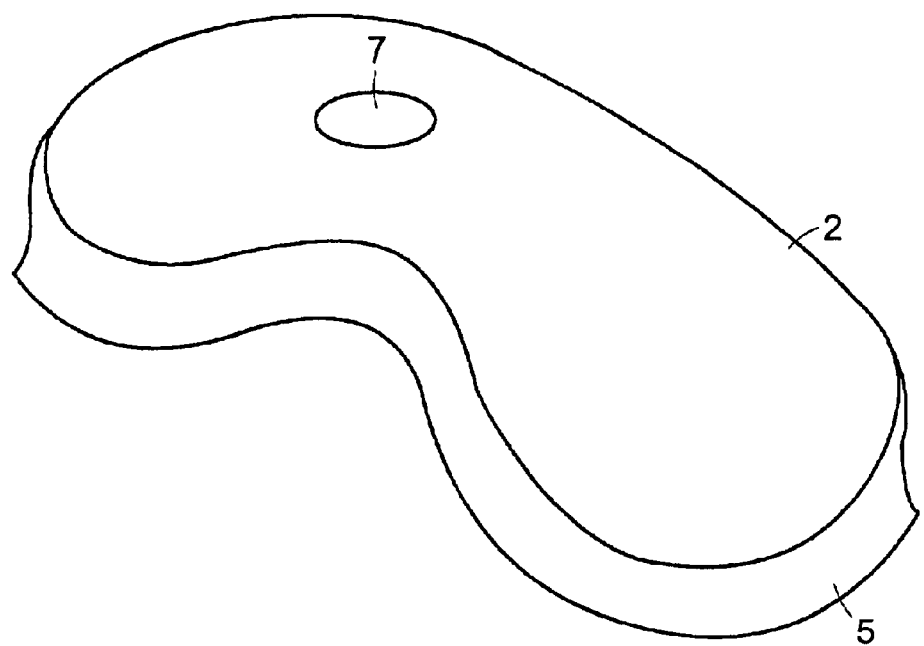
FIG. 7 shows an upper side perspective view of another embodiment of the bowtie shaped housing having a flange replacing the side portions.
Figure 8:
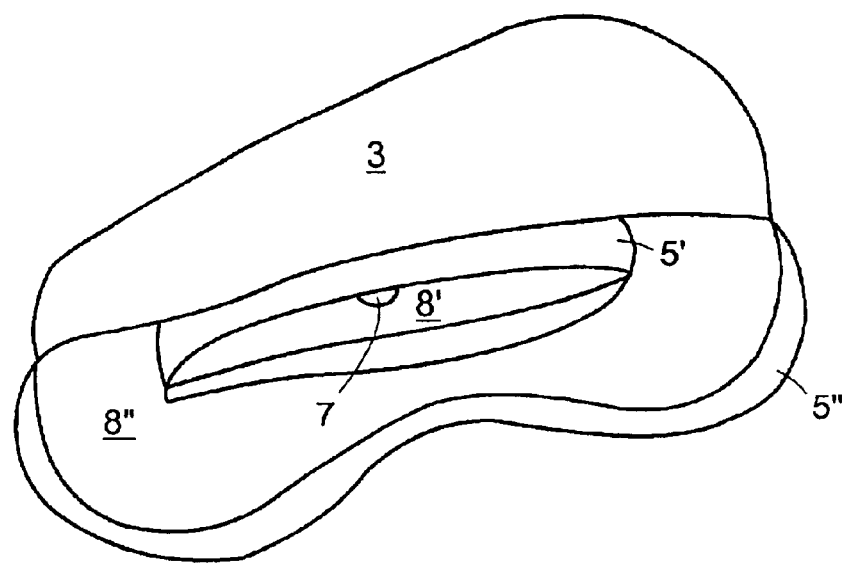
FIG. 8 shows a bottom side perspective view of another embodiment of the bowtie shaped housing having an inner and outer flange.

The device may further include one or more flanges 5. In some embodiments, the one or more flanges 5 extend from the side portions 3, for example, as shown in FIGS. 1, 3, 11 and 16–18. In other embodiments, the one or more flanges 5 replace the side portions 3 and extend downwards directly from the top surface 2, for example, as shown in FIG. 7. In some embodiments, the one or more flanges 5 may line the inside or outside of the side portions 3 and extend downwards past the side portions 3, thereby providing enhanced stability. In some embodiments, the one or more flanges 5 line the inside or outside of the top surface 2, the side portions 3 and extend downwards past the side portions 3. In embodiments, wherein the device includes a bottom surface 4, the one or more flanges 5 can also extend from the bottom surface 4, for example, as shown in FIGS. 25–28. In each of these embodiments, the housing 1 and the one or more flanges 5 can be connected to each other by any suitable means such as, for example, overmolding the housing 1 and the flanges 5 or, for example, bonding the housing 1 and the flanges 5 together using various types of adhesives including, for example, loctite, solvent bond (cyclohexanone) and GE RTV 118 (a silicone adhesive supplied by GE Silicones). In some embodiments, GE RTV 118 is particularly preferable because it remains compliant after curing, and because it is one of the few adhesives that works on silicones, which may be used in fabricating portions of the housing 1.

In some embodiments, the housing 1 and one or more flanges 5 are formed of a unitary structure. In this embodiment, the device can be formed without requiring the use of adhesives or other connection means between the housing 1 and the one or more flanges 5. Further, the possibility that the flanges 5 and housing 1 will become separated from each other is eliminated.

During use, a portion of the housing 1 contacts and adheres to the organ. The portions of the housing 1 that contact and adhere to the organ are preferably designed to prevent trauma when contacting the organ. The portions of the housing 1 that contact and adhere to the organ are also preferably fabricated to allow the user to shape the portions to fit the contours of various organs and to maximize adherence of the device to the organ. In general, the portions of the housing 1 that contact and adhere to the organ (e.g. the one or more flanges 5 and/or side portions 3) are fabricated of flexible, compliant, biocompatible materials. Such materials are well-known and may include, for example, silicone gel, hydrogel, closed cell foam, thermoplastic elastomers such as santoprene, polyisoprene, and polyurethane, and elastomers such as silicone. Non-flexible materials may be used in parts of the housing where rigidity or strength is required, such as upper portions that do not contact tissue, but must resist vacuum forces (e.g. the housing 1 top surface 2 and side portions 3). These materials may include, for example, ABS, polycarbonate, polysulfone, polypropylene, or polyurethane. Further, the portions of the housing 1 and flanges 5 that contact and adhere to the organ are preferably fabricated with rounded, smooth edges to further minimize trauma.

The device may be used alone or in connection with a vacuum or similar source of differential pressure 6 (e.g. spring-loaded syringe, squeeze bulb, etc.) to aid the device in securely adhering to the organ. In such embodiments, the housing 1 would further include at least one aperture 7 through which the vacuum or similar source of differential pressure 6 would flow through the housing 1 and to the organ. The housing 1 could then be connected to the source of differential pressure 6 via tubing or the like. Preferably, when used in connection with a vacuum or similar source of differential pressure 6, the portion of the housing 1 that contacts and adheres to the organ preferably forms an airtight seal about the organ to maximize the adherence of the housing 1 to the organ.

Figure 9:
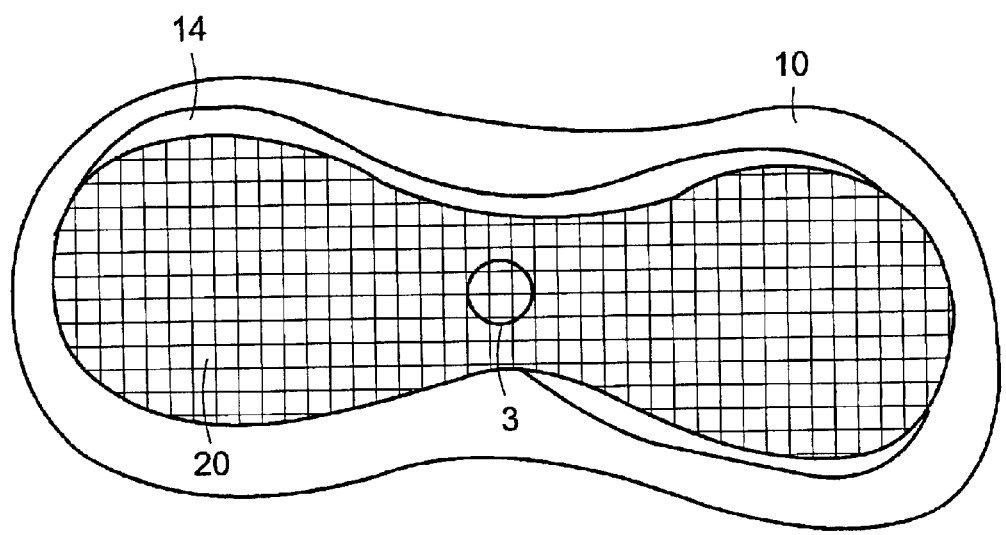
FIG. 9 shows a bottom perspective view of another embodiment of the bowtie shaped housing having a screen within the housing.
Figure 10:
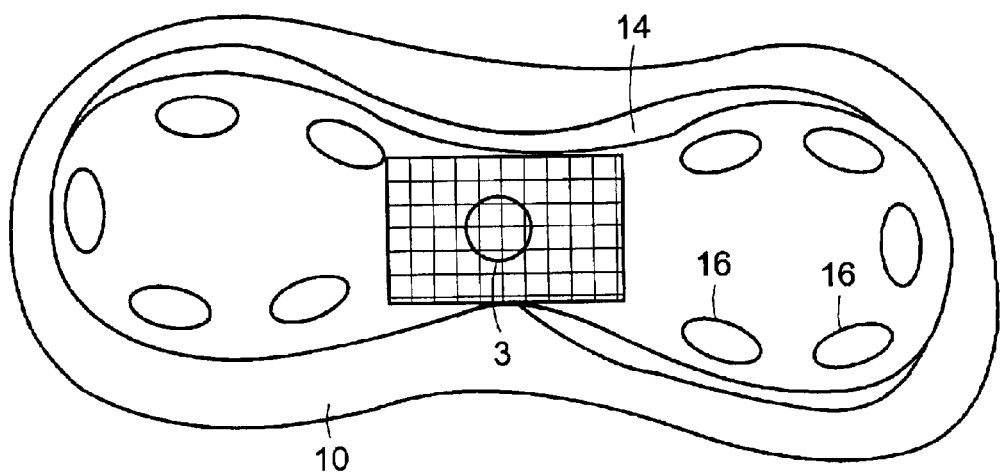
FIG. 10 shows a bottom perspective view of another embodiment of the bowtie shaped housing having a screen and protrusions within the housing.
Figure 11:
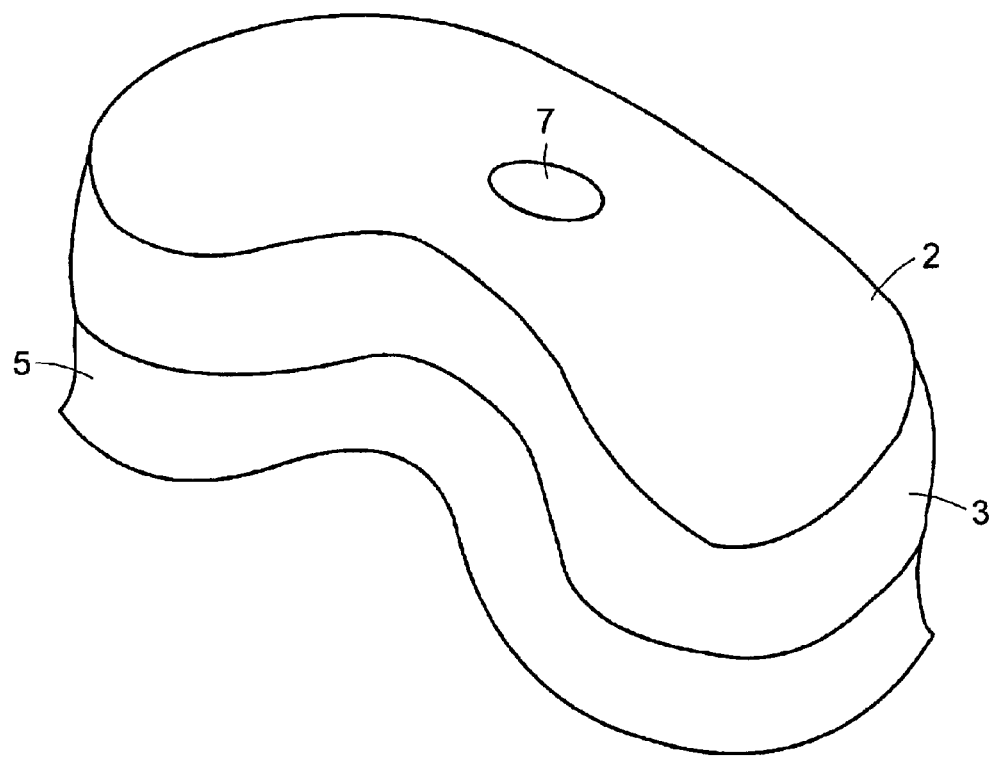
FIG. 11 shows an upper side perspective view of another embodiment of the bowtie shaped housing having straight ends.
Figure 12:
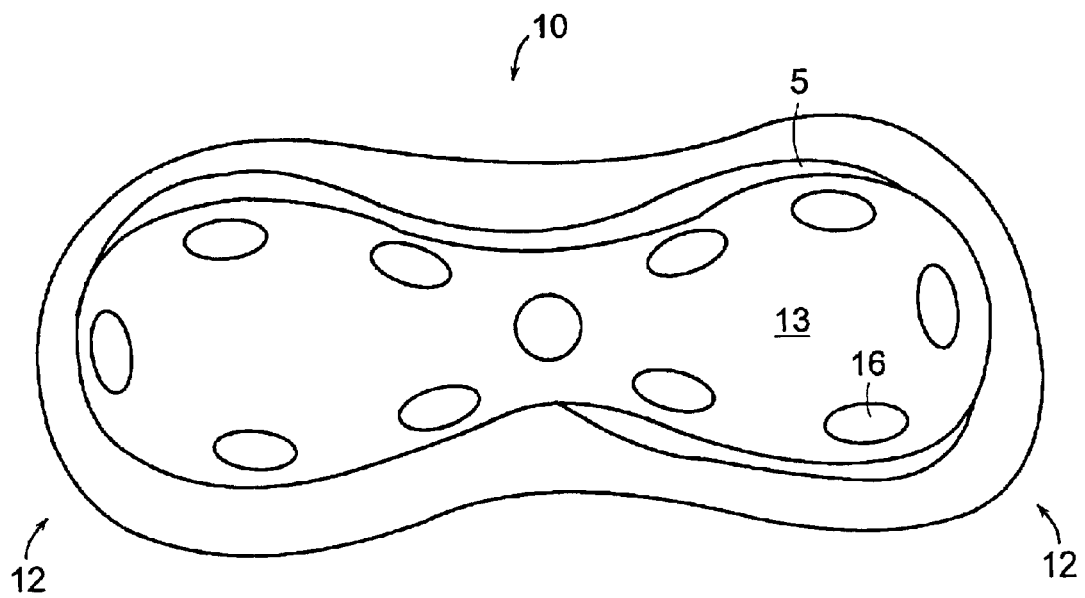
FIG. 12 shows a bottom view a bowtie shaped housing of FIG. 11 having ribs or protrusions within the housing.

In one preferred embodiment, the housing 1 has an overall bowtie-like shape, as shown in FIGS. 1–12, or an overall elliptical-like shape as, shown in FIGS. 45, 47a–b and 50a–d. In the bowtie shaped embodiment, the width of the top surface 2 of the housing 1 narrows as it tapers towards the center 10 of the top surface 2. It is believed that this bowtie shape, when used with a source of differential pressure, distributes the force over a larger area away from a central aperture 7 or vacuum port through which the source of differential pressure flows into the housing. As a result, the maximum lift forces are distributed away from the central region of the device, which can minimize tissue damage resulting from lift forces. In the elliptical shaped embodiment, the width of the top surface 2 of the housing may narrow as it tapers toward the ends 12 of the top surface 2 or it may not taper and may remain substantially the same width from the center 10 to the ends 12 of the top surface. The elliptical shape, it is believed, promotes flattening of the device against the organ during use. In each embodiment, the ends 12 of the top surface 2 may be straight, as shown in FIGS. 11 and 12, or rounded, as shown in FIGS. 1–10. The shapes of the elliptical and bowtie housings make it particularly easy to apply these devices to the various surfaces of various organs. Further, the elliptical and bowtie housings potentially occupy little space in the surgical field on account of their narrow dimensions.

Side portions 3 preferably extend downwards along the circumference of the top surface 2 of the bowtie or elliptical shaped housing 1. The bottom of the bowtie or elliptical shaped housing 1 is preferably open, with the side portions 3 and the top surface 2 forming a bowtie shaped or elliptical shaped opening 8.

Figure 2:
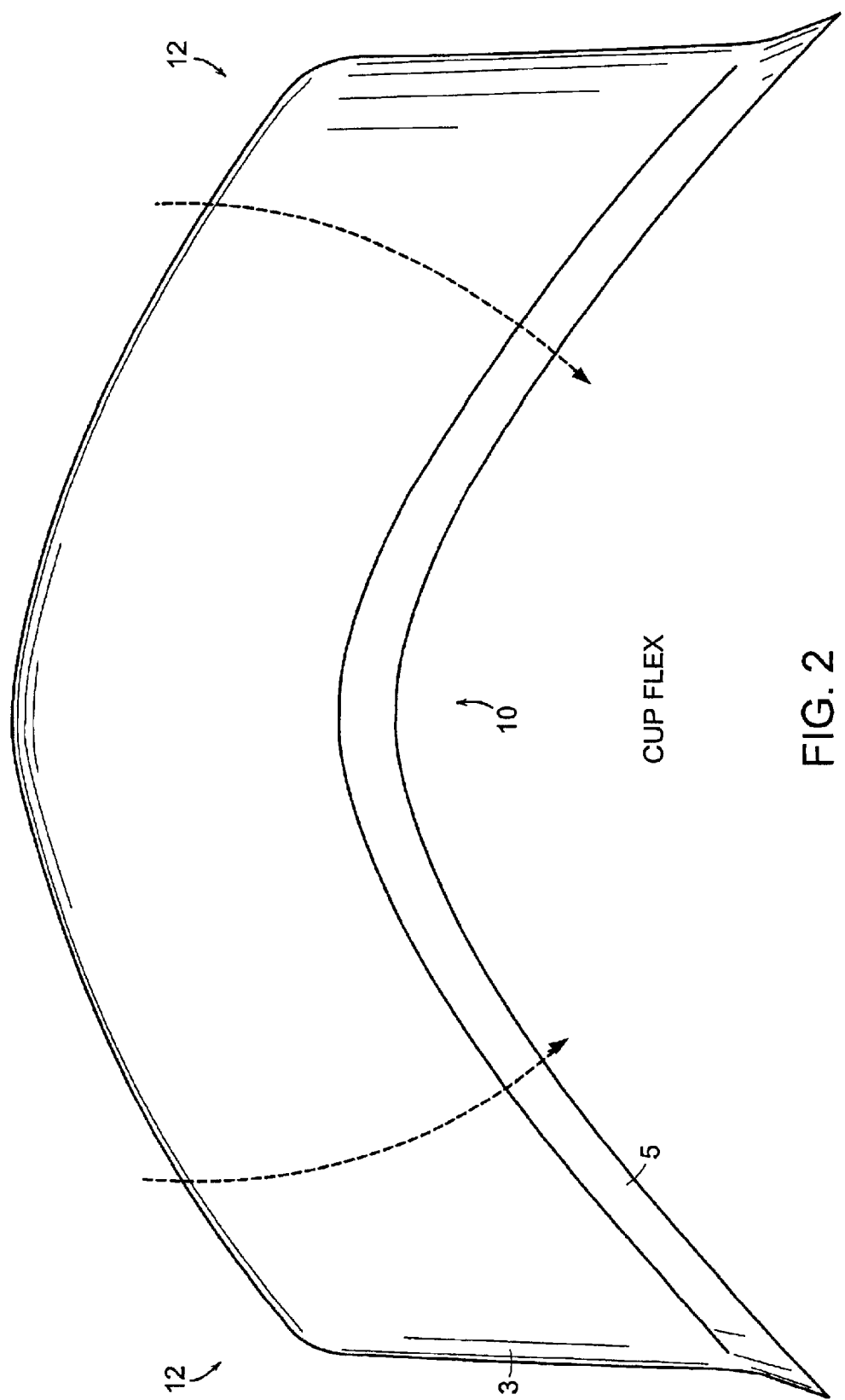
FIG. 2 shows a side view of the bowtie shaped housing of FIG. 1 and further shows how the sides of the bowtie shaped housing may flex inwards.
Figure 3:
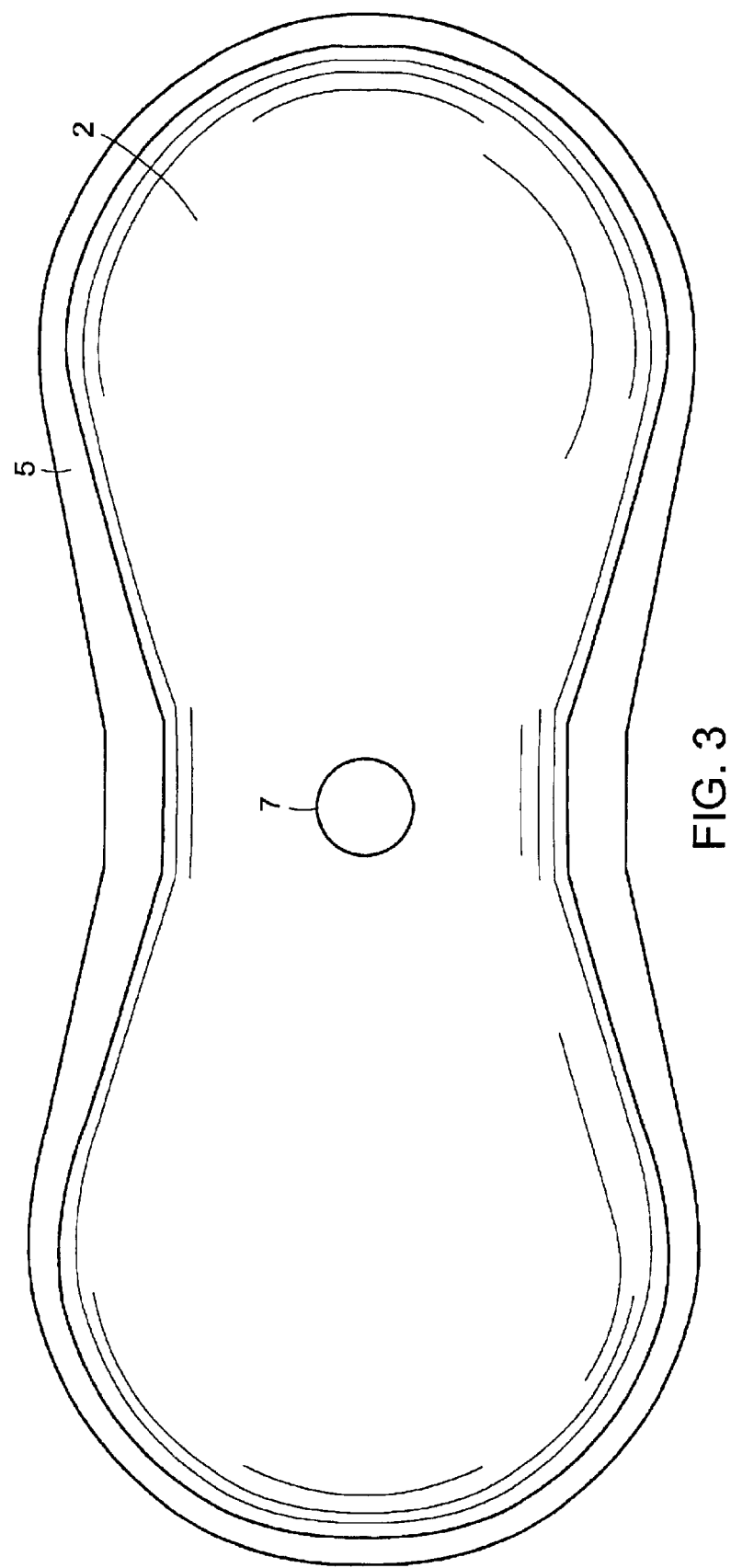
FIG. 3 shows a top perspective view of the bowtie shaped housing of FIG. 1.
Figure 4:
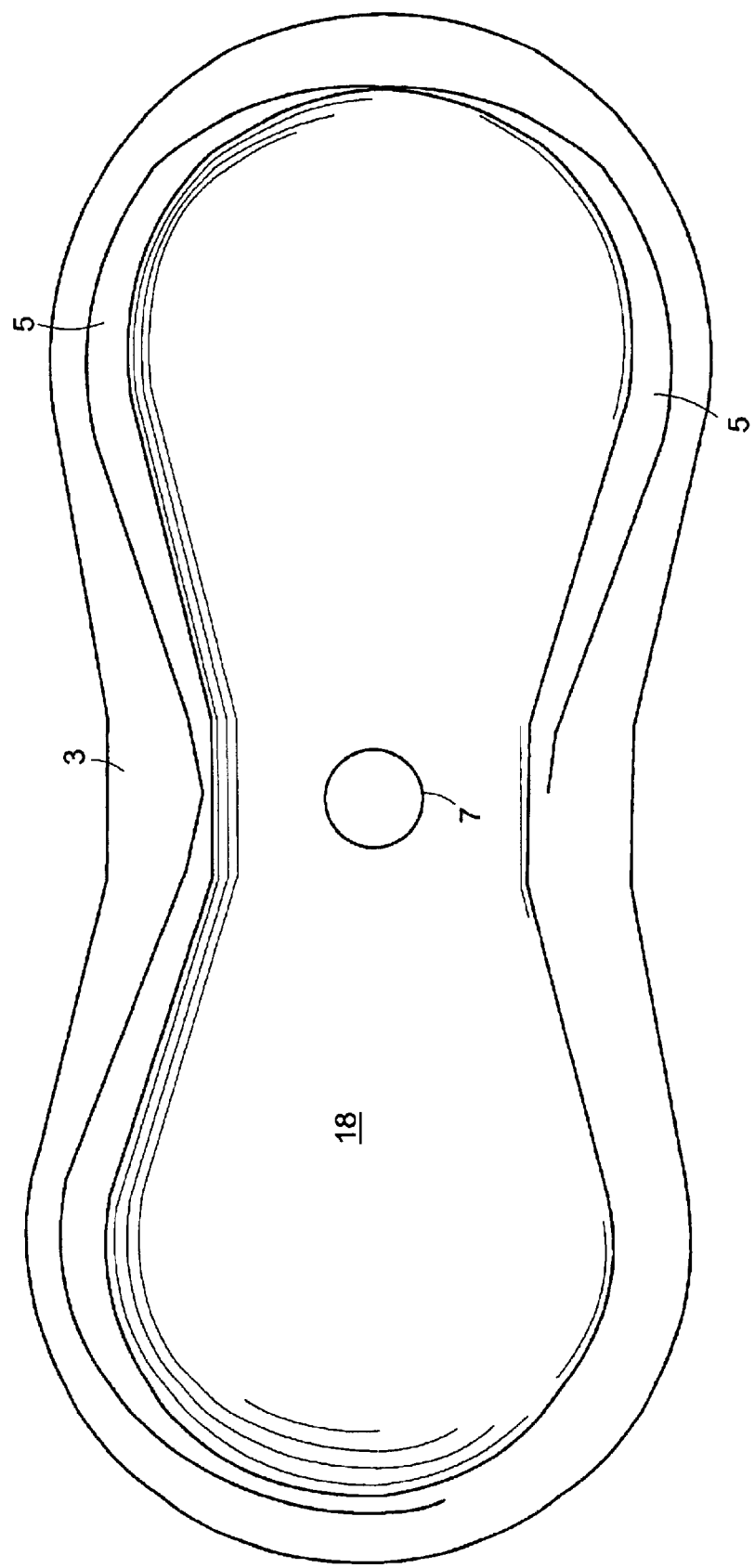
FIG. 4 shows a bottom perspective view of the bowtie shaped housing of FIG. 1.

In some embodiments, the bowtie or elliptical shaped housing 1 further includes one or more flanges 5 located about the portion of the housing 1 that contacts and adheres to the organ. The one or more flanges 5 assists in securely adhering the device to the organ. In one embodiment, for example, as shown in FIGS. 1 and 2, the one or more flanges 5 extend from the side portions 3, preferably along the entire lengths of the side portions 3. In another embodiment, for example, as shown in FIG. 7, the one or more flanges 5 replace the side portions 3 and extend directly from the top surface 2 of the bowtie or elliptical shaped housing 1.

During use, in embodiments excluding the one or more flange 5, the side portions 3 contact and adhere to the organ. In other embodiments, wherein the housing includes one or more flanges 5, the one or more flanges 5 contact and adhere to the organ.

In another preferred embodiment, the housing 1 has an overall cross-like shape, as shown in FIGS. 47c and 49a–d. In general, the top surface 2 of the cross shaped housing 1 has four ends 12. For example, as shown in FIGS. 47c and 49a–d, the cross shaped housing 1 is formed of two intersecting elliptical shaped portions. The cross shaped housing can also be formed of two intersecting bowtie shaped portions and other shaped portions which form four ends 12. Further, the intersecting portions may be the same size or sized differently, for example, as shown in FIGS. 47c and 49a–d, one elliptical shaped portion can be larger than the other elliptical shaped portion. In each embodiment, the ends 12 of the top surface 2 may be straight, or rounded.

Figure 60A:
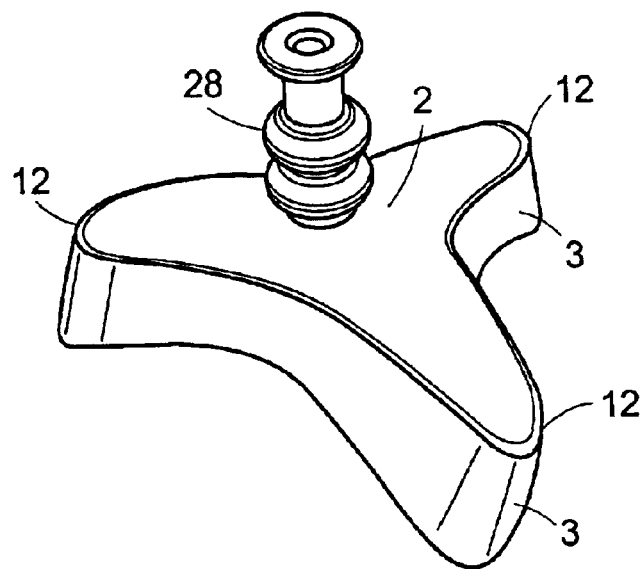
FIGS. 60a–b show modified cross shaped, multi-arm housings having three and five arms.
Figure 60B:
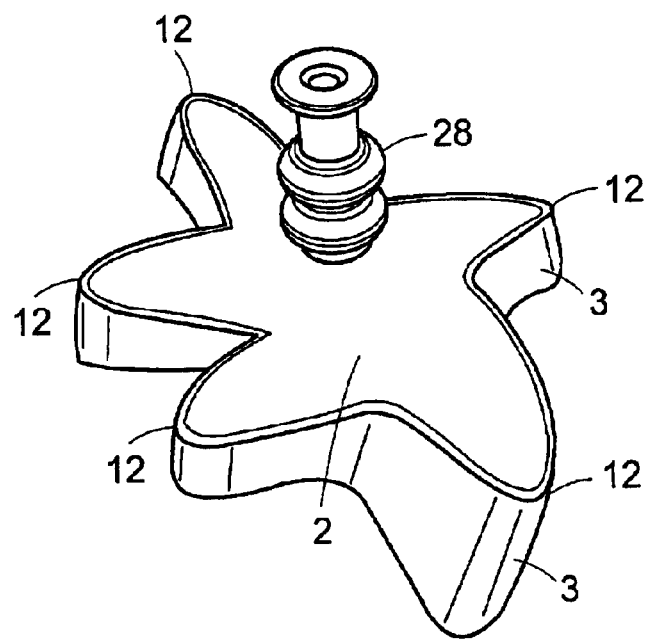

In another embodiment the cross-shaped housing 1 is modified to include different numbers of ends or "arms" 12, for example, three armed, five armed, six armed, etc. star-like shaped housings may be used. Examples of such multi-arm shaped housings are shown in FIGS. 60a–b. In each embodiment, the ends or arms 12 of the top surface 2 may be straight or rounded.

Side portions 3 preferably extend downwards along the circumference of the top surface 2 of the cross and multi-arm shaped housings 1. The bottom of the cross and multi-arm shaped housings 1 is preferably open, with the side portions 3 and the top surface 2 forming a cross and multi-arm shaped opening 8.

In some embodiments, the cross and multi-arm shaped housing 1 further includes one or more flanges 5 located about the portion of the housing 1 that contacts and adheres to the organ. The one or more flanges 5 assists in securely adhering the device to the organ. In one embodiment, the one or more flanges 5 extend from the side portions 3, preferably along the entire lengths of the side portions 3. In other embodiments, the one or more flanges 5 can replace the side portions 3 and extend directly from the top surface 2 of cross and multi-arm shaped housing 1.

Figure 18:
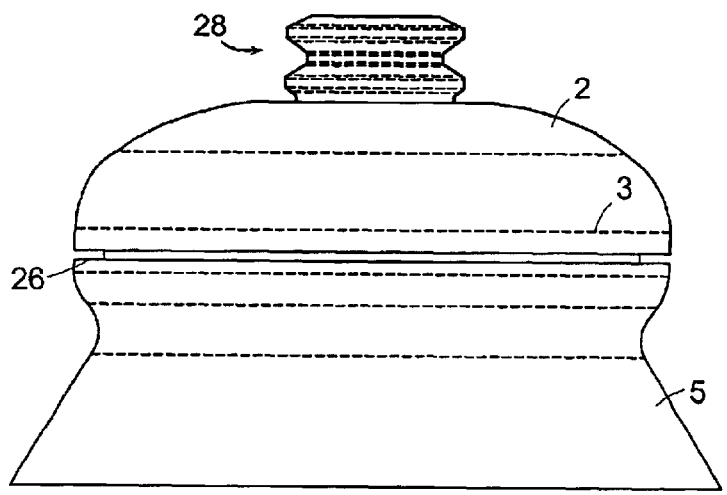
FIG. 18 shows a side view of the cup shaped housing of FIG. 16.
Figure 19:
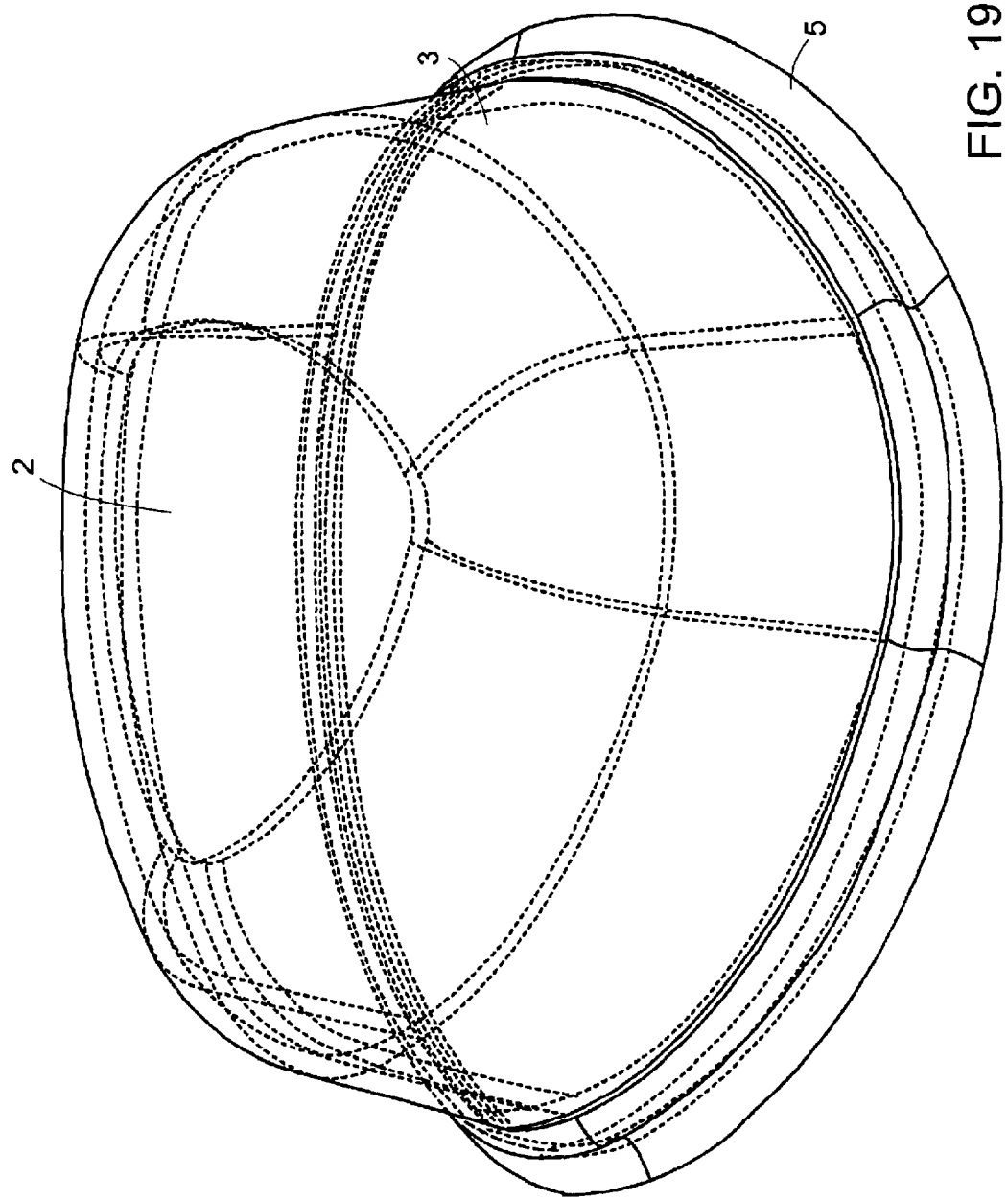
FIG. 19 shows a lower side perspective view of another embodiment of the cup shaped housing having a triangular geometry.
Figure 20:
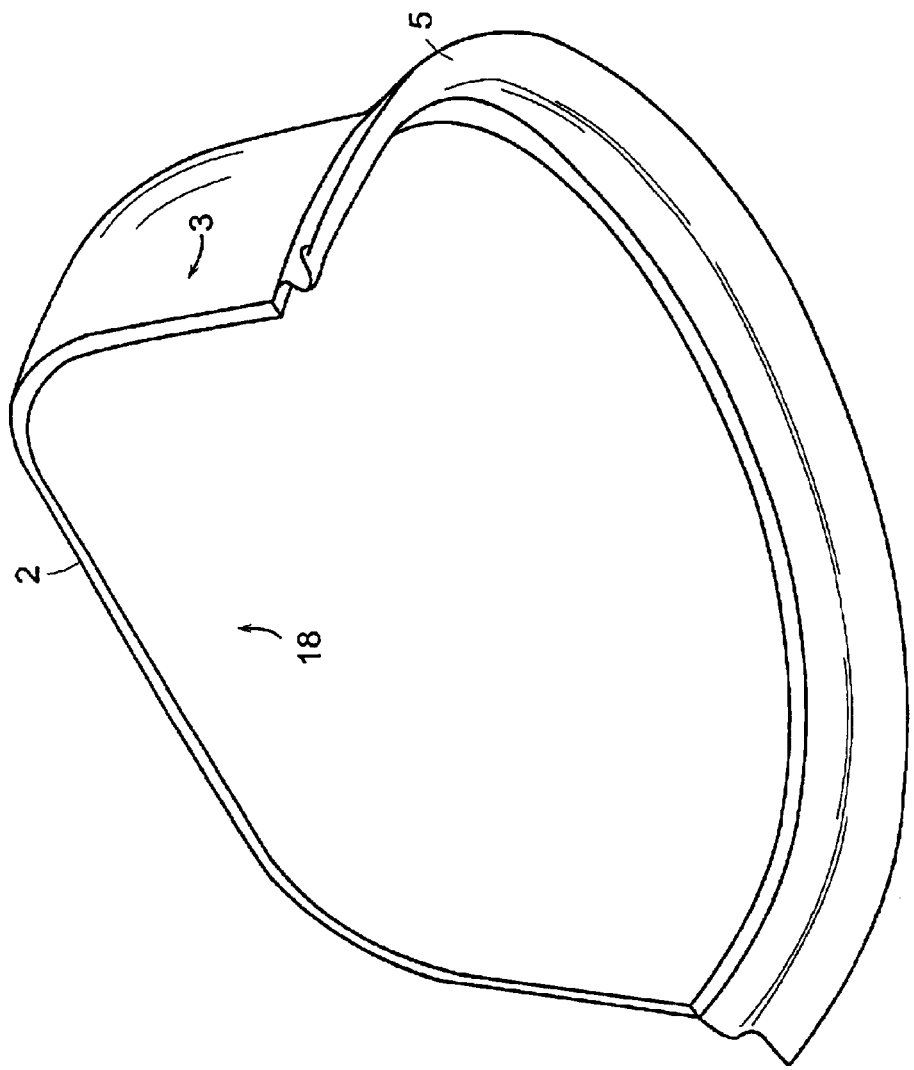
FIG. 20 shows a lower side cutaway view of the triangular cup shaped housing of FIG. 19.
Figure 23:
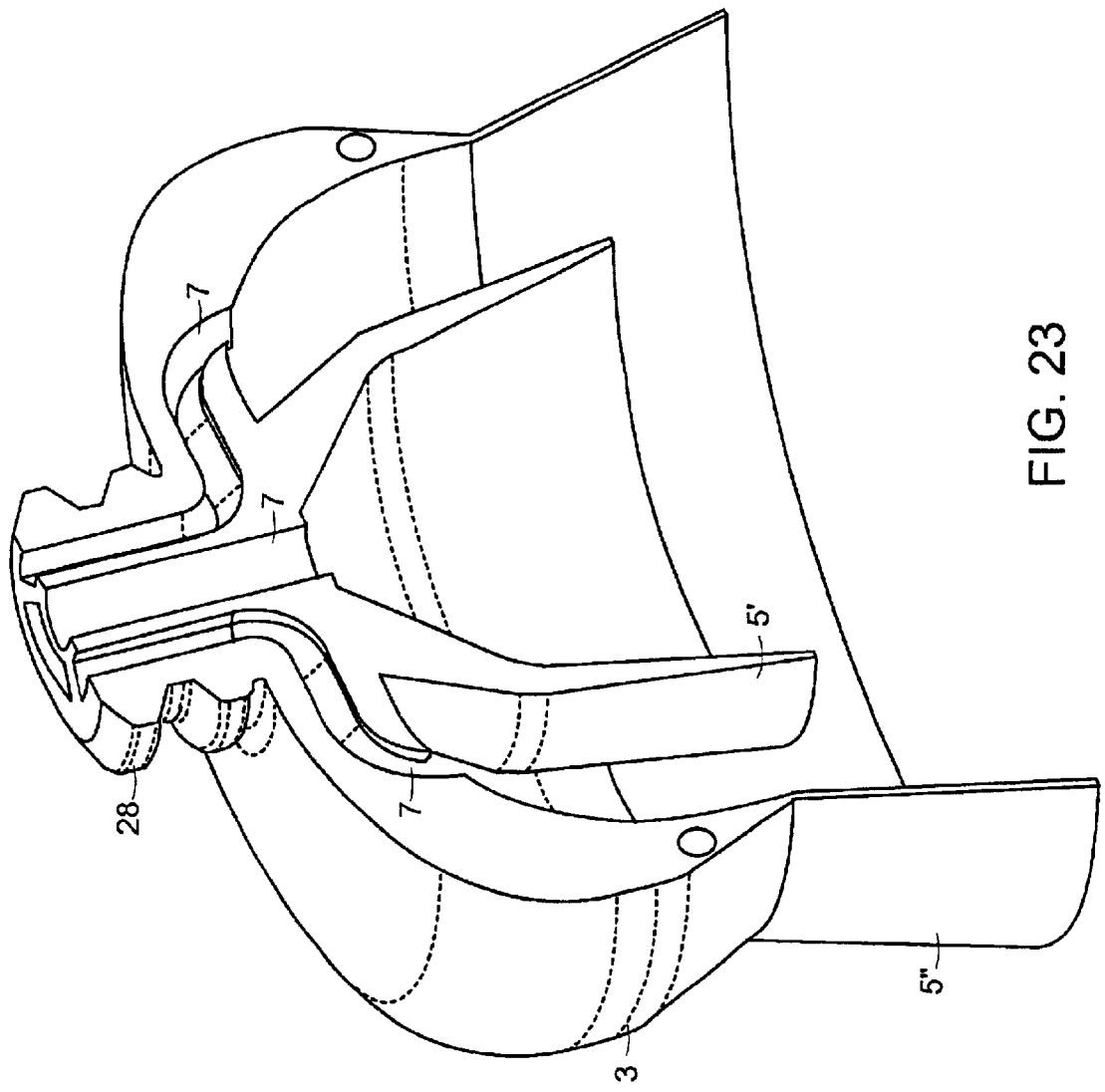
FIG. 23 shows a side cutaway view of the cup shaped housing of FIG. 21.
Figure 24:
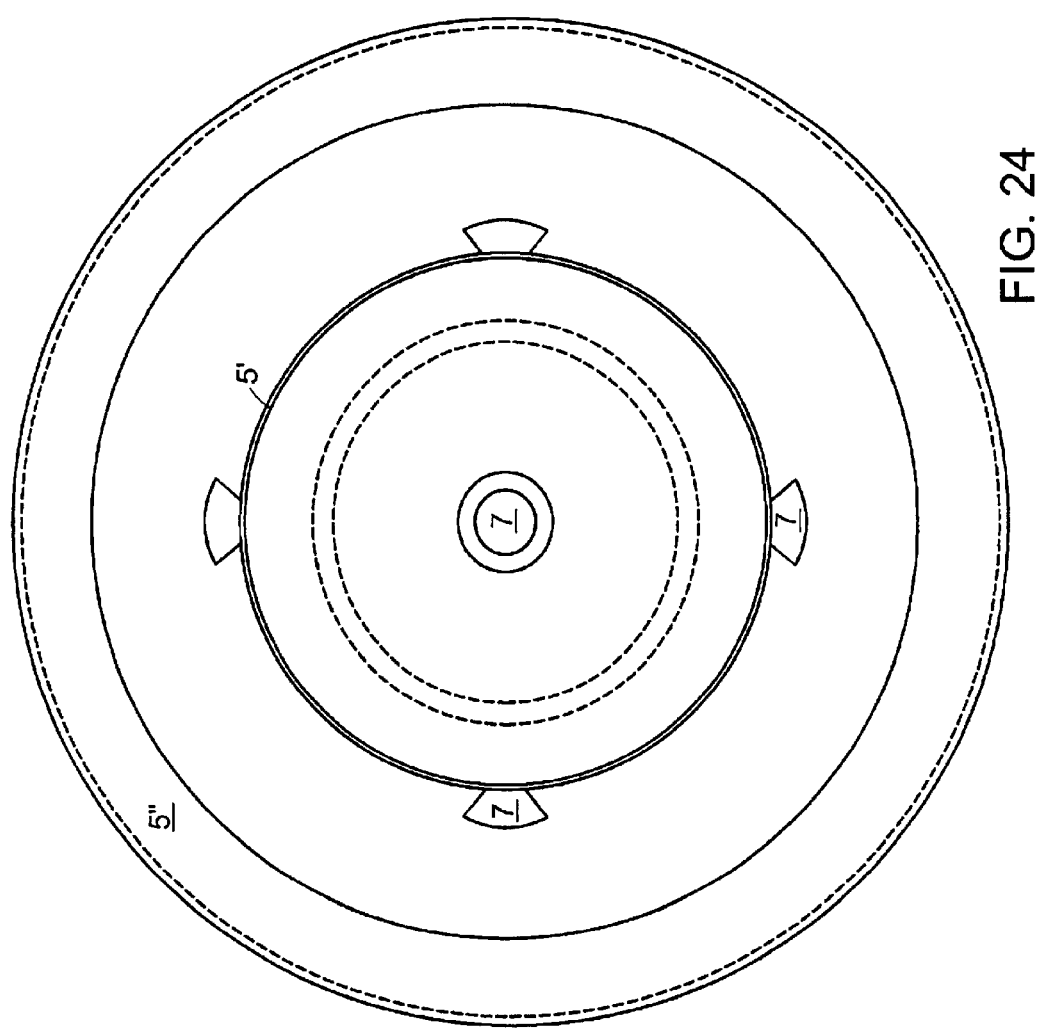
FIG. 24 shows a bottom view of the cup shaped housing of FIG. 21.

In another embodiment, as shown in FIGS. 16–24 the housing 1 has a cup-like shape. The cup shaped housing has a top surface 2 and side portions 3 extending downwards, preferably along the entire circumference of the top surface 2. The top surface 2 can have a variety of geometries, e.g. circular, oval, square, triangular, etc. As shown in FIGS. 16–18 and 22, the top surface 2 has a circular geometry. FIG. 19 shows a triangular shaped geometry.

In preferred embodiments, as shown in FIGS. 16–24, the cup-shaped housing 1 preferably further comprises one or more flanges 5 located about the portion of the housing 1 that contacts the organ. The one or more flanges 5 assist in securely adhering the device to the organ. Preferably, the one or more flanges 5 extend from the ends of the side portions 3, preferably along the entire lengths of the side portions 3, as shown in FIGS. 16–21, and 22–24. In some embodiments, the one or more flanges 5 replace the side portions 3, as shown in FIG. 21b.

During use, in embodiments excluding the one or more flanges 5, the side portions 3 contact and adhere to the organ.

In other embodiments, wherein the housing includes one or more flanges 5, the one or more flanges 5 contact and adhere to the organ.

In each of the above embodiments (i.e. the bowtie shaped housing, elliptical shaped housing, cross shaped housing, multi-arm shaped housing and the cup shaped housing), multiple, independent seals may be formed by the housing 1 on the organ surface.

For example, as shown in FIG. 21b in the cup-shaped housing 1, multiple concentric side portions 3 can be included such that each side portion 3 forms an independent seal on the organ. Similar multiple side portions 3 can also be used on the bowtie and elliptical shaped housings 1.

In embodiments wherein one or more flanges 5 are included in the device, multiple independent flanges 5 can be included to form independent seals on the organ, as shown in FIGS. 21a and 22. Thus, if the seal on one or more of the flanges 5 fails, backup seals will maintain secure grip on the organ. In one preferred embodiment, shown in FIGS. 21a and 22, the multiple flanges 5 include an inner flange 5' and at least one outer flange 5", wherein the inner flange 5' forms an inner opening 8' and the outer flange 5" forms an outer opening 8".

In some embodiments, the device is used in connection with a differential pressure source 6. As such, one or more of the openings formed by each side portion 3, as shown in FIG. 21b, or by each flange, e.g. 5', 5" as shown in FIGS. 21a and 22 may be connected to the differential pressure source 6. Thus, each opening may have differential pressure applied to it or, alternatively, only one or some of the openings may have differential pressure applied to them. For example, the inner flange 5' may have at least one aperture 7 through which the vacuum or source of differential pressure 6 would flow into the inner opening 8'. The outer flange 5" may have none, one or more than one aperture 7 through which the vacuum or similar source of differential pressure 6 would flow into the outer opening 8".

In one preferred embodiment, the differential pressure of the inner opening 8' is fed by a central aperture 7, while four outer apertures 7 supply the outer opening 8' with differential pressure. Preferably, independent vacuum lines are utilized to supply the inner and outer openings (a total of 2 vacuum lines). This provides an additional safety feature wherein if one vacuum line fails, the other vacuum line will operate to maintain the device's hold on the organ.

In another embodiment, as shown in FIGS. 25–34, the housing 1 has an elongate shape, preferably elongate and substantially flat. This design lends itself more to cardiac manipulation than to lifting. The housing comprises an elongate top surface 2 and side portions 3 extending downwards from the top surface 2. In some embodiments, the elongate housing 1 further has a bottom surface 4. Preferably, the elongate housing 1 is flexible along its length to allow a user to shape the housing 1 to contact and adhere to various organ surfaces.

In embodiments wherein the elongate housing 1 includes a top surface 2 and side portions 3 extending downwards from the top surface 2, the side portions 3 may contact and adhere to the organ. In some embodiments, the elongate housing 1 may further include one or more flanges 5 extending from the side portions 3 or from the top surface 2. In such embodiments, the one or more flanges 5 may contact and adhere to the organ.

In some embodiments, as shown in FIGS. 27 and 28, the elongate housing 1 includes a top surface 2, side portions 3, a bottom surface 4 and a flange 5 located about the circumference of the bottom surface 4. During use, the flange 5 contacts and adheres the device to the organ.

In some embodiments, as shown in FIGS. 25–26 and 29–33, the elongate housing 1 includes a top surface 2, side portions 3, a bottom surface 4 and a plurality of flanges 5 positioned on the bottom surface 4. The shapes of the plurality of flanges 5 is not particularly limited and may be, for example, oval, square, triangular, etc. During use, the plurality of flanges 5 contact and adhere the device to the organ.

In some embodiments, as shown in FIGS. 27 and 29, the elongate housing 1 includes a top surface 2, side portions 3, a bottom surface 4 and one or more apertures 7 located in the bottom surface 4 through which a differential pressure source 6 may be introduced. As shown, the one or more apertures 7 may be circular in shape. However, the shape of the one or more apertures 7 is not particularly limited and may be, for example, oval, square, triangular, etc. A screen 20 or similar mechanism may further be located within or placed over the apertures 7 to prevent the organ from being pulled into and blocking the differential pressure source 6. Alternatively, rather than a screen 20, a foam, or other material porous to air may be placed in front of the one or more apertures to prevent the organ from becoming pulled into the one or more apertures 7 by the differential pressure source 6. In some embodiments, one or more flanges 5 may further be located about the circumference of the apertures 7, as shown in FIGS. 29–33, to further enhance the adherence of the device to the organ.

Preferably, when used with a differential pressure source and a plurality of apertures, the flat, elongate housing 1 has at least one lumen or tube extending along its length that connects each of the apertures 7 to the differential pressure source 6. Preferably, independent seals are formed by each aperture 7 on the surface of the organ. Thus, if one seal fails, then the other apertures 7 will continue to hold the organ.

In order to make each aperture 7 truly independent, each aperture 7 would require its own source of differential pressure 6 (e.g. a direct, independent connection to wall vacuum for each aperture). If all apertures 7 were supplied by a single source of differential pressure, then a loss of seal at any aperture would expose the entire system to atmospheric pressure, and the differential pressure would be dramatically reduced at all apertures 7. Thus, failure in one aperture would lead to failure in all apertures. On the other hand, if each aperture has its own source of differential pressure, then the loss of the seal at one aperture would not affect the other apertures, and the remaining apertures would maintain their seal and adherence to the organ.

However, it is not always practical to have several independent sources of differential pressure 6. This would require more than one connection to the wall vacuum or other source. Thus, multiple-lumen tubes, or a bundle of tubes, would be required to connect each aperture to the source. This could clutter the surgical field.

Thus, one embodiment uses a single parent tube 44 connected to the source of differential pressure 6 (e.g. vacuum) and multiple daughter tubes 46 (preferably one per aperture) each equipped with an in-line valve 42. Preferably, the in-line valves 42 would prevent atmospheric pressure at one aperture (e.g. if the seal at that aperture fails) from affecting the other apertures.

For example, in the schematic shown in FIG. 35, one parent tube 44 leads to two daughter tubes 46, each daughter tube 46 leading to an aperture This schematic represents the "open" condition in which neither aperture 7 has established a vacuum seal. This is representative of a situation in which the source of differential pressure 6 has been turned on but the device has not yet been applied to the organ surface. The source of differential pressure 6 establishes some differential pressure, $P_N$, and each aperture 7 is exposed to atmospheric pressure, $P_{atm}$. Each independent line contains an in-line valve 42 that is capable of shutting off flow. $P_1$ is the pressure at the tube bifurcation. $P_{diff1}$ is the pressure differential across the valves 42 in this condition.

In the open condition: $P_N < P_1 < P_{atm}$. A simple steady flow analysis in the tubing explains this pressure drop across the valves 42 ($P_1 < P_{atm}$) and toward the source of differential pressure 6 ($P_N < P_1$). A laminar, steady, incompressible, Newtonian flow is assumed. The air flow follows the pressure gradient from $P_{atm}$ to $P_N$.

FIG. 36 shows the "sealed" condition. The apertures 7 have been applied to the organ surface and a vacuum seal has formed at both apertures 7. There is no flow through the tubing 44, 46, so the pressure is essentially consistent throughout the tubing (since the fluid is air, neglect static pressure differentials throughout the tubing). If the seal on one aperture fails, then the valves can help maintain function on the other aperture.

FIG. 37a shows the failure condition in which there are no in-line valves 42. In this case, one seal fails and exposes that branch of tubing to atmospheric pressure. The main branch is exposed to atmospheric pressure, causing the pressure at the bifurcation to approach $P_1$ due to the development of airflow toward the source of differential pressure 6. As the bifurcation pressure approaches $P_1$, the pressure at the remaining apertures drops, and may not be sufficient to maintain the device's hold on the organ. Thus, the remaining aperture's seal is prone to fail.

FIG. 37b shows the same failure condition with in-line valves 42 in place. The valve associated with the aperture that fails closes immediately after aperture failure. Therefore, one side of the closed valve is at $P_{atm}$ and the other side is at $P_N$ (differential pressure across valve $P_{diffN} = P_{atm} - P_N$). The closed valve prevents flow, which maintains the bifurcation and remaining aperture pressure at $P_N$.

The analysis in FIG. 37b shows that the ideal in-line valve will close when $P_{diffN} = P_{atm} - P_N$. Based on the open condition shown in FIG. 35, the valve must be open when the pressure differential across the valve is $P_{diff1} = P_{atm} - P_1$.

Because $P_N < P_1$, we can conclude that $P_{diffN} > P_{diff1}$ (i.e. the pressure differential is greater in the failure condition than in the open condition)

Therefore, the ideal valve properties are:
1) open for $P_{diff1}$
2) closed when $P_{diffN}$ This assumes that the valve can differentiate between these two pressure differentials. If the valve is sensitive enough to differentiate, then one possible solution is:
1) valve is normally closed
2) valve is forced open by $P_{diff1}$
3) any pressure less than $P_{diff1}$, such as $P_{diffN}$, does not affect valve Alternatively, the valve could be normally open
1) valve normally open
2) $P_{diff1}$ does not affect valve
3) $P_{diffN}$ forces valve to close In the analysis of FIG. 37a, it was noted that the development of airflow toward the source of differential pressure 6 dropped the pressure at the bifurcation enough to cause failure at the remaining attached aperture. The essential component of preventing failure of the remaining aperture is to maintain differential pressure at the bifurcation. This can be achieved without valves.

Airway resistance is one means of controlling pressure within the fluid circuit comprised of the vacuum tubing. If the parent tube 44 has a very low resistance to flow, and the daughter tubes 46 have a very high resistance to flow, then the pressure differential across the parent tube 44 is much less than the differential across each daughter tube 46. In terms of the analysis above, a very low parent tube 44 resistance will force $P_1$ to approach $P_N$. That is, the pressure drop between the bifurcation and the source is minimized so that $P_1$ approaches $P_N$ as shown in FIG. 38.

Assuming a steady, laminar, Newtonian, incompressible flow through the tubes, the flow resistance is proportional to the tube radius to the fourth power (resistance~$R^{-4}$). Therefore, in order to minimize flow resistance in the parent tube 44, the radius should be greater than that of the daughter tubes 46. If the daughter tubes 46 have a radius that is half that of the parent tube 44, then the flow resistance in each daughter tube 46 will be sixteen times greater than the resistance in the parent tube 44. Thus, the majority of the pressure drop will occur across the daughter tube 46, leaving the bifurcation pressure close to $P_N$. This results in daughter tubes 46 that function more independently (so loss of seal at one aperture has little or no effect on the pressure within the other aperture). Therefore, in some embodiments, proper selection of tube diameter is the preferred means of creating multiple "independent" vacuum ports on a single device using one connection to a vacuum source.

The above tubing 44, 46 and valve 42 embodiments can, likewise, be applied to the other housing 1 embodiments (i.e. the bowtie, elliptical, and cup shaped housings 1) wherein the embodiment includes more than one aperture 7 through which the source of differential pressure 6 is applied.

Figure 31:
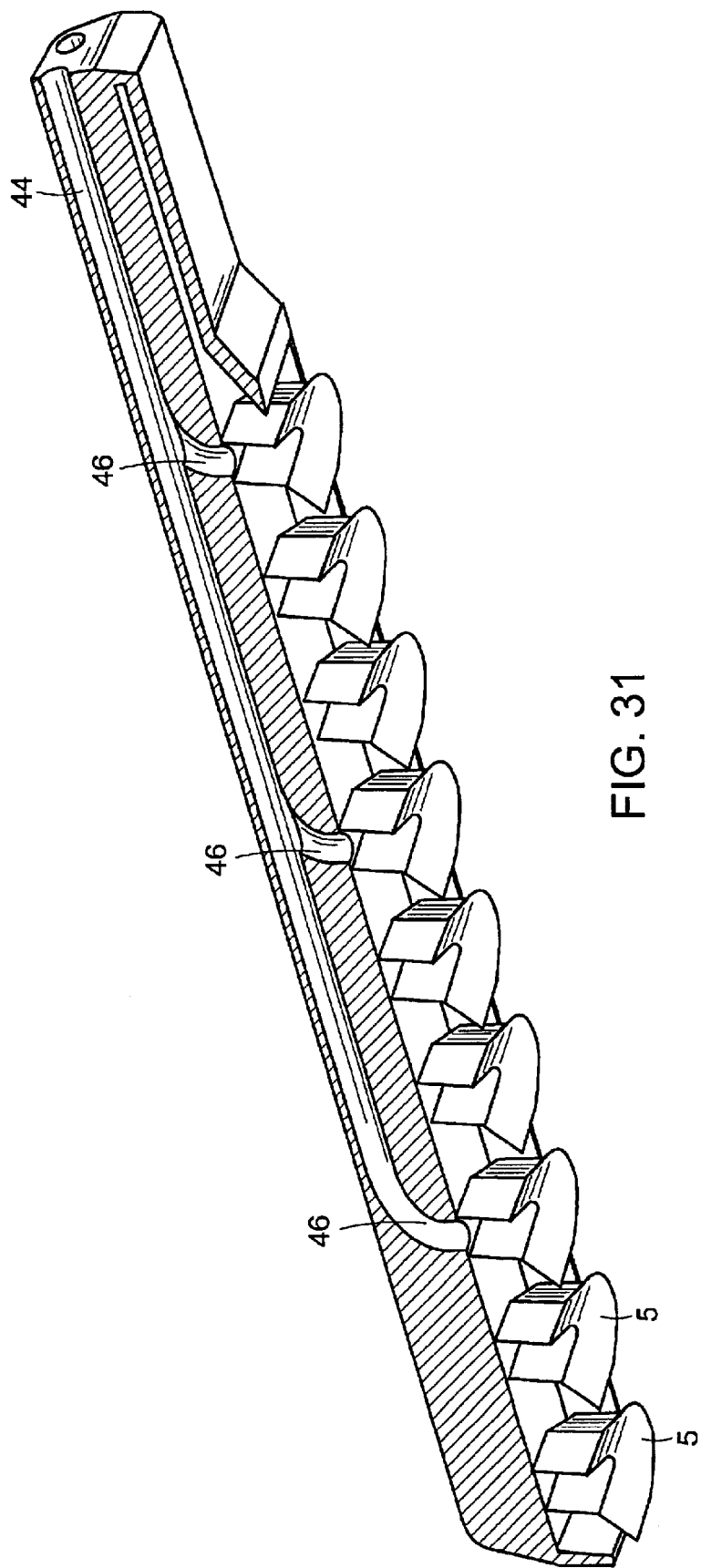
FIG. 31 shows a side cutaway view of another embodiment of the elongate housing having a plurality of flanges, wherein a parent tube connects to every third flange via daughter tubes.
Figure 32:
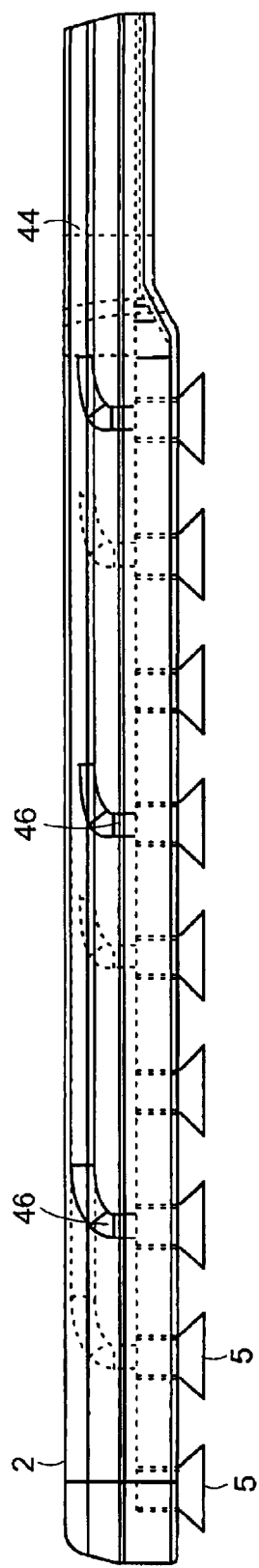
FIG. 32 shows a side view of the elongate housing of FIG. 31, showing how each parent tube connects to every third flange via daughter tubes.
Figure 33:
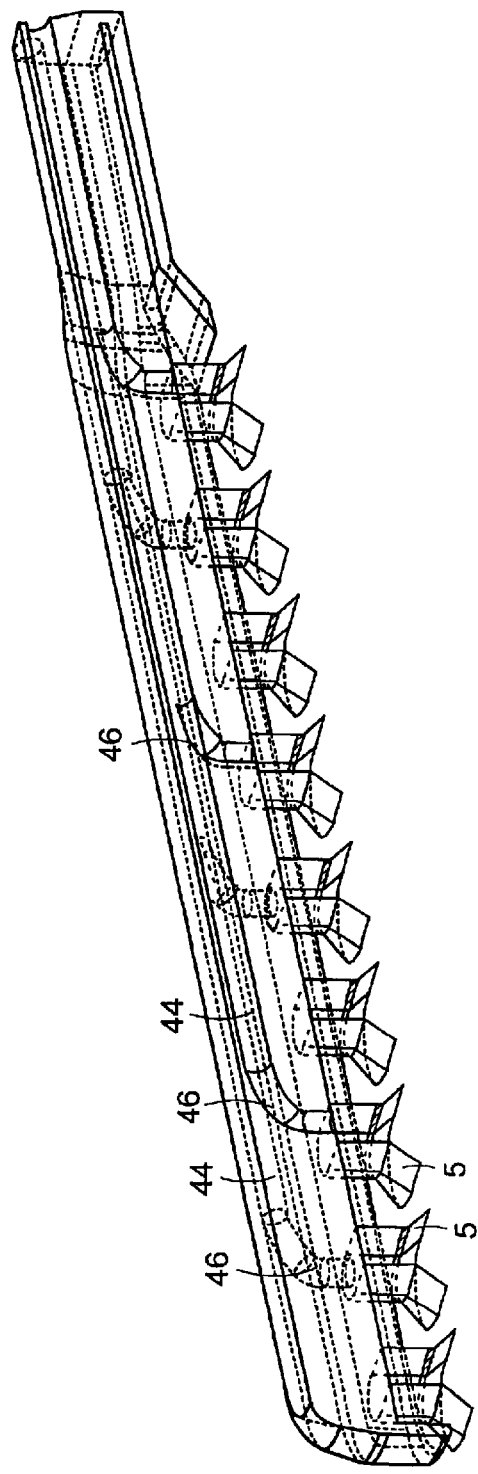
FIG. 33 shows a side cutaway view of the elongate housing of FIG. 32.
Figure 34:
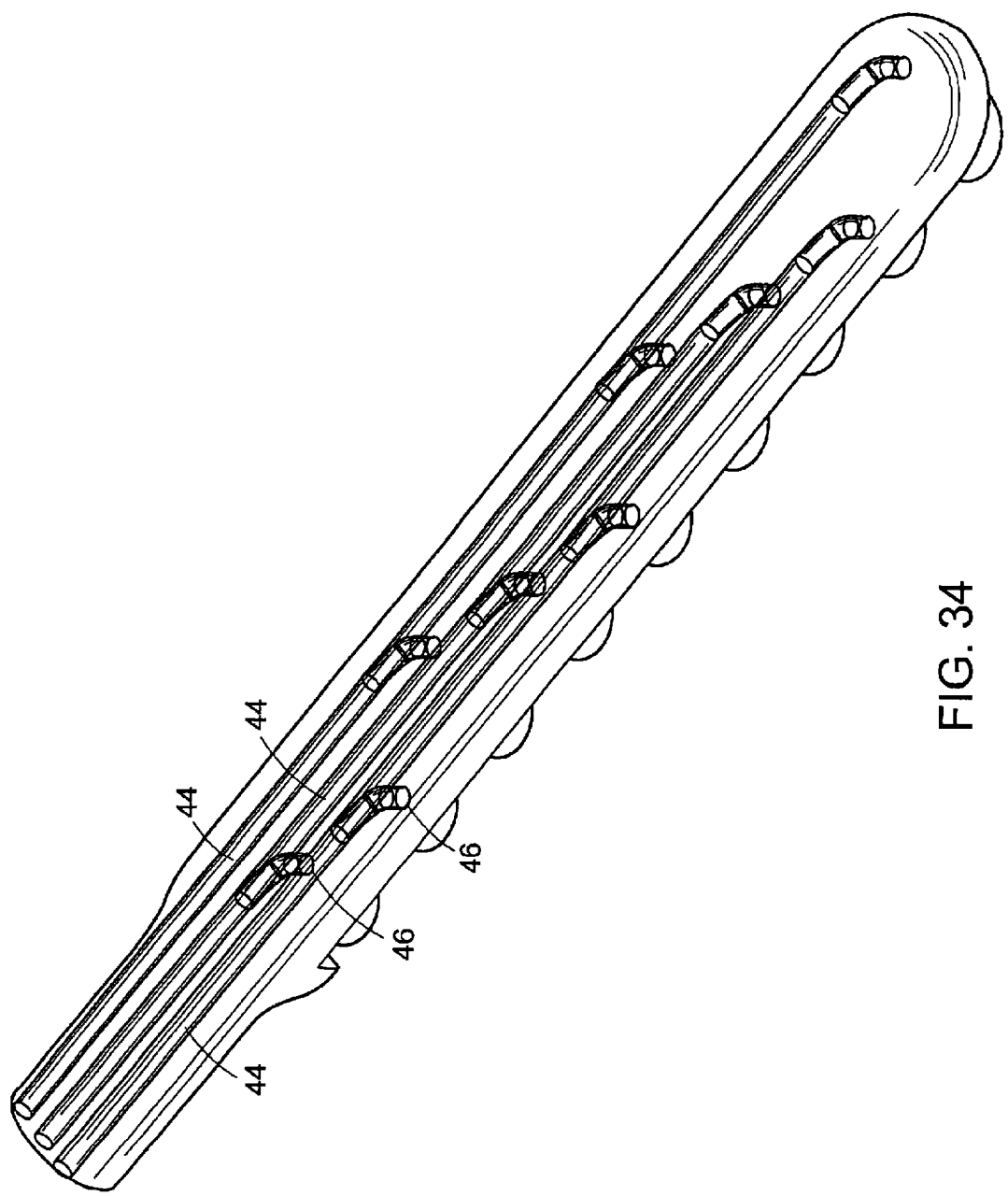
FIG. 34 shows an upper side perspective view of the elongate housing shown in FIG. 31 wherein three parent tubes are shown, each parent tube connects to three different flanges via daughter tubes, and each parent tube connects to every third flange.

In a particularly preferred embodiment, as shown in FIGS. 30–34, the elongate housing 1 has the following features: (1) three independent parent tubes 44 (possibly three separate connections to wall vacuum); (2) nine apertures 7, each preferably surrounded with a flange 5; (3) each parent tubes 44 supplies three apertures 7, so if one aperture seals fail, all the apertures on that parent tube 44 fail and the remaining apertures 7 supplied by the remaining two independent parent tubes 44 maintain the device's hold on the organ. For example, FIGS. 31 and 34 show that one of the vacuum lines supplies every third cup, starting with the most distal cup.

Any number of combination of apertures 7, flanges 5, and supply lines 40 can be used, wherein the array of apertures 7 all function independently via passive suction.

Figure 39:
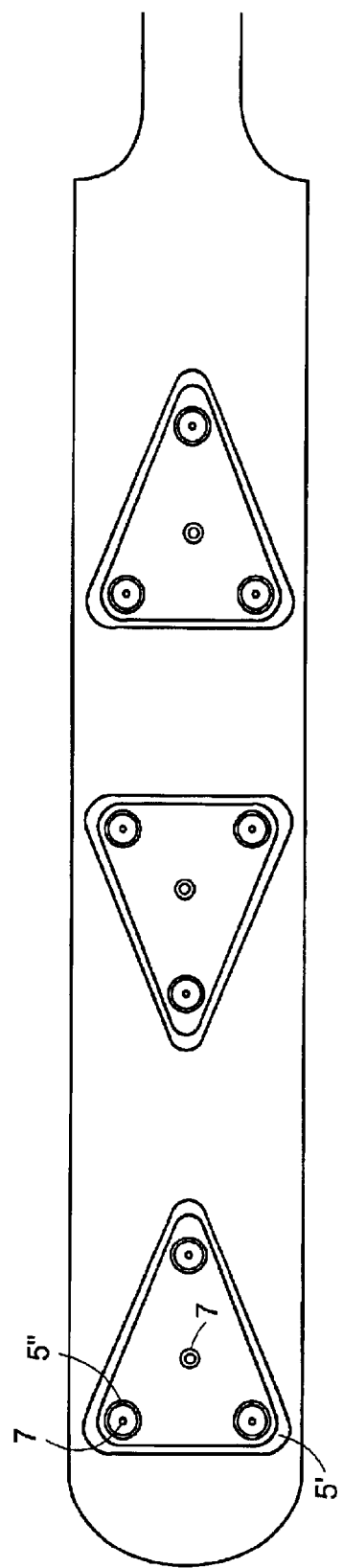
FIG. 39 shows a bottom view of another embodiment of the elongate housing having groups of apertures positioned within triangular flanges on the bottom surface of the housing.

For example, a triangular outer flange 5' with three independent flanges 5" in each corner of the triangular flange 5" could be used, wherein apertures 7 are located in the center of the triangular outer flange 5' for supplying the triangular outer flange 5' and in the center of each of the three independent flanges 5", as shown in FIG. 39. Preferably, the apertures are supplied by a total of four independent vacuum lines 40.

Figure 40:
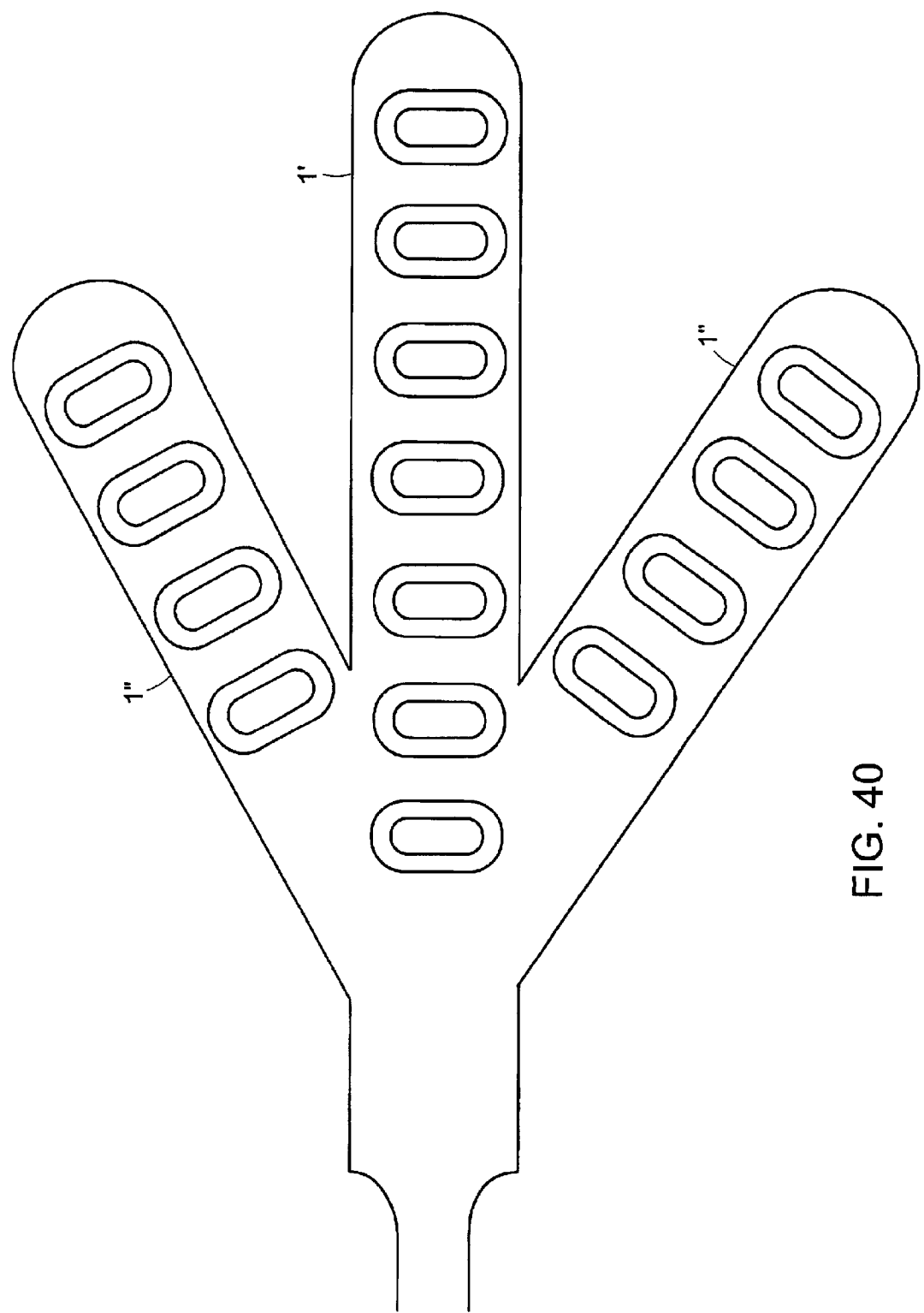
FIG. 40 shows a bottom view of another embodiment of the elongate housing having a center elongate housing with two elongate housings branched from the center elongate housing.

In another embodiment, for example as shown in FIG. 40, multiple elongate housings 1 could be connected together with a central elongate housing 1' and two or more elongate housings 1" branching out from the central elongate housing 1'. This embodiment would provide several independent "arms" for organ manipulation.

For each of the above elongate housing 1 embodiments, a reinforcing member 24, such as a malleable wire, could be further included along the length of the elongate housing 1 to allow the user to shape and conform the entire part to various organ surfaces.

Preferably, the elongate housing 1 is fabricated of a material that is rigid enough to prevent it from collapsing under the differential pressure, but flexible enough to allow a user to bend and manipulate the member along its length to provide contact between the portion(s) of the elongate housing 1 that contacts the organ and the surfaces of an organ. Such materials may include those set out above for the other housing embodiments (i.e. bowtie, elliptical, and cup shaped housings 1) which include, silicone gel, hydrogel, and closed cell foam, thermoplastic elastomers such as santoprene, polyisoprene, and polyurethane, and elastomers such as silicone. When included, the one or more flange 5 may be fabricated of those materials set out above for the other housing embodiments (i.e. bowtie, elliptical, and cup shaped housings 1) which include silicone gel, hydrogel, closed cell foam, 40 durometer silicone and 10 durometer silicone.

Preferably, the elongate housing 1 is flexible along its length to allow a user to shape the housing 1 to contact and adhere to various organs and various organ surfaces.

For each of the above housing embodiments (i.e. bowtie shaped, elliptical shaped, cross shaped, multi-arm shaped, cup-shaped and elongate housings 1) a gel, flexible film, or similar material can further be used in connection with the device to further enhance the adherence of the device on the organ. In these embodiments, the gel, flexible film or similar material is coated on the portions of the housing 1 that contact the organ. The gel, flexible film or similar material fills in voids between the organ and portions of the housing 1 that grasp the organ and provides a more secure seal between the device and the organ.

Figure 41:
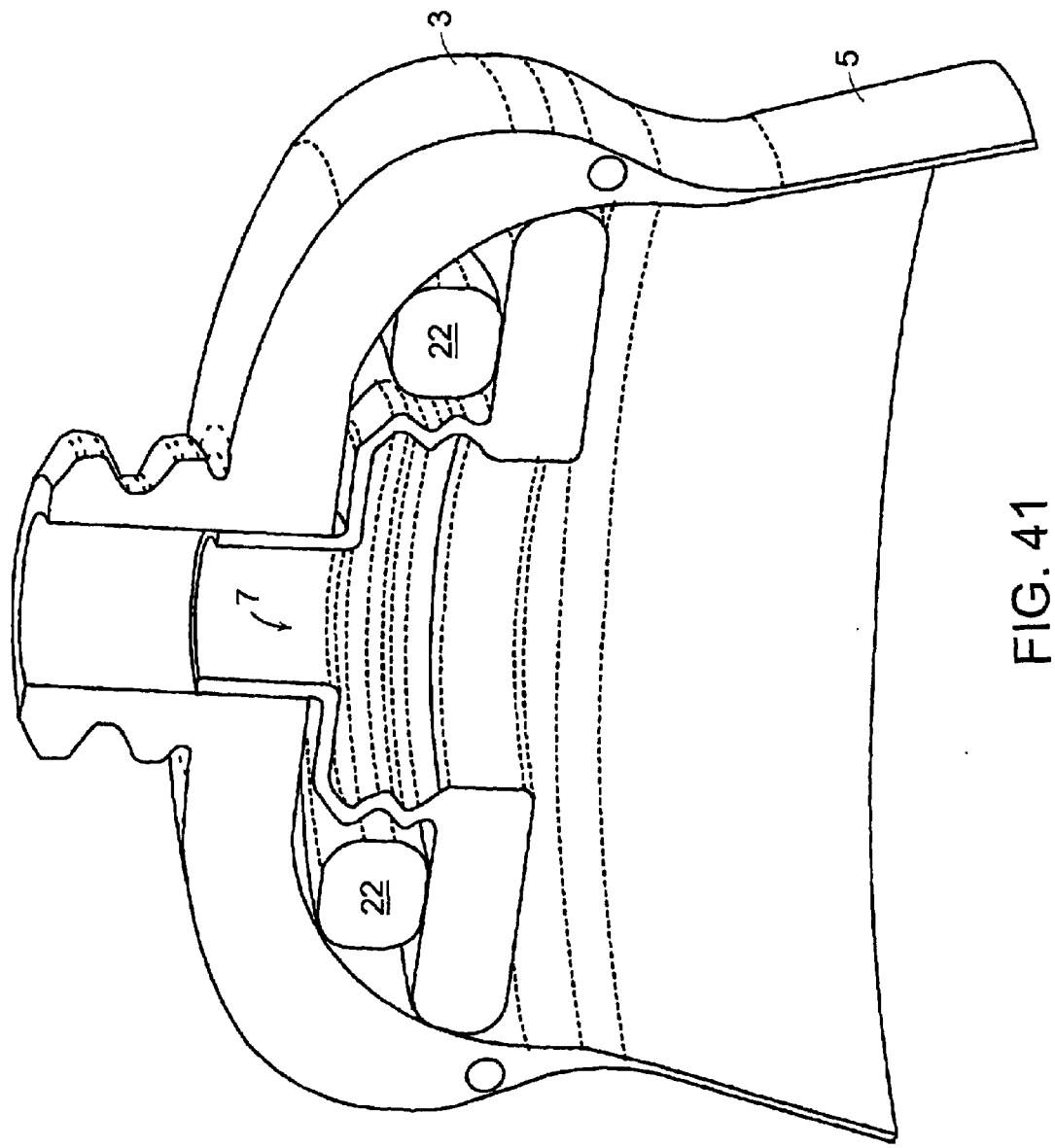
FIG. 41 shows another embodiment of the cup shaped housing having chambers holding a gel or flexible film positioned within the housing.
Figure 42:
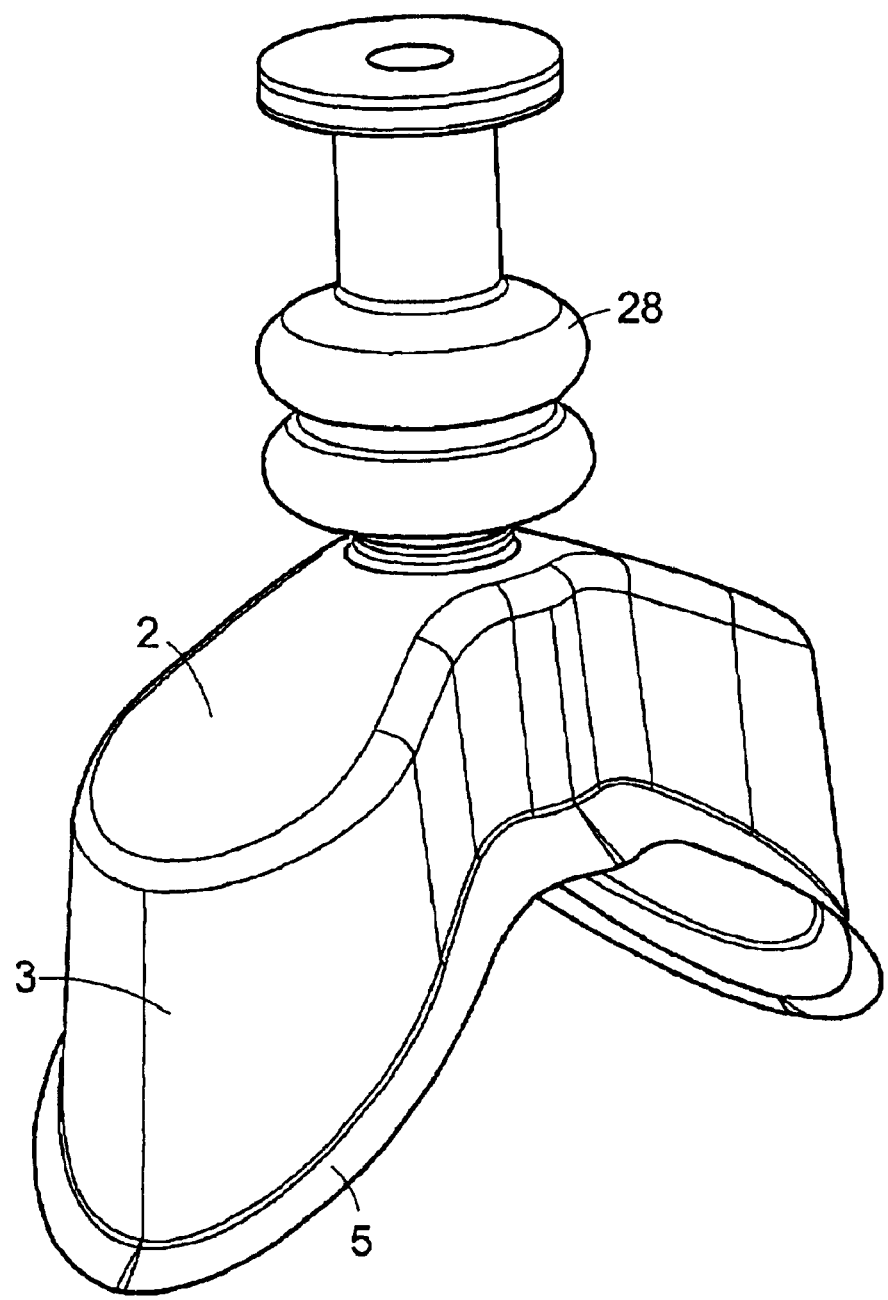
FIG. 42 shows an upper side view of another embodiment of the bowtie shaped housing having a ribbed attachment mechanism extending from the top surface of the housing.
Figure 43:
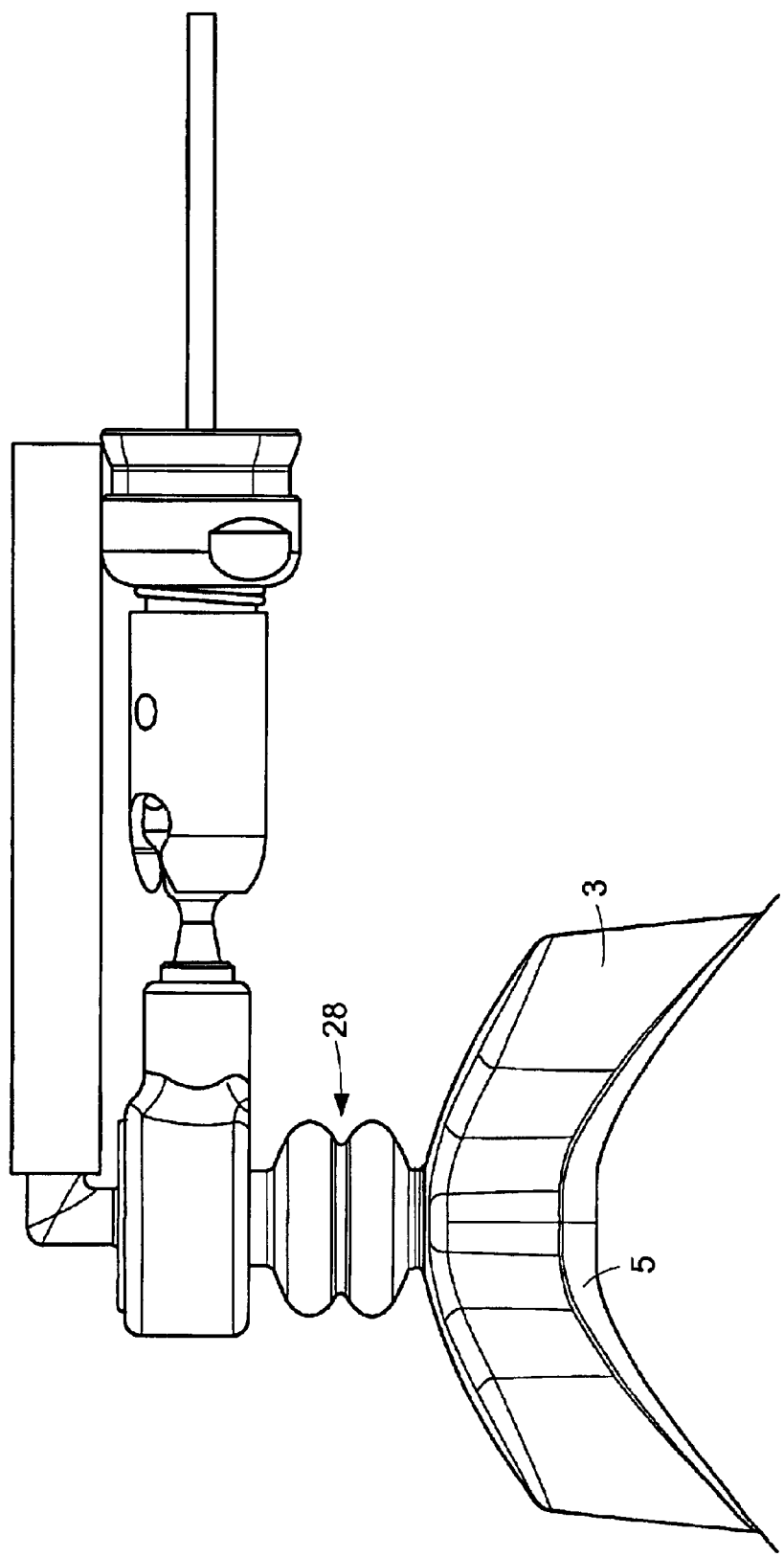
FIG. 43 shows the bowtie shaped housing of FIG. 42 as attached to a holding mechanism.
Figure 44:
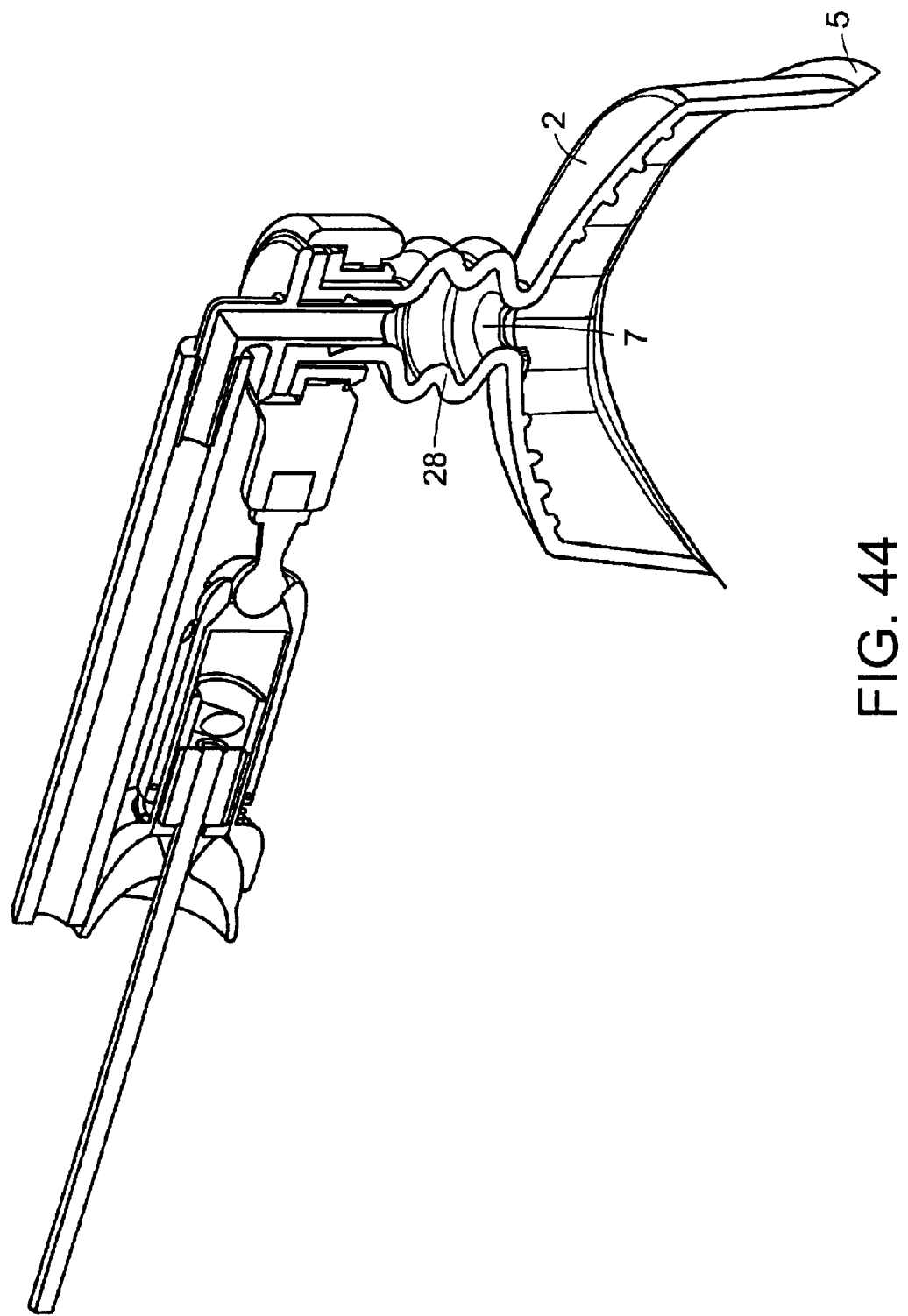
FIG. 44 shows a side cutaway view of FIG. 43.
Figure 45:
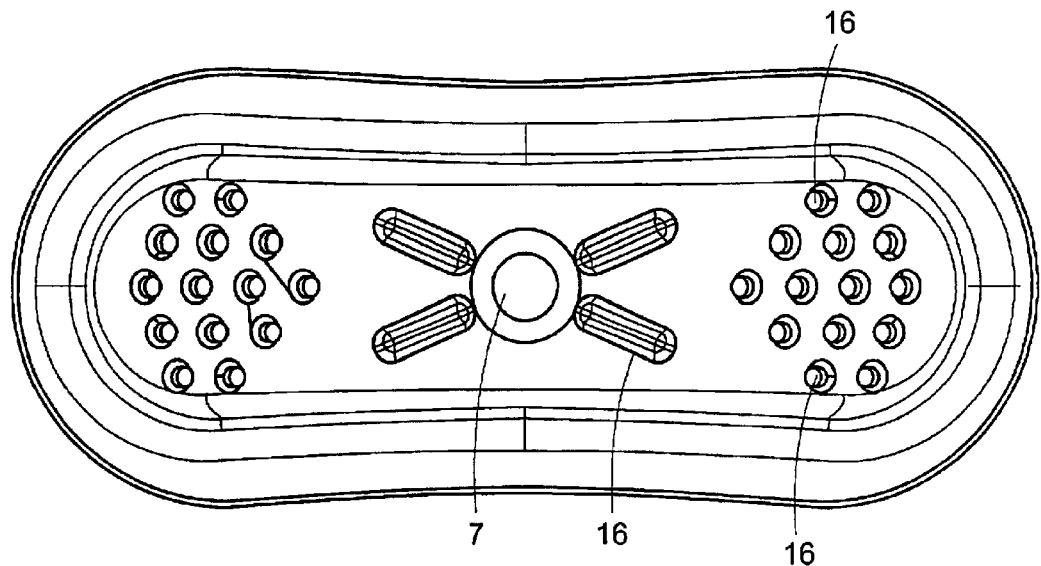
FIG. 45 shows a bottom view of another embodiment of the elliptical shaped housing having a plurality of ribs or protrusions within the housing.
Figure 46:
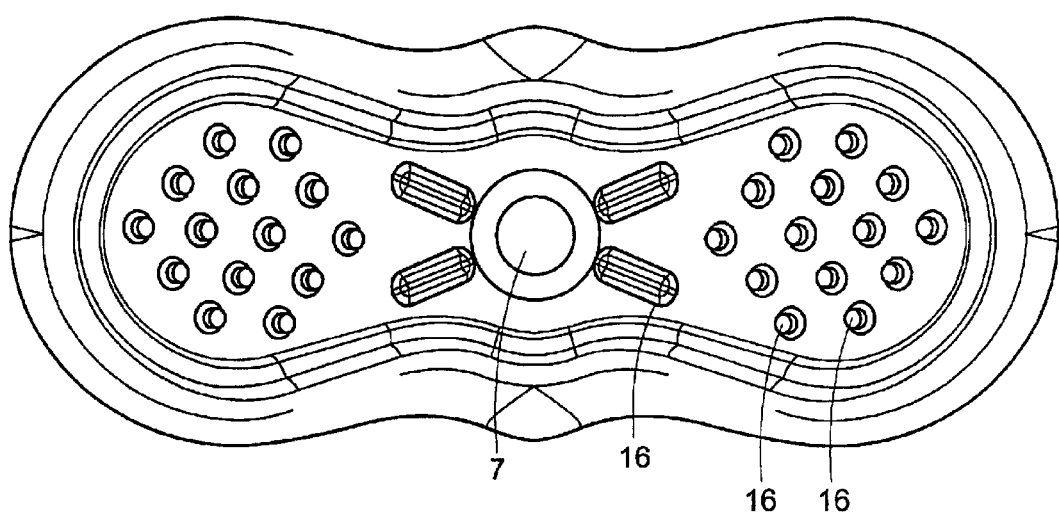
FIG. 46 shows a bottom view of another embodiment of the bowtie shaped housing having a plurality of ribs or protrusions within the housing.

In one embodiment, prior to use of the device, the gel, flexible film or similar material is applied to the portions of the housing 1 that contact the organ to provide an enhanced seal on the organ. In another embodiment, the gel or similar material could be held within the housing 1 or side portions 3 and released to the portions of the housing 1 that contact the organ when desired. For example, the gel or similar material could be held within one or more chambers 22 of the housing 1, as shown in FIG. 41, and the one or more chambers 22 may be opened to release the gel or similar material upon pressing a button or similar mechanism (not shown) that opens the one or more chambers 22. In another embodiment one or more chambers 22 can be positioned within the housing 1 such that as the housing 1 is pressed onto the surface of the organ, by the applied vacuum or source of differential pressure or by the user, the one or more chambers 22 are compressed to release the gel or similar material.

For each of the above housing embodiments (i.e. bowtie shaped, elliptical shaped, cross shaped, multi-arm shaped, cup-shaped and elongate housings 1), the housing 1 may further include protrusions or ribs 16 within the housing 1. In a preferred embodiment, the protrusions or ribs 16 are positioned on the bottom 18 of the top surface 2 of the housing 1, as shown in FIGS. 5, 6, 45, 46, 48, 49d, 50c–d and 51a–b. The protrusions or ribs 16 can also be located elsewhere within the opening 8 of the housing, for example, on the side portions 3, if desired. The protrusions or ribs 6 are preferably designed to prevent the organ from becoming pulled into the one or more apertures 7 by the differential pressure source 6, thereby blocking the differential pressure source 6. The protrusions or ribs 16 are formed to be atraumatic, to avoid tissue abrasion or damage. Thus, the protrusions or ribs 16 may, for example, be formed with curved, rounded edges.

In some embodiments, the protrusions or ribs 16 are designed to assist the device in forming a seal on the organ at the outer perimeter of the housing 1. For example, the protrusions or ribs 16 can be designed to prevent the device from forming a seal on the organ inside of the housing. Rather, the protrusions or ribs 16 would promote the formation of a seal on the organ at the one or more flanges 5 or side portions 3. The protrusions or ribs 16 could, for example, be formed along the surfaces inside of the housing 1 such that, if the organ is pulled within the housing 1, the surface of the organ is contacted by the plurality of protrusions or ribs 16 rather than by, for example, the relatively smooth inner surface of the housing 1. The voids between the protrusions or ribs 16 that contact the organ will inhibit the formation of a seal. Without being bound by theory, it is believed that by maximizing the surface area of the device's seal on the organ, the hold of the device on the organ and, thus, the lift capability of the device are enhanced. The surface area can be maximized by formation of a seal at the outer perimeter of the housing 1, where surface area is generally the largest, rather than inside of the housing 1, where surface area is generally decreased.

For each of the above housing embodiments (i.e. bowtie shaped, elliptical shaped, cross shaped, multi-arm shaped, cup-shaped and elongate housings 1), the housing 1 may further include a screen 20 or similar mechanism, as shown in FIGS. 9 and 10. The screen 20, or similar mechanism prevents the organ from becoming pulled into the one or more apertures 7 by the differential pressure source 6. Alternatively, rather than a screen 20, a foam, or other material porous to air may be placed in front of the one or more apertures to prevent the organ from becoming pulled into the one or more apertures 7 by the differential pressure source 6. In one embodiment, as shown in FIGS. 9 and 10, a screen 20 is placed directly on the bottom 18 of the top surface 2 of the housing 1. The screen 20, can also be located elsewhere within the opening 8, for example, it may extend across the opening 8 at a distance away from the bottom 18 of the top surface 2 of the housing 1. Preferably, the screen 20 is located near the bottom 18 of the top surface 2 to provide space within the opening 8 into which the organ can be pulled and to prevent the screen 20 from pushing the organ out of the opening 8, which can cause the device to lose its grip on the organ. The screen 20 may line the entire opening 8, as shown in FIG. 9. For example, the screen 20 may be placed directly upon the bottom 18 of the top surface 2 and may line the entire bottom 18 of the top surface 2. Alternatively, the screen 20 can line one or more portions of the opening 8 near the one or more apertures 7. For example, the screen 20 can line a portion of the bottom 18 of the top surface, as shown in FIG. 10.

In some embodiments, both screens 20 and protrusions or ribs 16 are included within the housing. For example, the protrusions or ribs 16 can be arranged on the bottom 18 of the top surface and the screen 20 can be placed over the entire bottom 19 of the top surface covering the protrusions or ribs 16. The protrusions or ribs 16 can provide surfaces on which the screen 20 rests, such that the screen 20 does not lie directly against the bottom 18 of the top surface 2. In another embodiment, the protrusions or ribs 16 can be arranged on the bottom 18 of the top surface and the screen 20 can be placed over a portion of the bottom surface 18 over the one or more apertures 7. The screens 20 can overlap the protrusions or ribs 16 and/or can be placed over portions of the bottom 18 not covered with protrusions or ribs 16, as shown in FIG. 10.

The screen 20 is formed to be atraumatic, to avoid tissue abrasion or damage if the organ contacts the screen 20. In one embodiment, a screen is fabricated of an elastomeric mesh, such as santoprene or silicone, or for example, in one embodiment, the screen 20 is formed of SepraFilm or a similar bio-reabsorbable mesh. In some embodiments, SepraFilm is used to coat a screen 20 fabricated of other materials. Without being bound by theory, it is believed that the use of SepraFilm will help prevent adhesions of the organ tissue to the screen 20 upon contact and prevent fibrin deposition thereby minimizing residual tissue damage or tissue response to the applied vacuum.

Materials useful in fabricating the housing 1 are described above and can be readily determined by one of skill in the art. As set out previously, some exemplary materials include, silicone gel, hydrogel, and closed cell foam, thermoplastic elastomers such as santoprene, polyisoprene, and polyurethane, and elastomers such as silicone. Non-flexible materials may be used in parts of the housing where rigidity or strength is required, such as upper portions that do not contact tissue, but must resist vacuum forces. These materials may include, for example, ABS, polycarbonate, polysulfone, polypropylene, or polyurethane. In a preferred embodiment, the single molded part is fabricated of silicone or a thermoplastic elastomer of very low durometer.

Preferably, the housing 1 is designed to prevent it from collapsing or inverting during use and under the influence of the differential pressure source 6. The shape and sizes of the various portions of the housing 1, e.g. top surface 2, side portions 3 and flanges 5, also can be designed to minimize the potential for collapsing and inversion. Preferably, the housing 1 also provides sufficient flexibility where desired so that the user can shape the housing 1 to contact and fit the contours of various organ surfaces. The portion of the housing 1 that contacts the organ, (e.g. the side portions 3 and/or the one or more flanges 5) is fabricated to prevent trauma to the organ, to conform to the contours of various organ surfaces and to form a secure seal on the organ surface.

Figure 47A:
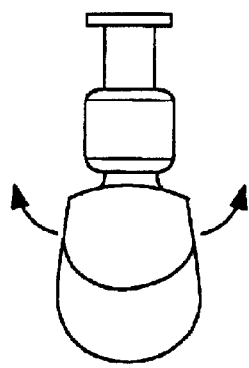
FIG. 47a shows a front view of another embodiment of the elliptical shaped housing, wherein side wall flex is depicted.
Figure 47B:
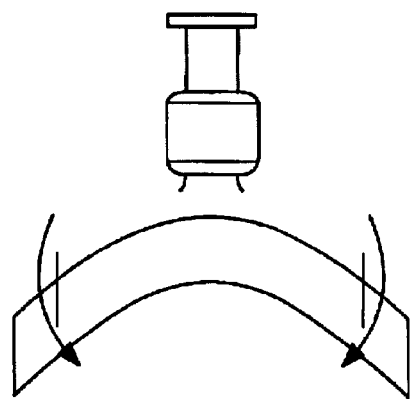
FIG. 47b shows a side view of another embodiment of the elliptical shaped housing, wherein wing (or end portion) flex is depicted.
Figure 47C:
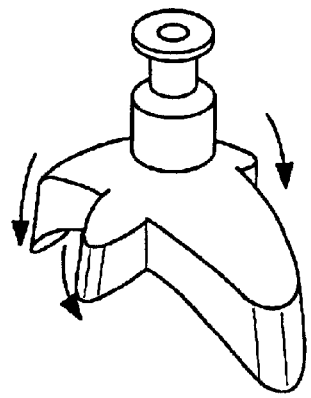
FIG. 47c shows a side perspective view of a cross shaped device.
Figure 48:
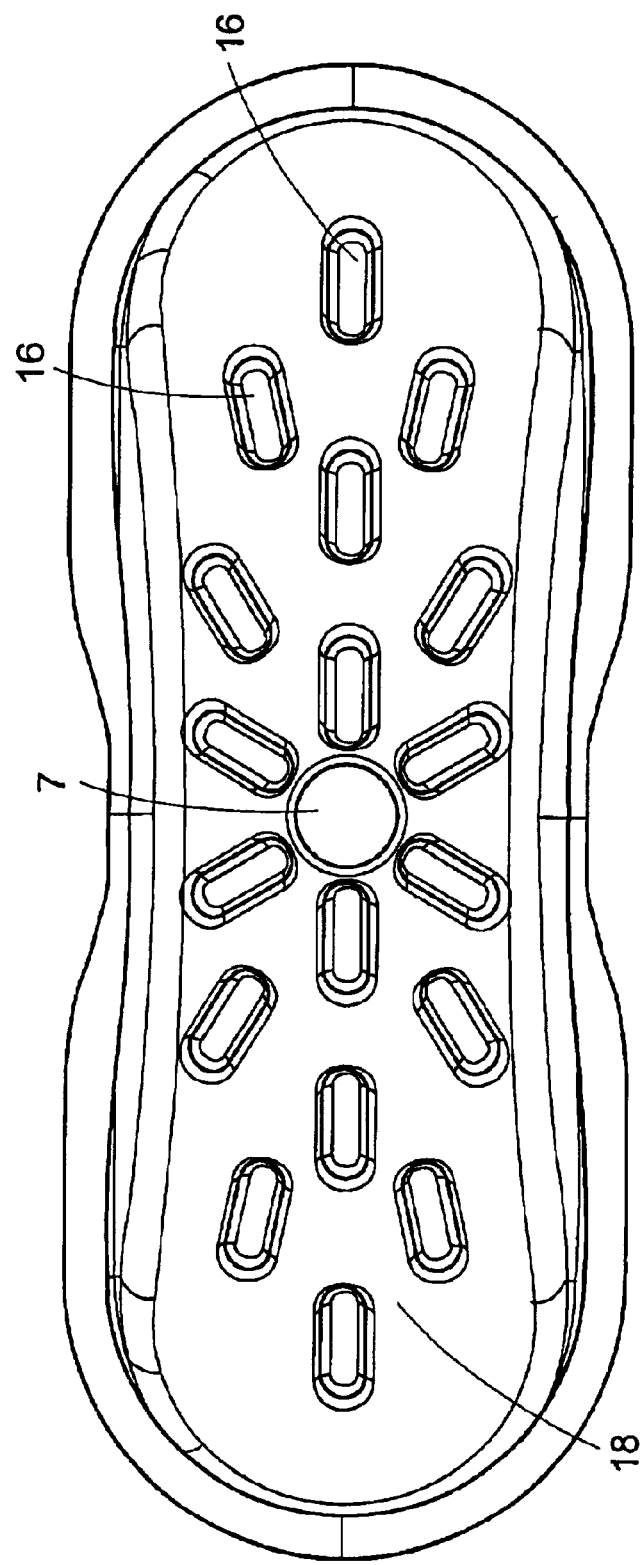
FIG. 48 shows a bottom view of a bowtie shaped device having vertical, thinned side portions
Figure 49A:
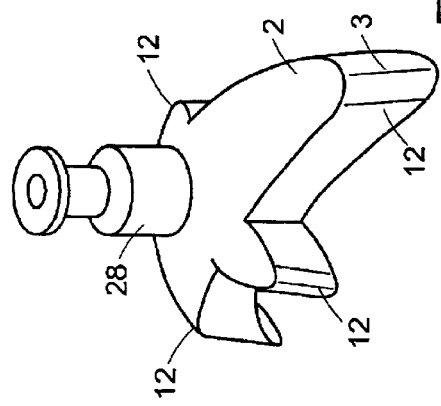
FIGS. 49a–d show various views of a cross shaped device in accordance with another embodiment of the present invention.
Figure 49B:
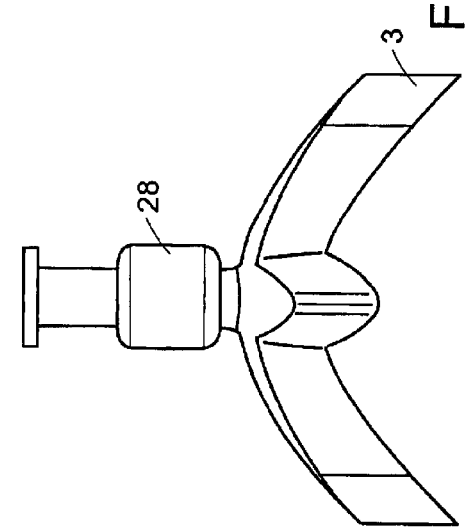
Figure 49C:
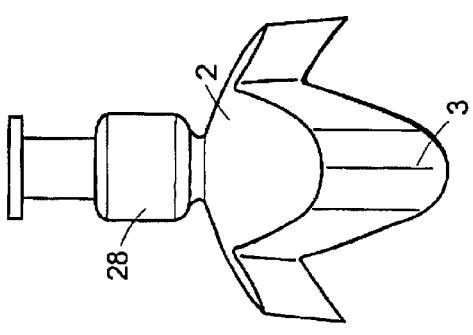
Figure 49D:
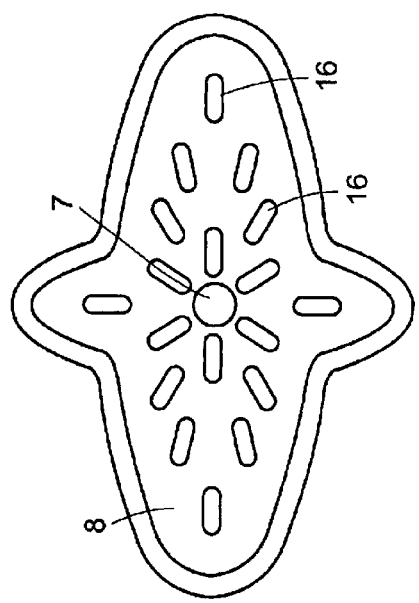
Figure 50A:
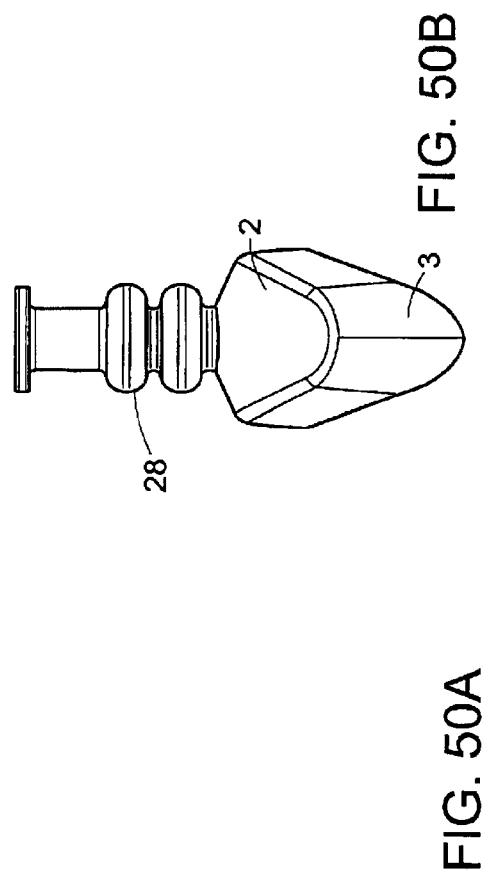
FIGS. 50a–d show various views of an elliptical shaped device in accordance with another embodiment of the present invention.
Figure 50B:
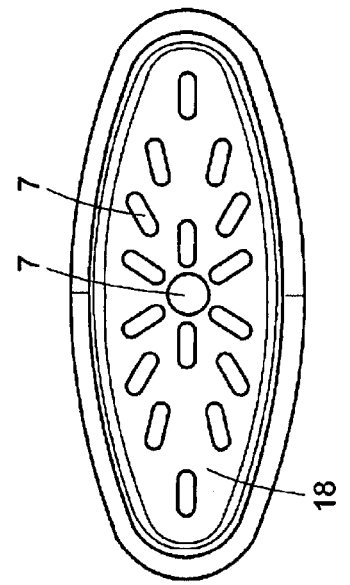
Figure 50C:
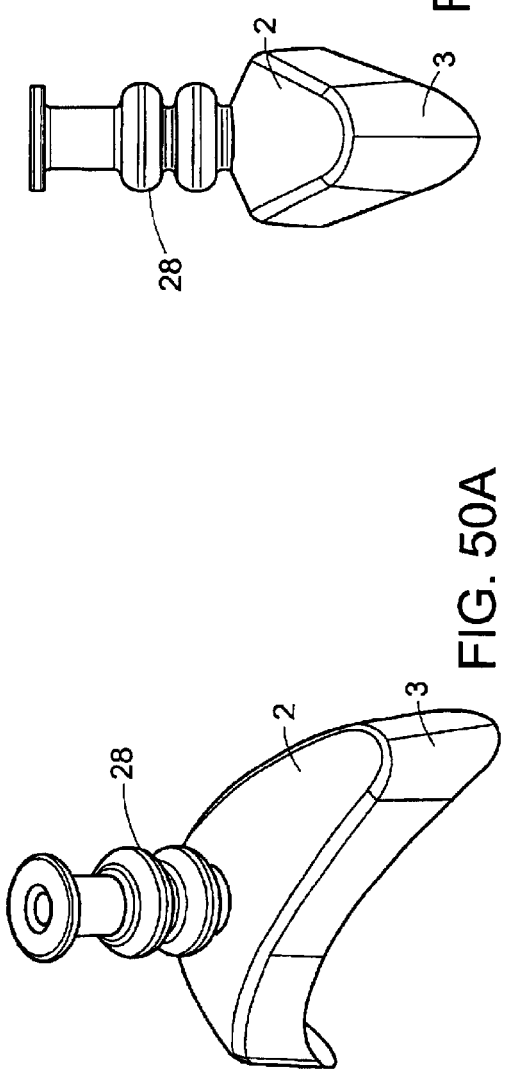
Figure 50D:
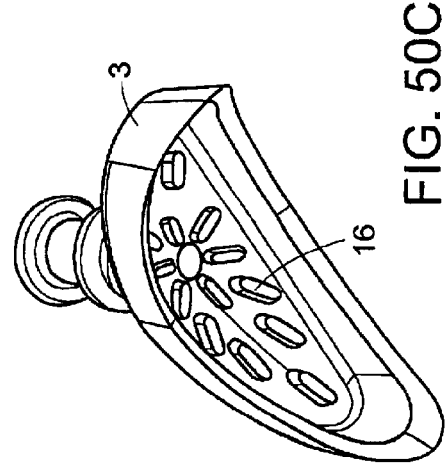
Figure 51A:
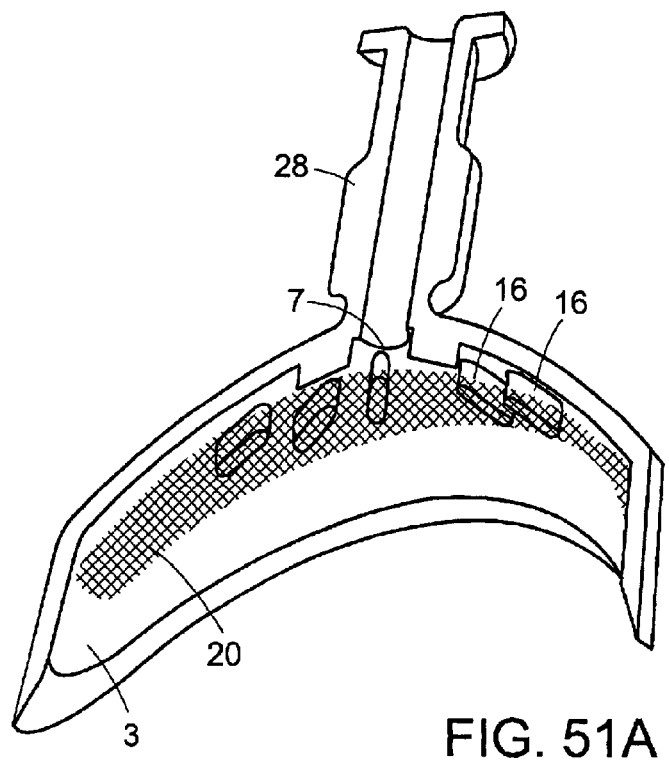
FIGS. 51a–b show cut-away perspective views of an elliptical shaped device in accordance with another embodiment of the present invention.
Figure 51B:
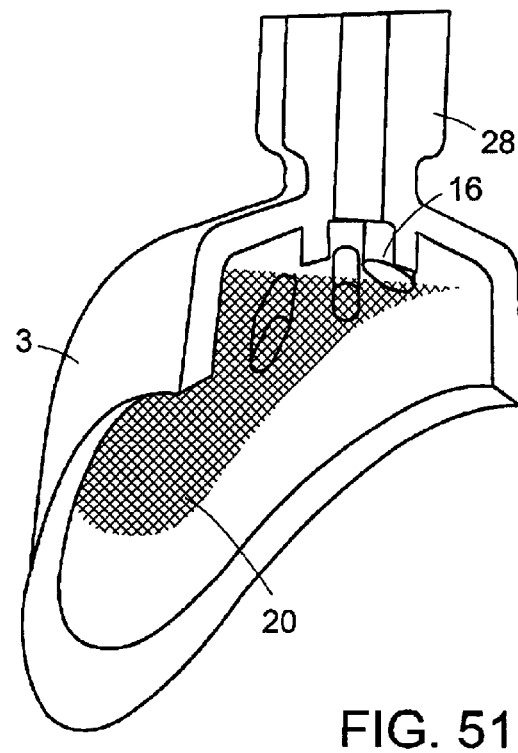

For the bowtie and elliptical shaped housing 1 embodiments, under "extreme lift conditions", the middle of the side portions 3 can exhibit some outward movement. Namely, as shown in FIG. 47*b*, "wing flex" may occur. Wing flex allows the device to conform to irregular, dynamically flexing features of the organ (e.g. the surface of a beating heart). However, wing flex can cause the middle of the side portions to flex outward away from the stretching tissue of the organ. This can break the seal of the device on the organ. As used herein, "extreme lift" is defined as a situation in which the user applies a lifting force on the organ such that the organ is physically stretched out of its normal shape. While such an aggressive type of lifting of the organ is typically not necessary under normal circumstances in which the device is used, the manipulation device is designed with anticipated, extenuated/extreme use circumstances in mind, as part of the risk assessment for the device Without being bound by theory, it is believed that the lifting capability (adherence) of the device under extreme lift conditions can be maximized by maximizing the surface area of the device on the organ. By maximizing the surface area of the device on the organ, the area of adherence of the device increases. It is believed that this increases the strength of the adherence or lifting capability of the device. Further, when the device is used with a source of differential pressure, increasing the surface area of the device on the organ likewise increases the area of the organ affected by the differential pressure. In other words, for example, when the device is used with a vacuum, an increase in the surface area of the device on the organ will increase the area of the organ affected by the vacuum, which thereby strengthens the lifting capability of the device on the organ.

Maximizing the surface area of the device on the organ and maintaining seal during extreme lift can be accomplished in a number of ways.

The shape of the bowtie shaped housing 1 promotes the maintenance of the seal of the device on the organ during wing flex. Further, for each of the housing 1 embodiments, (e.g. elliptical, bowtie, cross, multi-arm and elongate) the device's ability to maintain the seal of the device on the organ during wing flex can be improved by forming the side portions 3 thin and/or compliant, as depicted in FIGS. 57*a–b* and 58*a–b*. For example, in one embodiment, the side portions 3 of the housing 1 are fabricated to extend vertically downwards from the top surface 2, for example, as shown in FIG. 1. In such embodiments, by forming the side portions 3 thin and/or compliant, as depicted in FIGS. 57*a–b* and 58*a–b*, the seal made by the device is enhanced to overcome breaking of the seal under extreme lift conditions. That is, the outward lift of the side portions 3 that can occur during extreme lift is prevented, and therefore seal is maintained, by having thin or highly compliant side portions 3.

Figure 59A:
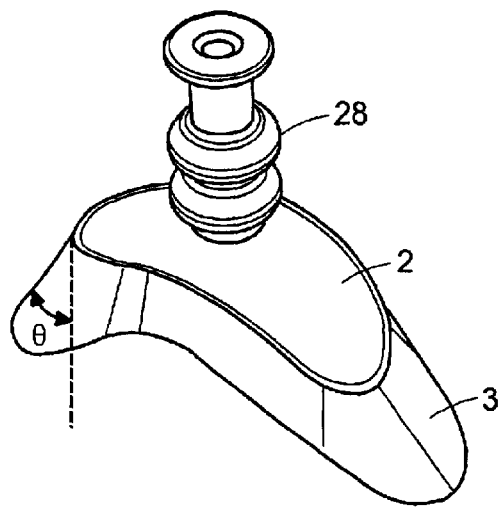
FIGS. 59a–b shows an elliptical shaped device having side portions that extend at an angle from the top surface of the housing in accordance with one embodiment of the present invention.
Figure 59B:
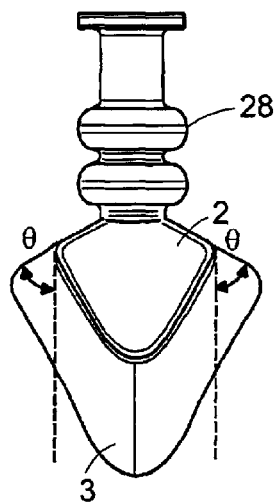
Figure 59C:
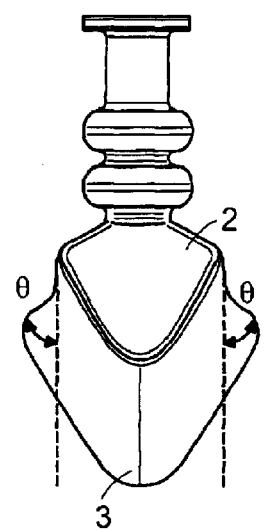

The shape of the elliptical shaped housing 1, in particular, enhances the device's ability to flatten or "flare-out". Further, for each of the housing 1 embodiments, (e.g. elliptical, bowtie, cross, multi-arm and elongate) the device's ability to flatten or "flare-out" can be further enhanced by fabricating the side portions 3 of the housing 1 to extend at an angle θ from the top surface 2 of the housing 1, as shown in FIGS. 59*a* and 59*b*. Without being bound by theory, it is believed that by angling the side portions 3 from the top surface 2, the ability of the housing 1 the flatten or "flare-out" against the surface of the organ is increased and that such flattening increases the surface area which, in turn, enhances the hold of the device on the organ. The angle θ formed between the top surface 2 and the side portions 3 can vary and, preferably, is at least 5°, more preferably, at least 10°, and more preferably, between about 5° and 15°. Still further, in some embodiments, rather than extend the side portions 3 of the housing an angle θ directly from the top surface 2, the side portions 3 may extend vertically from the top surface 3 for a portion of their length and then extend at an angle θ for the remainder of their length, as shown, for example, in FIG. 59*c*.

In other embodiments, it is believed that the seal of the device under extreme lift conditions can be maintained by modifying the bowtie and elliptical shaped housings 1 to form a "cross-like" shaped housing, for example, as shown in FIGS. 47*c* and 49*a–d*, or a modified cross-shaped or multi-arm shaped housing, as shown in FIGS. 60*a–b*. It is believed that the additional ends 12 enhance the ability of the portions of the device affected by the side wall flex during wing flex to maintain their seal on the organ. In particular, by positioning additional ends 12 at the center of the side portions, as shown in FIGS. 47*c* and 49*a–d*, the device maintains the adherence of the side portions/flanges to the organ at the-flex points. By maintaining the seal of the device on the organ at all points along the portions of the device that contact the organ, the strength of the seal of the device on the organ is increased as well as the lift strength of the device. Without being bound by theory, it is believed that the differential pressure and seal of the additional ends 12 assist in maintaining the seal of the side portions 3 during wing flex, especially during extreme lift. Further, the additional arms 12 increase surface area of the device on the organ, thereby enhancing the lift capability of the device on the organ. In particular, by increasing the surface area of the device on the organ, the additional arms 12 increase the area of adherence of the device, which increases the lifting strength of the device. Further, when the device is used with a source of differential pressure, the additional arms 12 increase the surface area of the device on the organ which, likewise, increases the area of the organ affected by the differential pressure. Still further, forming additional arms along the flex points allows for a controlled flexing of the device as well as a predictable response to various normal and extreme lift conditions.

Further, under normal lift conditions, the above embodiments can be used to enhance the seal of the device on the organ. Namely, the side portions 3 can be made sufficiently thin and/or compliant to enhance the ability of the housing to flatten or flare-out on the organ surface and the side portions 3 can be fabricated to extend at an angle from the top surface 2 to enhance the ability of the housing to flatten or flare-out on the organ surface. As used herein, "normal lift conditions" is defined as manipulation of an organ that does not deform the organ substantially from its original configuration/geometry.

Likewise, in the cup shaped housing and elongate housing embodiments, the side portions 3 can be fabricated to maximize the surface area of the device on the organ surface. Thus, for example, the side portions 3 of the cup shaped housing and elongate housing embodiments may be fabricated sufficiently thin and/or compliant to enhance flattening or flare-out of the device on the organ surface. The side portions 3 of the cup shaped housing and elongate housing embodiments can also be fabricated to extend at an angle from the top surface, which it is believed, will enhance the ability of the housing to flatten or flare-out on the organ surface. It is believed that by increasing the surface area of the device on the organ surface, a stronger seal and adherence of the device on the organ can be obtained. Further, when the device is used with a source of differential pressure, an increase in the surface area of the device on the organ results in an increase in the surface of the organ affected by the differential pressure. This results in a stronger seal and a stronger adherence of the device on the organ, and therefore a greater lift capability.

In a particularly preferred embodiment, the entire housing 1, including top surface 2, side portions 3 and flanges 5, are fabricated single molded part. Sufficient rigidity to prevent the housing 1 from collapsing or inverting during use can be provided by forming the housing 1 thicker at portions requiring enhanced structural stability. The portions of the housing 1 contacting the organ can be fabricated with a desired flexibility by forming those portions more thinly than the portions requiring rigidity. For example, in embodiments including one or more flanges 5, the one the one or more flanges 5 are preferably fabricated to be very thin and highly compliant, which is believed to enhance the formation of a secure seal on the organ surface.

Figure 16:
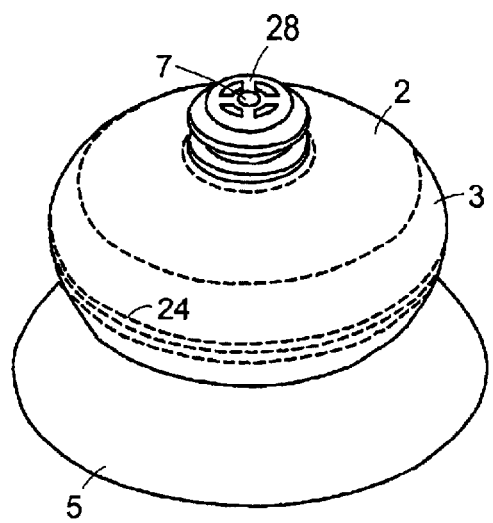
FIG. 16 shows an upper side perspective view of one embodiment of the cup shaped housing.
Figure 17:
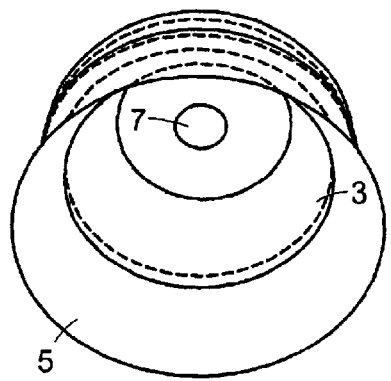
FIG. 17 shows a lower side perspective view of the cup shaped housing of FIG. 16.

For each of the above housing embodiments (i.e. bowtie shaped, elliptical shaped, cross shaped, multi-arm shaped, cup-shaped and elongate housings 1), the housing 1 may further include a reinforcing member 24, for example, as shown in the cup shaped housing embodiment of FIG. 16. The reinforcing member may be, for example, a 12 gage electrical wire or the like, to provide rigidity while still providing flexibility where desired so that the user can shape the housing 1 to contact and fit the contours of the desired organ. In some embodiments, the reinforcing member 24 can be molded into the housing 1. In other embodiments, the housing 1 may include one or more notches 26, as shown in FIG. 18 into which one or more reinforcing member 24 can be inserted and removed as desired.

In some embodiments, different portions of the housing 1 are formed of different materials to provide each part with its desired characteristics. For example, sufficient rigidity to prevent the housing 1 from collapsing or inverting during use can be provided by forming select portions of the housing 1 of a material more rigid than the portions of the housing 1 that contact the organ and portions of the housing that require flexibility for shaping the housing 1 to fit the contours of various organ surfaces. For example, the side portions 3 and/or one or more flanges 5 can be fabricated of a material more flexible than the portions of the housing 1 that provide rigidity to prevent collapsing and inversion of the housing 1 during use and under the influence of a differential pressure source 6. Such materials may be selected from any of those materials set out herein and may be readily determined by one of skill in the art.

When included, the one or more flanges 5 can be fabricated of the same materials useful in fabricating the housing. In addition, particularly compliant materials such as silicone gel, hydrogel and closed cell foam can be used. Some particularly preferred materials for use in forming the one or more flanges 5 include silicone gel, 40 durometer silicone and 10 durometer silicone, more preferably, 0.012" thick 40 durometer silicone and 0.020" thick 10 durometer silicone. The 0.012" thick 40 durometer silicone, while thin, has a high tensile strength and relatively low elongation due to its relatively high durometer. The 0.020" thick 10 durometer silicone is more compliant and has a high elongation. Materials having properties similar to these materials can also be used and may be readily determined by one skilled in the art. In general, it is desired that the material is compliant so that it coats or conforms to the unpredictable geometry of various organs. Further, materials with high tensile strength are preferable.

In a preferred embodiment, as shown in FIGS. 16, 18, 22, 23 and 41–44, an attachment mechanism 28 extends from the top surface 2 of the housing 1. The attachment mechanism 28 can be held manually or can be attached to a holding mechanism, such as a retractor, during use. The attachment mechanism 28 is preferably flexible along its length to allow for energy absorption and multidirectional movement of the housing 1 as the organ moves (e.g. as the heart beats) and to prevent the device from losing its grip on the organ due to movement of the organ or the device during use. The attachment mechanism preferably allows for up and down, side to side and rotational movement of the device to maintain the device's seal or adherence on the organ during organ and/or device movement. In a preferred embodiment, the attachment mechanism 28 has a ribbed length, which allows for energy absorption and multidirectional movement of the housing 1 as the organ moves. When the device is used in connection with a source of differential pressure, this ribbing also allows flex of the "neck" portion of the device without kinking or blocking the lumen 34 or one or more tubes within the neck.

In some embodiments, a spreading mechanism for moving the ends 12 of the bowtie, elliptical, cross or multi-arm shaped housing 1 away from each other is included. Prior to attachment of the device to an organ, the spreading mechanism can be used to move the ends 12 away from each other so that the side portions 3 or flanges 5 can be positioned on desired portions of the organ surface. After the side portions 3 or flanges 5 are placed on the organ, the ends 12 of the housing can be allowed to go back to their natural state towards each other, thereby enhancing the adhesion of the device on the organ surface. Spreading the ends 12 away from each other prior to placing the device on the organ further assists in flattening the device on the organ (i.e. flaring out the device as shown in FIGS. 57*a–b* and 58*a–b*).

As set out above, flattening or flaring out of the device is particularly beneficial in increasing the surface area of the device on the organ surface, which results in the formation of a stronger seal or adherence of the device on the organ surface, and therefore greater lift capability.

Figure 15:
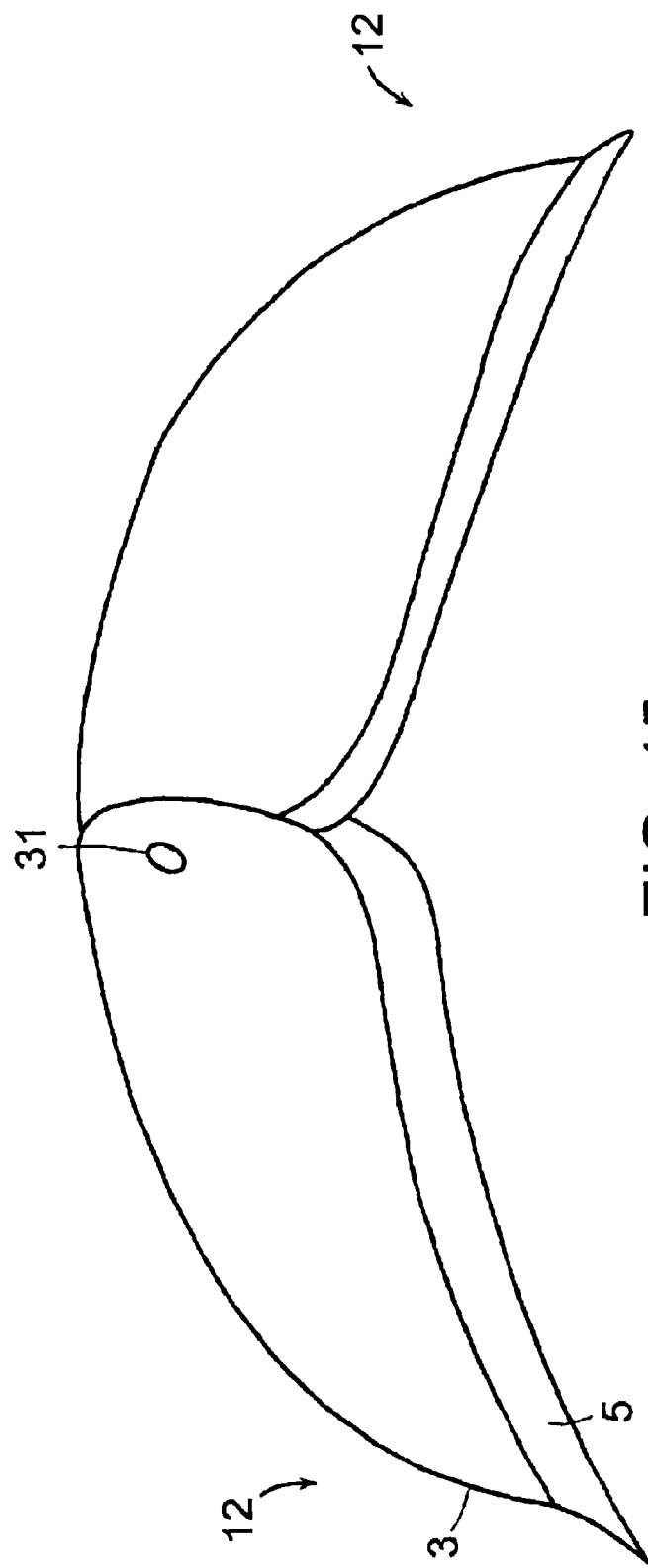
FIG. 15 shows side view of another embodiment of a bowtie shaped housing having a hinge for assisting a user in moving the sides of the housing toward and away from each other.

For example, in one embodiment, as shown in FIG. 15, a hinge-like mechanism 31 is located near the center of the top surface 2 so that one can manually open the hinge-like mechanism to spread the ends 12 of the housing away from each other. The hinge-like mechanism 31, which could, for example, use a torsion spring, will then return the ends 12 back to their natural state when released. In other embodiments, the elastic properties of the material forming the housing return the ends 12 back to their natural state.

Figure 13:
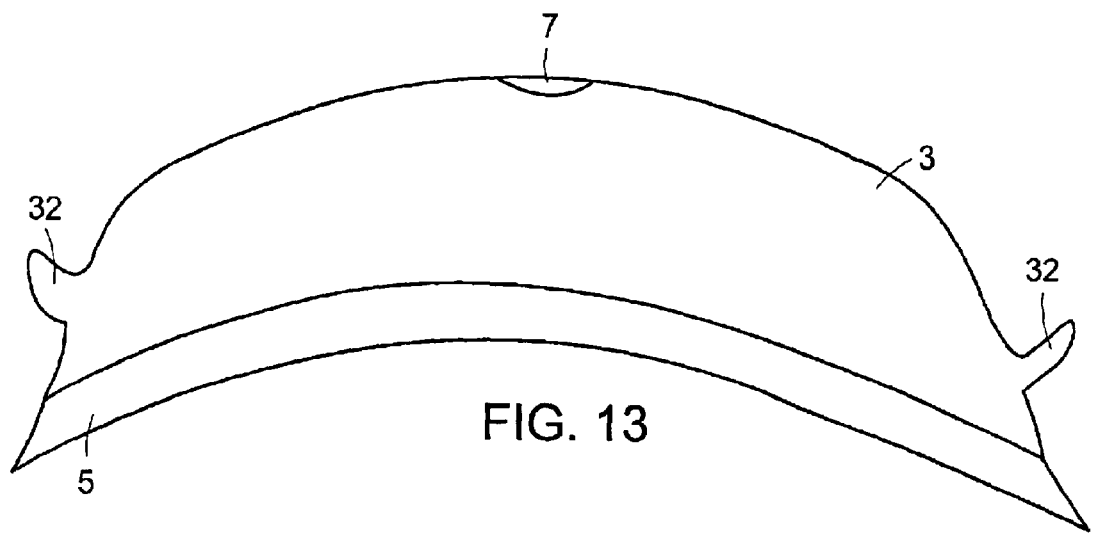
FIG. 13 shows a side view of another embodiment of a bowtie shaped housing having a spreading mechanism located on the outer side portions of the housing.
Figure 14:
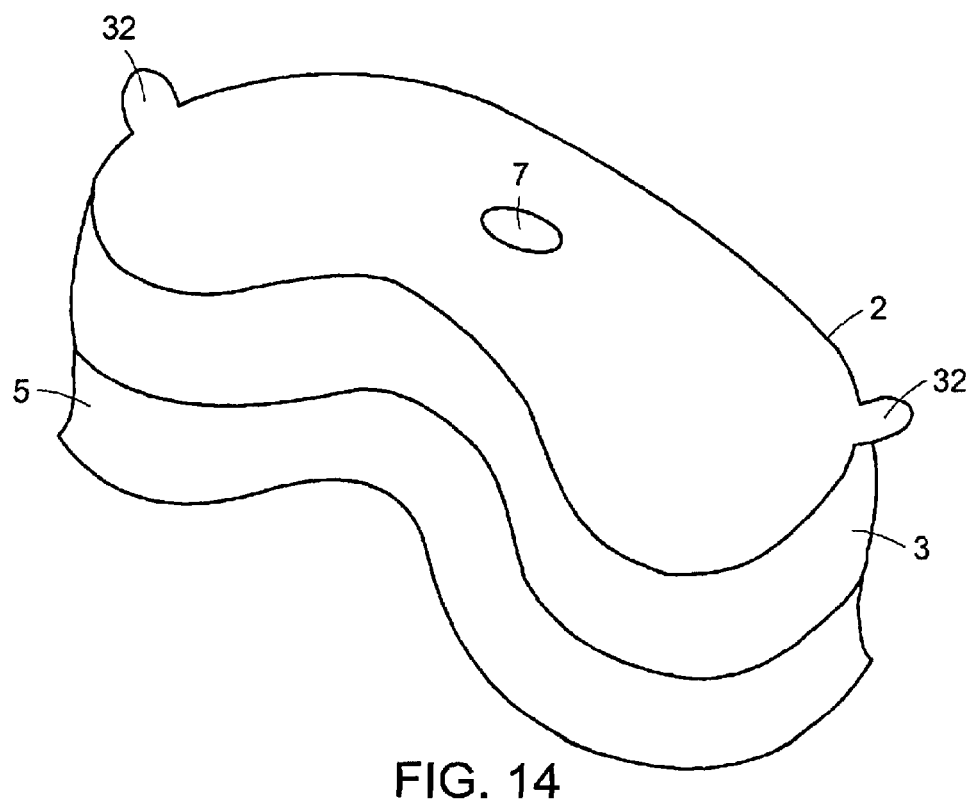
FIG. 14 shows an upper side perspective view of another embodiment of a bowtie shaped housing having a spreading mechanism located on the top surface of the housing.

In some embodiments, extensions 32 are located on the side portions 3, as shown in FIG. 13, or top surface 2, as shown in FIG. 14, such that one could place their fingers and thumb under the extensions 32 and push the extensions 32 upwards, thereby spreading the ends 12 of the housing apart. Release of the extensions 32 or other spreading mechanism 29 will allow the ends 12 to move back to their original state.

The size of the housing 1 can vary depending on the use of the device. For example, the device can be used on various organs and, as such, the size most suitable for each organ can vary. In some embodiments, custom devices are made, each designed for individual organs.

Thus, for example, when used on the heart, the device preferably has a length that is no longer than the surface of the heart on which the device is to be attached. For example, when the device is being attached along the length of the heart, the device preferably has a length no longer than the length of the heart. If the device is being attached around the device, along its "circumference", the device preferably has a length no longer than the "circumference" of the heart. In preferred embodiments, the size of the device provides a sufficiently large surface area to provide a strong seal of the device on the organ while also providing a small enough profile to prevent obstruction of the surgeon's view of the surgical field during use.

For example, in one preferred embodiment, the bowtie and elliptical shaped housings 1 preferably have a length at is longest point ranging from about 0.5" to about 3", more preferably, from about 1.5" to about 2". The greatest width of the bowtie and elliptical shaped housings 1 along its length preferably ranges from about 0.25" to about 1", more preferably, from about 0.375" to about 0.75". The thickness of the bowtie and elliptical shaped housings 1 preferably ranges from about 0.2" to about 0.5", more preferably, from about 0.25" to about 0.35". The height of the bowtie and elliptical shaped housings 1 preferably ranges from about 0.20" to about 0.50", more preferably, from about 0.25" to about 0.35". The thickness of the one or more flanges 5 of the bowtie-shaped or elliptical shaped housing 1 preferably ranges from about 0.005" to about 0.020", more preferably, from about 0.008" to about 0.012". The length of the one or more flanges 5 of the bowtie shaped housing 1 preferably ranges from about 0.05" to about 0.5", more preferably, from about 0.1" to about 0.25".

In some embodiments, the device of the present invention is held and manipulated manually. In other embodiments, a holding or manipulation mechanism is used to hold and/or manipulate the device of the present invention. For example, in some embodiments, the device of the present invention is attached to a device in the surgical field such as, for example, a retractor or similar device. In such embodiments, the device of the present invention preferably further includes a connection mechanism that connects the housing to the holding or manipulation mechanism.

Figure 52:
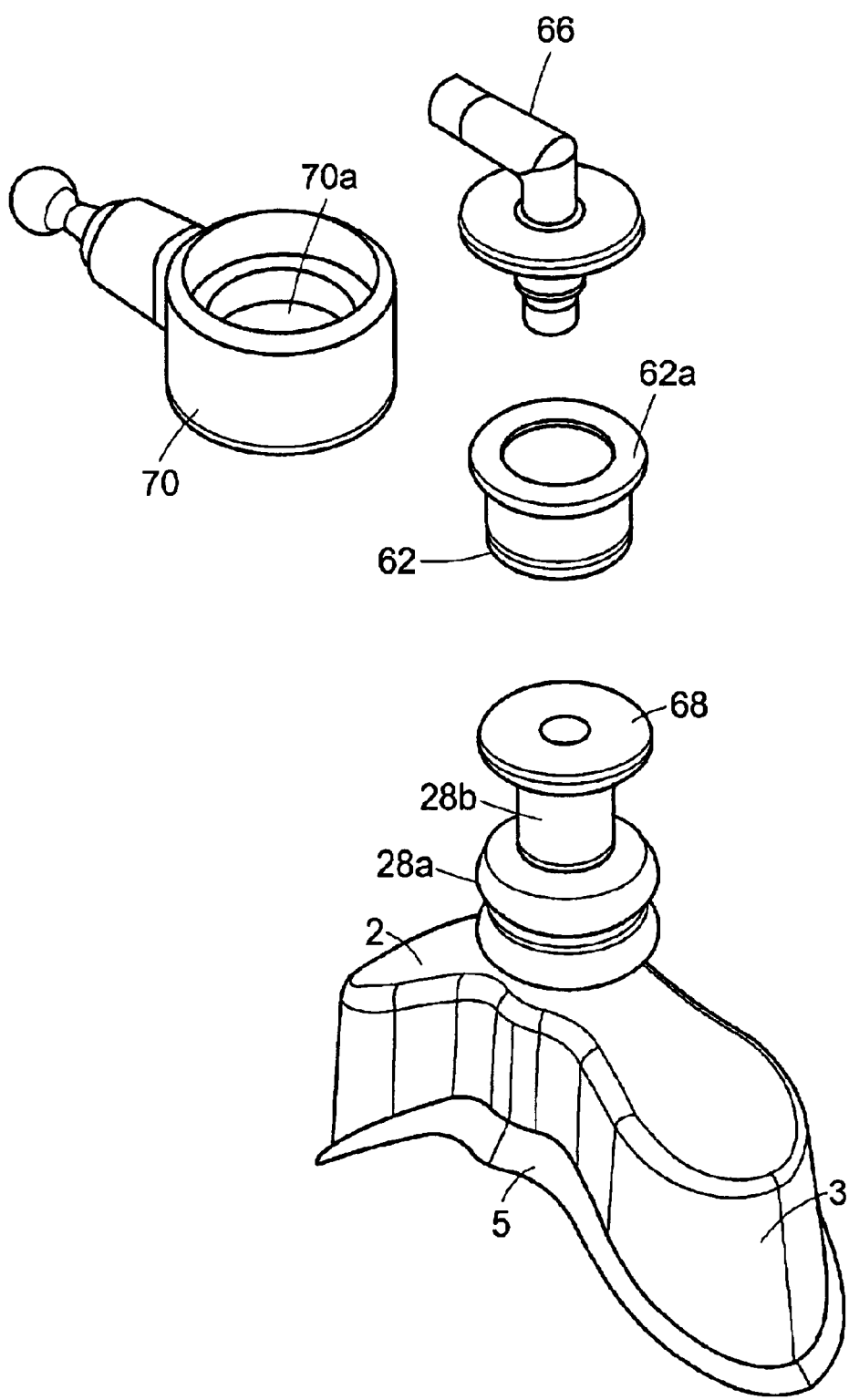
FIG. 52 shows an exploded view of a bowtie shaped device and a connection assembly for connecting the device to a holding mechanism in accordance with one embodiment of the present invention.
Figure 56:
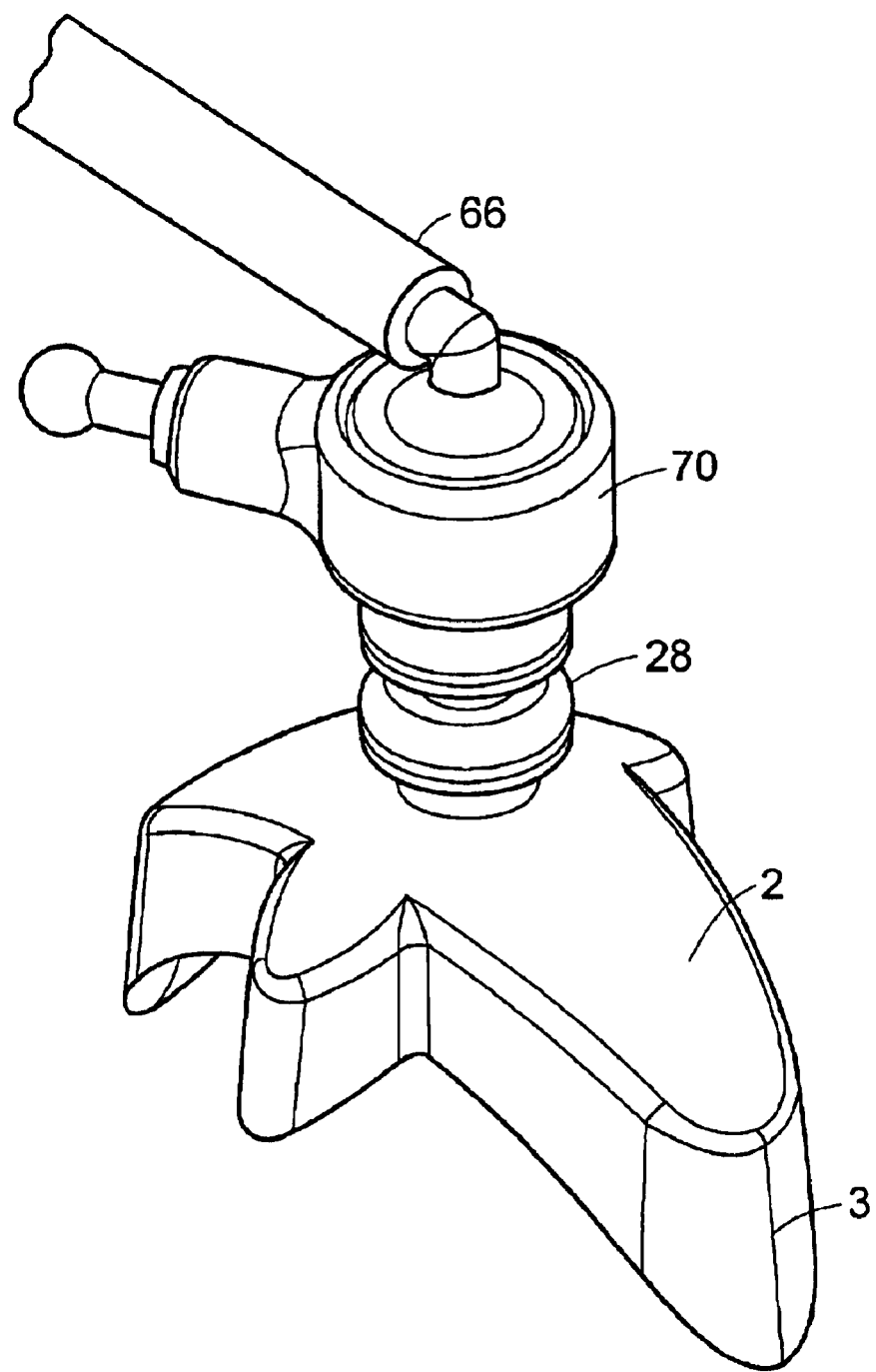
FIG. 56 shows a cross-shaped device having a connection assembly mounted on the device in accordance with one embodiment of the present invention.
Figure 57A:
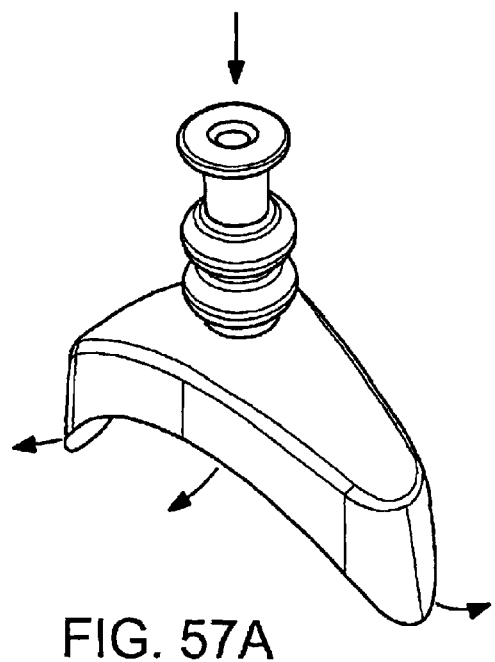
FIGS. 57a–b shows a side perspective view of the flattening or flare out of an elliptical device as the device is applied to the surface of an organ.
Figure 57B:
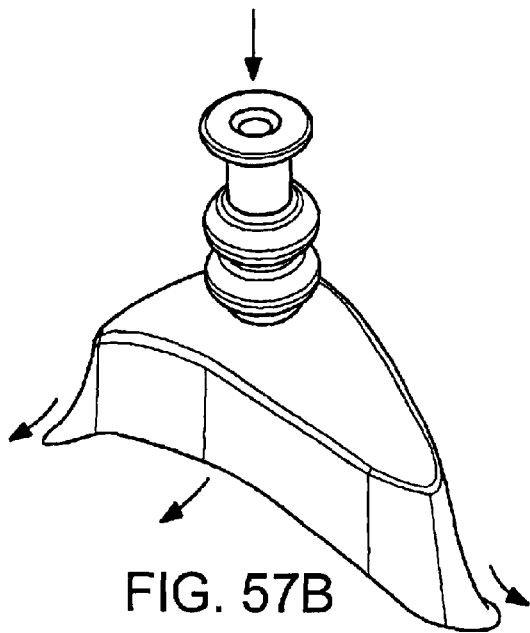
Figure 58A:
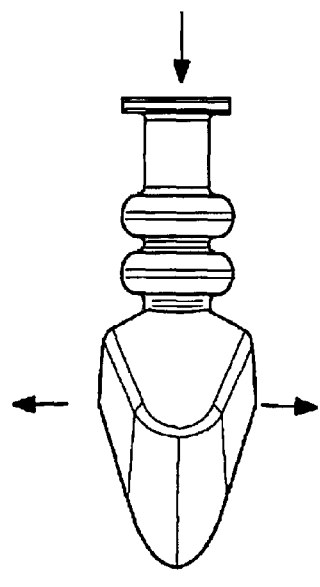
FIGS. 58a–b shows a front perspective view of the flattening or flare out of an elliptical device as the device is applied to the surface of an organ.
Figure 58B:
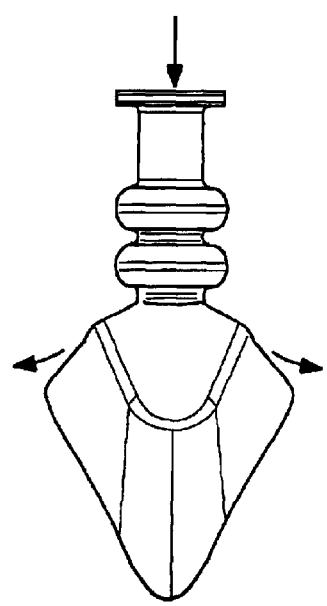

One embodiment of a connection mechanism is shown in FIGS. 52 and 56. This embodiment includes a bushing 62 or similar mechanism and a ring-type connector 70. Preferably, the bushing 62 fits over an extension from the top surface 2 of the housing, most preferably, the attachment mechanism 28. In one embodiment, the attachment mechanism 28 has ribbing along at least a portion of its length 28a, as described above, and a non-ribbed portion 28b over which the bushing 62 is attached. To maintain the bushing 62 securely attached to the housing 1, the attachment mechanism 28 preferably has an enlarged portion 68, preferably at or near its end, larger in cross section than the inner diameter of the bushing 62 that prevents the bushing 62 from sliding off of the attachment mechanism 28. The bushing 62, likewise, may also include an enlarged portion 62a that rests against the enlarged portion 68 of the attachment mechanism 28, and further prevents the bushing 62 from sliding off of the attachment mechanism 28. In this embodiment, the opening 70a in the ring-type connector 70 fits over the bushing 62. Preferably, the opening 70a in the ring-type connector is circular and sized to fit about the circular outer surface of the bushing 62 in a manner that allows rotational movement between the ring-type connector 70 and bushing 62. The ring-type connection assembly is designed to connect to the housing 1 in a manner that allows rotational movement between the ring-type connector 70 and bushing 62, but prevents the ring-type connector 70 from sliding off of the housing. For example, in one embodiment, the ring-type connector 70 and bushing 62 form a snap fit when connected. Protrusions along the ring connector 70 and/or bushing 62 may be formed to keep the ring-type connector 70 and bushing connected during use while still allowing rotational movement.

The connection mechanism may further include an elbow-type connector 66 through which a differential pressure source can be introduced to the housing 1. Of course, the elbow-type connector 66 can be eliminated if no differential pressure source is used or, for example, a simple piece of tubing can connect the differential pressure source to the housing. In embodiments including an elbow-type connector 66, the elbow-type connector 66 preferably connects the differential pressure source to the housing 1, preferably through the one or more apertures 7 in the housing 1. In one embodiment, as shown in FIGS. 52 and 56, the elbow-type connector 66 fits through an aperture in the attachment mechanism 28, extends upwards and at an angle, preferably at a 90° angle, away from the attachment mechanism 28 towards the differential pressure source. The elbow-type connector 66 is hollow along its length so that the differential pressure source can be introduced through the connector 66 to the housing 1.

Figure 53:
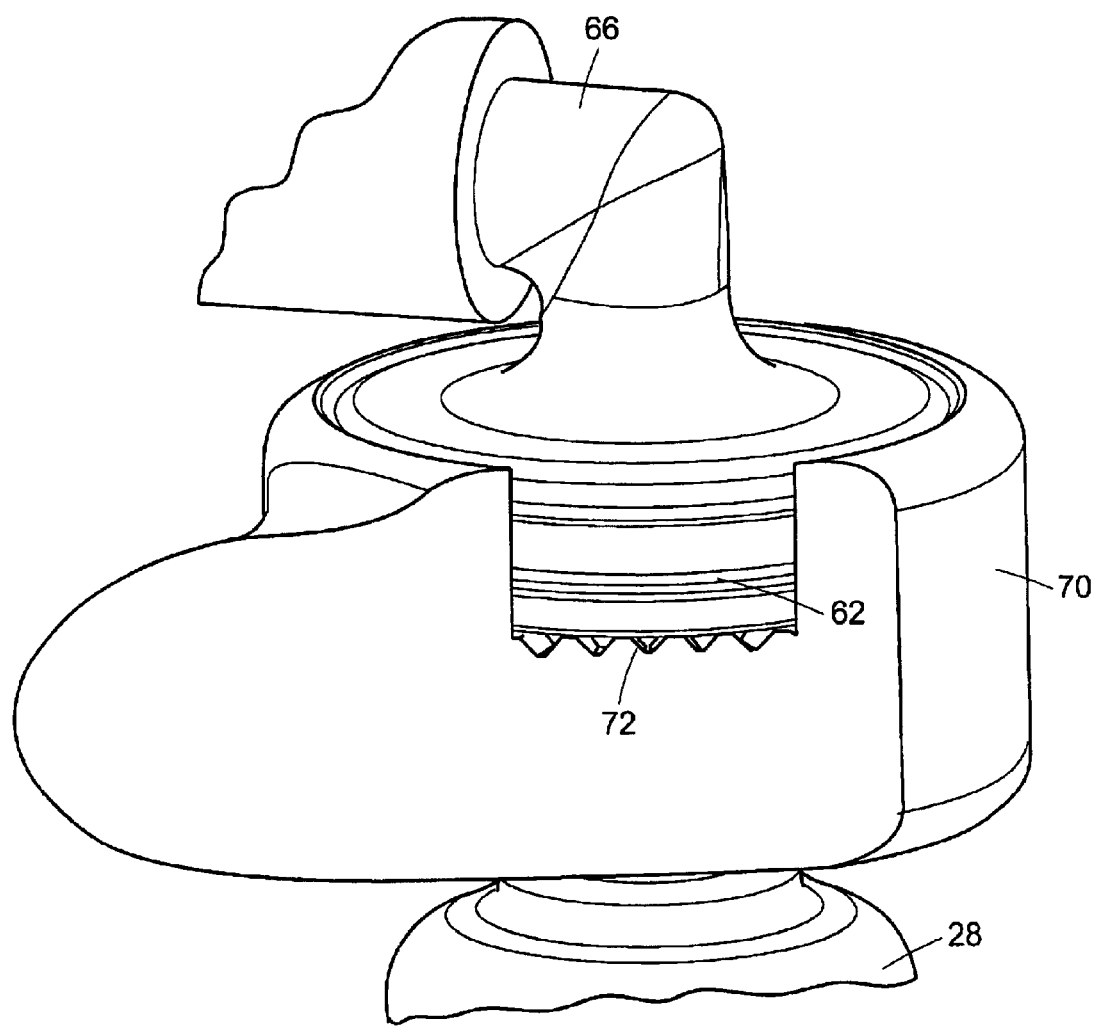
FIG. 53 shows another embodiment of a connection assembly for connecting the device to a holding mechanism.
Figure 54:
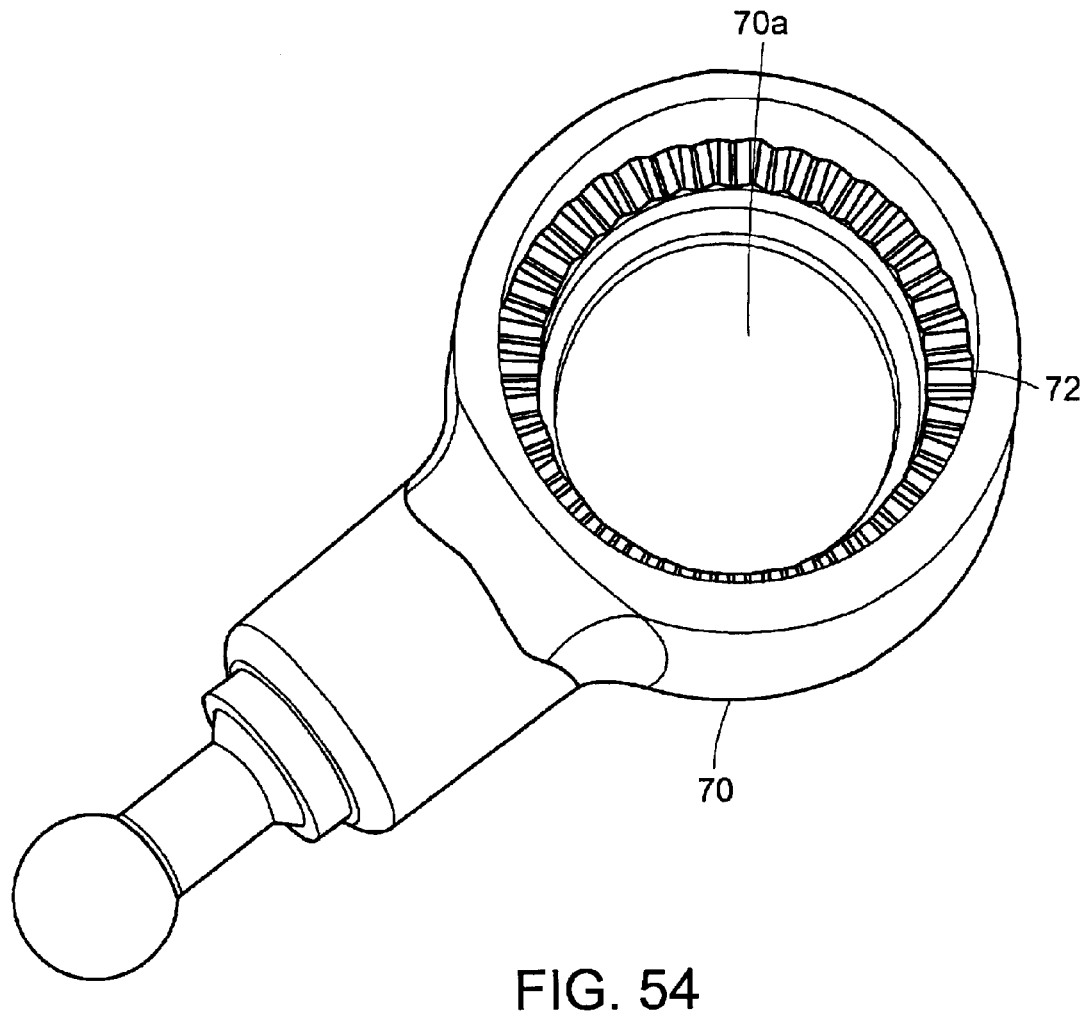
FIG. 54 shows a ring-type connector having a plurality of grooves in accordance with one embodiment of the present invention.
Figure 55:
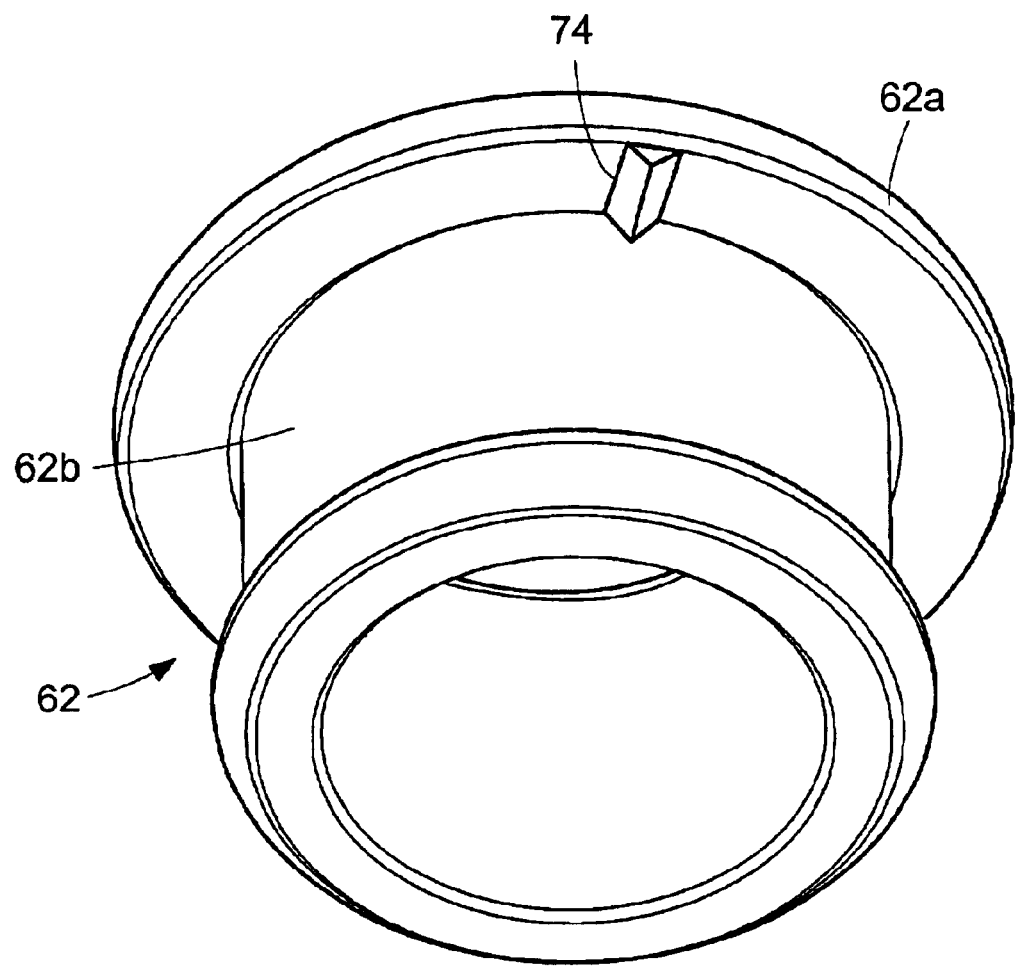
FIG. 55 shows a bushing having one or more protrusions in accordance with one embodiment of the present invention.

Another embodiment of a connection mechanism is shown in FIG. 53. This embodiment shows an elbow-type connector 66, bushing 62 and a cut-away view of a ring-type connector 70. As shown, the ring-type connector 70 includes grooves 72 along its inner surface in opening 70a. These grooves 72 are also shown in FIG. 54. The grooves 72 are designed to correspond to one or more protrusions 74 along the bushing 62, such that the one or more protrusions 74 fit within one or more grooves 72, thereby locking the device in place and preventing rotational movement between the ring-type connector 70 and bushing 62. In a particularly preferred embodiment, there are two protrusions 74 along the bushing and a plurality of grooves 72 along the ring-type connector 70. However, any combination of protrusions 74 and grooves 72 can be used. The protrusion is formed and positioned such that free rotation between the ring-type connector 70 and bushing 62 is allowed until a sufficient amount of downward force is applied to the housing 1 and connection mechanism, which causes the one or more protrusion 74 to lock within one or more grooves 72, thereby preventing further rotation between the ring-type connector 70 and bushing 62. Upon removal of the downward force, the one or more protrusions 74 are released from the one or more grooves 72 and the rotation between the ring-type connector 70 and bushing 62 can be resumed. As used herein, a "sufficient amount of downward force" applied to the housing 1 and connection mechanism corresponds to a force used to lift the organ.

For example, in one embodiment, the portion 62b of the bushing 62 over which the ring-type connector 70 fits is longer than the ring-type connector 70 such that a space in the portion 62b above the ring-type connector 70 is left open when the ring-type connector 70 is mounted on the bushing 62. The one or more protrusions 74 could be located in this space. Upon application of a sufficient amount of downward force on the housing 1 and connection mechanism, the bushing 62 slides downwards (in the direction of the applied force) towards the one or more grooves 72 of the ring-type connector 70.

Further, when the bushing 62 and ring-like connector 70 are interlocked (i.e. when the one or more protrusions 74 and one or more grooves 72 are engaged), rotational and axial energy transmitted by the organ through movement of the device or organ (e.g. the beating of the heart) can be accommodated and absorbed by the attachment mechanism 28, particularly in the region of the attachment mechanism 28 that is ribbed. This accommodation and absorption of energy prevents damage to the organ tissue. For example, this accommodation and absorption is particularly useful when the device is used on a beating heart because the device can be used to manipulate the heart without limiting its normal oscillatory contractions.

In the embodiments wherein a holding or manipulation mechanism (e.g. a retractor or similar device in the surgical field) is used to hold and/or manipulate the device of the present invention, the connection mechanism could be directly attached to the holding or manipulation mechanism. Alternatively, in some embodiments, the connection mechanism is fastened to a holding or manipulation mechanism in the surgical field using a device such as a segmented arm support system described in U.S. Ser. No. 10/008,509, the teachings of which are incorporated herein by reference, wherein the segmented arm system is connected, for example, to an arm or rack section of the retractor and also retains the device of the present invention in a desired position.

The segmented arm system includes generally an elongated articulating arm having a proximal mounting assembly for attachment to the retractor or similar device and a distal connector thereon for releasably connecting the device of the present invention to the articulating arm. The distal connector allows the stabilization device to be pivotally and slidably moved to a desired position into contact with the predetermined area of the tissue of the patient. The segmented arm system preferably includes a plurality of segments positioned along the length of the arm. The segments provide a plurality of locations for relative movement of the stabilization device as well as providing locations for fixing the desired position of the stabilization arm system along the retractor and relative to the stabilization device. The movable segments also allow the user to position at least a portion of the plurality of arm segments away from the desired surgical site so that the articulating arm does not obstruct the view of the surgeon or the assistant while providing sufficient leverage to provide a stable surgical site and to allow access to various locations on the heart of the patient.

The use of the manipulation device of the present invention can be further understood from the following discussion relating to a method for moving and positioning the heart and with reference to FIGS. 1–52.

Access to the organ is first provided by making an incision. The device is then placed on the surface of the organ and, as the device is brought into contact with the surface of the organ, the user may manipulate and shape the housing as desired so that the one or more flanges 5, side portions 3, arms 30 or other portions of the device properly contact and form a seal on the surface of the organ. If used, the source of differential pressure 6 is turned on and a secure seal formed.

Once the organ is securely gripped by the device, the organ can be lifted, turned, moved and held in various positions so that a medical practitioner can perform various diagnostic procedures, tests, treatments and surgical procedures on the organs. In some embodiments, the device is manually held. In other embodiments, the gripping member is fastened to a retractor or similar device in the surgical field.

In some embodiments, before the side portions 3 or flanges 5 are brought into contact with the surface of the heart, the ends 12 of the bowtie, elliptical, cross or multi-arm shaped housing 1 are first separated from each other, for example, using extensions 32. The side portions 3, flanges 5 or arms 30 then form a seal on the surface of the organ, as the natural elasticity of the housing material, or in some embodiments the energy of the torsion spring, pulls the ends back together.

During use, the bowtie, elliptical, cross and multi-arm shaped housings 1 are believed to improve conformance to the stretching surfaces of the organs (e.g. the stretching ventricles of a heart) as it is lifted, by the mechanism of "wing flex". After attaching to the organ surface (e.g. the ventricular epicardium) the arms or end portions of the bowtie/elliptical shaped housing adduct (close together) as the organ (e.g. ventricle) stretches during lift. Therefore, it is believed that as a result, lifting will be less demanding on the seals holding the device to the organ.

Likewise the cup-shaped housing 1 stretches upwards as the organ (e.g. ventricles) stretch when a heart is lifted. This upwards stretching of the organ is believed to pull the cup tighter about the surface of the organ to maintain and enhance the seal of the device on the organ.

In some embodiments, the device is manipulated and held manually during a procedure. In other embodiments the device is fastened to a holding mechanism in the surgical field, e.g. a retractor or similar device, which assists in holding the organ in a desired position. For example, in one embodiment, the device is attached to a holding mechanism in the surgical field via a connection mechanism. The connection mechanism preferably allows for rotational movement of the housing 1 to allow for movement of the device and/or organ without loss of adherence to the organ. For example, in one embodiment, the connection mechanism includes a ring-type connector 70 described above and bushing 62, wherein the ring type connector 70 and bushing 62 can rotate with respect to each other. In some embodiments, the ring-type connector 70 includes a plurality of grooves 72 and the bushing 62 includes one or more protrusions 74, as set out above. During use, the ring-type connector 70 would be mounted on the bushing 62, and until the one or more protrusions 74 engage one or more grooves 72, the ring-type connector 70 and bushing 62 would be allowed to rotate with respect to each other. Thus, for example, the connection mechanism would be mounted on the device of the present invention and connected to the holding mechanism in the surgical field. The device of the present invention could then be positioned as desired to contact an organ surface. The device of the present invention would be capable of rotational movement via the ring-type connector 70 and bushing 62 to facilitate proper positioning of the device on the organ surface. Then, the device could be adhered to the organ and the organ manipulated as desired. To lock the rotational movement of the device, the one or more protrusions 74 would be allowed to engage the one or more grooves 72, e.g. by applying a sufficient amount of downward force to the housing and connection mechanism. If rotational movement is required during the procedure, the one or more protrusions 74 would be removed from the one or more grooves 72.

In some embodiments, the device of the present invention is attached to a holding mechanism in the surgical field through the connection mechanism and a device such as a segmented arm support system described above and in U.S. Ser. No. 10/008,509. In this embodiment, the device of the present invention would be attached to the segmented arm support system via the connection mechanism. The segmented arm support system would then be attached to, for example, a retractor in the surgical field. The segmented arm support system could then be used to hold and manipulate the device as set out in U.S. Ser. No. 10/008,509

In some embodiments, the housing 1 can be modified to promote flattening rather than buckling of side portions 3 of the device. This can be done by thickening the side portions 3, stiffening the side portions (higher durometer material) and shortening the side portions.

Any of the housing embodiments can be used in accordance with the above procedure. For example, a particular shaped device could be used for particular procedures based on the desired use of the device. For example, a particular device profile may be chosen which will provide the user with better access to the organ. For example, the device profile may be minimized at certain locations to maximize surgeon work space (e.g. a bowtie shaped device may be used to minimize the profile of the device along the center of the device).

While described mainly with reference to use on the heart, it is to be understood that the manipulation device can also be used similarly on other organs of the body.

The present invention also includes kits that comprise one or more manipulation device of the invention. Kits of the invention also may include various gels, flexible films and similar materials to enhance the device's grip on the organs, one or more housings 1, screens 20, reinforcing members 24, connection mechanisms etc. for use with the delivery device 1, and/or written instructions for use of the delivery device 1 and other components of the kit.

All documents mentioned herein are incorporated by reference herein in their entirety.

The foregoing description of the invention is merely illustrative thereof, and it is understood that variations and modifications can be effected without departing from the scope or spirit of the invention as set forth in the following claims.

What is claimed is:

1. A device for internal organ manipulation comprising:
a housing having a top surface; and
at least one portion of the housing being adapted for adherence to any surface of any internal organ, whereby the at least one portion of the housing adheres the device to the organ and whereby the device is used to lift, position, move and otherwise manipulate the internal organ;

wherein at least two portions of the housing are adapted for adherence to any surface of an organ such that the at least two portions form multiple, independent seals on the internal organ surface;

further comprising one or more apertures in the housing through which a source of differential pressure is used in connection with the housing, whereby the source of differential pressure assists the housing in adhering to the organ;

wherein the one or more apertures are positioned such that each multiple, independent seal formed by the at least two portions is assisted by the differential pressure source;

wherein the differential pressure provided to each multiple, independent seal is independent of the differential pressure provided to the other multiple, independent seals; and wherein a single source of differential pressure provides each multiple, independent seal with differential pressure and wherein the differential pressure provided to each seal is made independent by positioning valves in line with each aperture.

2. A device for internal organ manipulation comprising:
a housing having a top surface; and
at least one portion of the housing being adapted for adherence to any surface of any internal organs whereby the at least one portion of the housing adheres the device to the organ and whereby the device is used to lift, position, move and otherwise manipulate the internal organ;

wherein at least two portions of the housing are adapted for adherence to any surface of an organ such that the at least two portions form multiple, independent seals on the internal organ surface;

further comprising one or more apertures in the housing through which a source of differential pressure is used in connection with the housing, whereby the source of differential pressure assists the housing in adhering to the organ;

wherein the one or more apertures are positioned such that each multiple, independent seal formed by the at least two portions is assisted by the differential pressure source;

wherein the differential pressure provided to each multiple, independent seal is independent of the differential pressure provided to the other multiple, independent seals; and further comprising a parent tube or lumen extending from the differential pressure source and independent daughter tubes or lumens extending from the parent tube to each aperture.

3. The device of claim 2, wherein a single source of differential pressure provides each multiple, independent seal with differential pressure and wherein the differential pressure provided to each seal made independent by making the diameter of each daughter tube less than the diameter of the parent tube.

4. The device of claim 3, wherein the diameter of the parent tube is at least double the diameter of each daughter tube.

5. A device for internal organ manipulation comprising:

a housing having a top surface; and at least one portion of the housing being adapted for adherence to any surface of any internal organ, whereby the at least one portion of the housing adheres the device to the organ and whereby the device is used to lift, position, move and otherwise manipulate the internal organ; and further comprising a gel or flexible film within the housing, whereby, as the housing is applied to an internal organ surface, the gel or flexible film is released from the housing to the at least one portions of the housing adapted for adherence to any surface of any internal organ.

6. A device for internal organ manipulation comprising:

a housing having a top surface; and at least one portion of the housing being adapted for adherence to any surface of any internal organ, whereby the at least one portion of the housing adheres the device to the organ and whereby the device is used to lift, position, move and otherwise manipulate the internal organ;

wherein the housing includes at least two ends and wherein the device further comprises a spreading mechanism for moving the ends of the housing away from each other.

7. The device of claim 6, wherein the spreading mechanism comprises a hinge located between the ends.

8. The device of claim 6, wherein the spreading mechanism comprises at least two extensions from the housing that are pushed to spread the ends of the housing away from each other.

9. The device of claim 6, further comprising a connection mechanism and a holding mechanism, whereby the connection mechanism attaches the device to the holding mechanism during use.

10. The device of claim 9, wherein the connection mechanism is mounted on an attachment mechanism that extends from the top surface of the housing.

11. The device of claim 10, wherein the attachment mechanism is flexible along its length, whereby the flexibility along the length of the attachment mechanism allows energy absorption and multidirectional movement of the housing as the internal organ moves.

12. The device of claim 11, whereby the attachment mechanism has at least a ribbed portion along its length.

13. The device of claim 9, wherein the connection mechanism comprises a connector that is mounted on the housing and is rotatable with respect to the housing.

14. The device of claim 13, wherein the connection mechanism further comprises a bushing, whereby the bushing is mounted on the housing and the connector is mounted on the bushing and whereby the bushing and connector are rotatable with respect to each other.

15. The device of claim 14, wherein the connector includes at least one groove along its inner surface and the bushing includes at least one protrusion, whereby the at least one protrusion fits within the at least one groove to prevent rotational movement between connector and bushing.

16. The device of claim 15, wherein the connector and bushing are rotatable with respect to each other until a sufficient downward force is applied to the housing and connection mechanism.

17. The device of claim 16, whereby upon removal of the sufficient downward force, the one or more protrusions are released from the one or more grooves such that the connector and bushing are rotatable with respect to each other.

18. The device of claim 6, wherein the top surface of the housing has an overall multi arm shape.

* * * * *